United States Patent
Saphier et al.

(10) Patent No.: US 12,370,025 B2
(45) Date of Patent: Jul. 29, 2025

(54) INTUITIVE INTRAORAL SCANNING

(71) Applicant: Align Technology, Inc., San Jose, CA (US)

(72) Inventors: Ofer Saphier, Rechovot (IL); Shai Ayal, Shoham (IL); Pavel Agniashvili, Moscow (RU); Pavel Veryovkin, Krasnogorsk (RU); Maxim Volgin, Moscow (RU)

(73) Assignee: Align Technology, Inc., San Jose, CA (US)

( * ) Notice: Subject to any disclaimer, the term of this patent is extended or adjusted under 35 U.S.C. 154(b) by 337 days.

(21) Appl. No.: 17/880,563

(22) Filed: Aug. 3, 2022

(65) Prior Publication Data
US 2023/0042643 A1 Feb. 9, 2023

Related U.S. Application Data

(60) Provisional application No. 63/230,668, filed on Aug. 6, 2021.

(51) Int. Cl.
*A61C 9/00* (2006.01)
*A61B 1/00* (2006.01)
*A61B 1/24* (2006.01)

(52) U.S. Cl.
CPC ........ *A61C 9/0053* (2013.01); *A61B 1/00172* (2013.01); *A61B 1/24* (2013.01)

(58) Field of Classification Search
CPC . A61C 9/0053; A61C 9/0046; A61B 1/00172; A61B 1/24; A61B 5/0088; G06T 2207/30036; G06T 7/38; G06T 17/00
See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |

(Continued)

FOREIGN PATENT DOCUMENTS

| | | | | |
|---|---|---|---|---|
| EP | 2074940 A1 | * | 7/2009 | ........... A61B 5/0088 |
| JP | 2002516052 A | * | 5/2002 | |

OTHER PUBLICATIONS

Isola, et al. "Image-to-image translation with conditional adversarial networks." Proceedings of IEEE conference on computer vision and pattern recognition; 2017; pp. 1125-1134.

*Primary Examiner* — Umair Ahsan
(74) *Attorney, Agent, or Firm* — Lowenstein Sandler LLP

(57) ABSTRACT

An intraoral scanning system includes an intraoral scanner and a computing device. The computing device receive a plurality of intraoral scans from the intraoral scanner during an intraoral scanning session; registers the plurality of intraoral scans together based on overlapping features of the plurality of intraoral scans; generates a first three-dimensional (3D) surface based on the plurality of intraoral scans; receives one or more additional intraoral scans; determines that the one or more additional intraoral scans fail to satisfy one or more registration criteria for registering to at least one of the plurality of intraoral scans or the first 3D surface; and generates a second 3D surface based on the one or more additional intraoral scans.

27 Claims, 18 Drawing Sheets

(56) References Cited

U.S. PATENT DOCUMENTS

| | | |
|---|---|---|
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Ariel et al. |
| 11,096,765 B2 | 8/2021 | Yossef et al. |
| 11,238,586 B2 | 2/2022 | Mikhail et al. |
| 11,367,192 B2 | 6/2022 | Avi et al. |
| 11,455,727 B2 | 9/2022 | Mikhail et al. |
| 11,478,132 B2 | 10/2022 | Kopelman et al. |
| 2016/0135925 A1 | 5/2016 | Mason et al. |
| 2018/0005371 A1* | 1/2018 | Sabina ................. A61C 9/0046 |
| 2019/0029784 A1 | 1/2019 | Moalem et al. |
| 2019/0269485 A1* | 9/2019 | Elbaz ................. A61B 1/00016 |
| 2019/0388193 A1 | 12/2019 | Saphier et al. |
| 2020/0038149 A1* | 2/2020 | Levin ....................... A61B 1/24 |
| 2020/0281702 A1 | 9/2020 | Avi et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0090272 A1 | 3/2021 | Meyer et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0150702 A1* | 5/2021 | Claessen ................. G06T 17/10 |
| 2021/0196152 A1 | 7/2021 | Saphier et al. |
| 2021/0321872 A1 | 10/2021 | Saphier et al. |

* cited by examiner

402

404

406

INTUITIVE INTRAORAL SCANNING

RELATED APPLICATIONS

This application claims the benefit of U.S. Provisional Application No. 63/230,668, filed Aug. 6, 2021, the entire content of which is hereby incorporated by reference.

TECHNICAL FIELD

Embodiments of the present disclosure relate to the field of intraoral scanning and, in particular, to a system and method for improving the efficiency and accuracy of intraoral scanning.

BACKGROUND

In both prosthodontic and orthodontic procedures, obtaining a three-dimensional (3D) model of a dental site in the oral cavity is an initial procedure that is performed. In orthodontic procedures it can be important to provide a model of one or both jaws. 3D models created by the use of an intraoral scanner aid in the accurate creation of molds for corrective work. Scanning may typically be performed when a patient comes in for a progress update check, to receive additional treatment, or sometimes during a routine hygiene appointment.

The process of performing intraoral scanning has historically been cumbersome, time consuming and non-intuitive to perform. Intraoral scanning relies on the ability to register and stitch intraoral scans of a scan session together to generate an accurate and complete 3D model. Frequently, scans of a scan session may not be registered due to insufficient overlap between scans, due to poor data, due to an operator moving an intraoral scanner too fast, and for other reasons. Scans that cannot be registered to another scan of the scan session are discarded, and scanning software interrupts the scanning session by entering a recovery mode to rescan any areas associated with discarded intraoral scans. Furthermore, many scanners have a difficult time initializing after an interruption due to insufficient overlap between scans or excessive intraoral scanner movement. Such limitations are frustrating and impose additional time to work through for a doctor.

Due to the non-intuitive nature of existing scanning procedures, training is typically performed to train operators to properly perform intraoral scanning using an intraoral scanner. Such training consumes time and resources both on the part of the dentist or technician being trained and on the part of the manufacturer of the intraoral scanner.

SUMMARY

In a first aspect of the disclosure, a method comprises: receiving a plurality of intraoral scans during an intraoral scanning session; registering the plurality of intraoral scans together based on overlapping features of the plurality of intraoral scans; generating a first three-dimensional (3D) surface based on the plurality of intraoral scans; receiving one or more additional intraoral scans; determining that the one or more additional intraoral scans fail to satisfy one or more registration criteria for registering to at least one of the plurality of intraoral scans or the first 3D surface; and generating a second 3D surface based on the one or more additional intraoral scans without interrupting the intraoral scanning session.

A second aspect of the disclosure may further extend the first aspect of the disclosure. In the second aspect of the disclosure, the method further comprises: estimating, after failing to satisfy the one or more registration criteria, a position and orientation of the second 3D surface relative to the first 3D surface without use of information from a previous intraoral scanning session and without use of information from a scanning protocol.

A third aspect of the disclosure may further extend the first or second aspect of the disclosure. In the third aspect of the disclosure, the method further comprises: receiving movement data from an intraoral scanner that generated the plurality of intraoral scans and the one or more additional intraoral scans, wherein the movement data indicates an amount of movement of the intraoral scanner between generation of a first intraoral scan of the plurality of intraoral scans and a second intraoral scan of the one or more additional intraoral scans; and determining at least one of the position or orientation of the second 3D surface relative to the first 3D surface based on the movement data.

A fourth aspect of the disclosure may further extend the third aspect of the disclosure. In the fourth aspect of the disclosure, the movement data is generated by an inertial measurement unit of the intraoral scanner, and wherein the orientation of the second 3D surface relative to the first 3D surface is determined based on the movement data, the method further comprising: receiving a plurality of two-dimensional (2D) images during the intraoral scanning session, wherein each of the plurality of 2D images is associated with one of the plurality of intraoral scans or one of the one or more additional intraoral scans; estimating a position change between at least a first scan of the plurality of intraoral scans and the one or more additional intraoral scans using two or more of the plurality of 2D images; and determining the position of the second 3D surface relative to the first 3D surface based on the estimated position change.

A fifth aspect of the disclosure may further extend the first through fourth aspects of the disclosure. In the fifth aspect of the disclosure, the method further comprises: determining, based on a result of the registering, a position change or an orientation change between at least two intraoral scans of the plurality of intraoral scans; determining, based on timing for the at least two intraoral scans and based on at least one of the position change or the orientation change, at least one of a rate of position change or a rate of orientation change; and determining, based on a timing of the one or more additional intraoral scans and at least one of the rate of position change or the rate of orientation change, the position and orientation of the second 3D surface relative to the first 3D surface.

A sixth aspect of the disclosure may further extend the first through fifth aspects of the disclosure. In the sixth aspect of the disclosure, the method further comprises: receiving a plurality of two-dimensional (2D) images during the intraoral scanning session, wherein each of the plurality of 2D images is associated with one of the plurality of intraoral scans; determining, based on a result of the registering, a position change or an orientation change between at least two 2D images of the plurality of 2D images; determining, based on timing for the at least two 2D images and based on at least one of the position change or the orientation change, at least one of a rate of position change or a rate of orientation change; receiving one or more additional 2D images, wherein each of the one or more additional 2D images is associated with one of the one or more additional intraoral scans; and determining, based on a timing of the one or more additional 2D images and at least one of the rate of position change or the rate of orientation change, the position and orientation of the second 3D surface relative to the first 3D surface.

A seventh aspect of the disclosure may further extend the first through sixth aspects of the disclosure. In the seventh aspect of the disclosure, the method further comprises: inputting a first input based on the first 3D surface into a trained machine learning model, wherein the trained machine learning model outputs first canonical position coordinates for a first position and orientation of the first 3D surface relative to a canonical position of a jaw; and inputting a second input based on the second 3D surface into the trained machine learning model, wherein the trained machine learning model outputs second canonical position coordinates for a second position and orientation of the second 3D surface relative to the canonical position of the jaw.

An eighth aspect of the disclosure may further extend the first through seventh aspects of the disclosure. In the eighth aspect of the disclosure, the method further comprises: receiving a plurality of two-dimensional (2D) images during the intraoral scanning session, wherein each of the plurality of 2D images is associated with one of the plurality of intraoral scans; receiving one or more additional 2D images, wherein each of the one or more additional 2D images is associated with one of the one or more additional intraoral scans; inputting a first input based on at least a subset of the plurality of 2D images into a trained machine learning model, wherein the trained machine learning model outputs first canonical position coordinates for a first position and orientation of the first 3D surface relative to a canonical position of the jaw; and inputting a second input based on at least a subset of the one or more additional 2D images into the trained machine learning model, wherein the trained machine learning model outputs second canonical position coordinates for a second position and orientation of the second 3D surface relative to the canonical position of the jaw.

A ninth aspect of the disclosure may further extend the first through eighth aspects of the disclosure. In the ninth aspect of the disclosure, the method further comprises: inputting an input based on the first 3D surface and the second 3D surface into a trained machine learning model, wherein the trained machine learning model outputs the relative position and orientation of the second 3D surface and the first 3D surface.

A tenth aspect of the disclosure may further extend the first through ninth aspects of the disclosure. In the tenth aspect of the disclosure, the method further comprises: receiving a further intraoral scan; determining that the further intraoral scan satisfies the one or more registration criteria for registering to at least one of the one or more additional intraoral scans or the second 3D surface; determining that the further intraoral scan satisfies the one or more registration criteria for registering to at least one of the plurality of intraoral scans or the first 3D surface; and registering the first 3D surface with the second 3D surface using the further intraoral scan.

An eleventh aspect of the disclosure may further extend the tenth aspect of the disclosure. In the eleventh aspect of the disclosure, the method further comprises: merging the first 3D surface and the second 3D surface into a combined 3D surface.

A twelfth aspect of the disclosure may further extend the first through eleventh aspects of the disclosure. In the twelfth aspect of the disclosure, the method further comprises: determining one or more reasons that the one or more additional intraoral scans failed to satisfy the one or more registration criteria for registering to at least one of the plurality of intraoral scans or the first 3D surface; and providing feedback regarding the one or more reasons.

A thirteenth aspect of the disclosure may further extend the twelfth of the disclosure. In the thirteenth aspect of the disclosure, the one or more reasons are selected from the group consisting of: an intraoral scanner was moved too quickly, the intraoral scanner is too far from a dental site being scanned, the intraoral scanner is too close to the dental site being scanned, there is insufficient overlap between the one or more additional intraoral scans and at least one of the plurality of intraoral scans or the 3D surface, a window of the intraoral scanner is dirty, the dental site is obstructed by moving tissue, the dental site is obstructed by blood or saliva, and the dental site lacks sufficient surface features.

A fourteenth aspect of the disclosure may further extend the first through thirteenth aspects of the disclosure. In the fourteenth aspect of the disclosure, the method further comprises: determining one or more reasons why the one or more additional intraoral scans fail to satisfy the one or more registration criteria or are close to failing the one or more registration criteria; and outputting, via a dashboard of a graphical user interface, a notice indicating the one or more reasons why the one or more additional intraoral scans fail to satisfy the one or more registration criteria or are close to failing the one or more registration criteria.

A fifteenth aspect of the disclosure may further extend the fourteenth aspect of the disclosure. In the fifteenth aspect of the disclosure, the method further comprises: periodically determining values for a plurality of metrics associated with the one or more registration criteria; and outputting the values for the plurality of metrics via the dashboard of the graphical user interface.

A sixteenth aspect of the disclosure may further extend the first through fifteenth aspects of the disclosure. In the sixteenth aspect of the disclosure, the method further comprises: determining a speed of movement of an intraoral scanner that generated the plurality of intraoral scans; determining whether the speed of movement exceeds a speed threshold; and outputting a warning responsive to determining that the speed of movement exceeds the speed threshold.

A seventeenth aspect of the disclosure may further extend the first through sixteenth aspects of the disclosure. In the seventeenth aspect of the disclosure, the method further comprises: determining a speed of movement of an intraoral scanner that generated the plurality of intraoral scans; and outputting an indication of the speed of movement of the intraoral scanner.

An eighteenth aspect of the disclosure may further extend the first through seventeenth aspects of the disclosure. In the eighteenth aspect of the disclosure, the method further comprises: determining a speed of movement of an intraoral scanner that generated the plurality of intraoral scans; determining whether the speed of movement exceeds a speed threshold; outputting a first indication of the speed of movement using a first visualization responsive to determining that the speed of movement is below the speed threshold; and outputting a second indication of the speed of movement using a second visualization responsive to determining that the speed of movement exceeds the speed threshold.

A nineteenth aspect of the disclosure may further extend the first through eighteenth aspects of the disclosure. In the nineteenth aspect of the disclosure, the method further comprises: determining that the one or more additional intraoral scans failed to satisfy the one or more registration criteria because of a dirty window of an intraoral scanner that generated the plurality of intraoral scans; and outputting a notice that intraoral scanner has the dirty window.

A 20th aspect of the disclosure may further extend the first through nineteenth aspects of the disclosure. In the 20th aspect of the disclosure, the method further comprises: determining an amount of the window that is dirty; and outputting an indication of the amount of the window that is dirty.

A 21st aspect of the disclosure may further extend the first through 20th aspects of the disclosure. In the 21st aspect of the disclosure, the method further comprises: determining that the one or more additional intraoral scans failed to satisfy the one or more registration criteria because of an amount of detected moving tissue exceeding a threshold amount of moving tissue; and outputting a notice that an excessive amount of moving tissue was detected.

A 22nd aspect of the disclosure may further extend the 21st aspect of the disclosure. In the 22nd aspect of the disclosure, the method further comprises: inputting an input based on at least one of the one or more additional intraoral scans or one two-dimensional (2D) images associated with the one or more additional intraoral scans into a trained machine learning model, wherein the trained machine learning model outputs an indication of moving tissue that was detected.

A 23rd aspect of the disclosure may further extend the 21st aspect of the disclosure. In the 23rd aspect of the disclosure, the method further comprises: determining a percentage of the one or more additional intraoral scans that depicts the moving tissue; and outputting an indication of the percentage of the one or more additional intraoral scans that depicts the moving tissue.

A 24th aspect of the disclosure may further extend the first through 23rd aspects of the disclosure. In the 24th aspect of the disclosure, the method further comprises: determining a distance between one or more points in the one or more intraoral scans and a head of an intraoral scanner that generated the one or more intraoral scans; determining that the distance is further than a distance threshold; and outputting a notice to move the head of the intraoral scanner closer to a dental site being scanned.

A 25th aspect of the disclosure may further extend the first through 24th aspects of the disclosure. In the 25th aspect of the disclosure, the method further comprises: determining a distance between one or more points in the one or more intraoral scans and a head of an intraoral scanner that generated the one or more intraoral scans; determining that the distance is nearer than a distance threshold; and outputting a notice to move the head of the intraoral scanner further from a dental site being scanned.

A 26th aspect of the disclosure may further extend the first through 25th aspects of the disclosure. In the 26th aspect of the disclosure, the second 3D surface is disconnected from the first 3D surface.

A 27th aspect of the disclosure may further extend the first through 26th aspects of the disclosure. In the 27th aspect of the disclosure, the method further comprises: receiving a plurality of additional intraoral scans; registering the plurality of additional intraoral scans to the one or more additional intraoral scans; updating the second 3D surface based on the plurality of additional intraoral scans; and determining an update to the position and orientation of the second 3D surface relative to the first 3D surface, wherein the update increases an accuracy of the relative position and orientation of the second 3D surface and the first 3D surface.

A 28th aspect of the disclosure may further extend the first through 27th aspects of the disclosure. In the 28th aspect of the disclosure, the method further comprises displaying the first 3D surface in a first region of a display and the second 3D surface in a second region of the display.

In a 29th aspect of the disclosure, a method comprises: receiving a first intraoral scan of a dental site; receiving a first two-dimensional (2D) image of the dental site, wherein the first 2D image is associated with the first intraoral scan; determining a first estimate of a position of the dental site on a dental arch based on the first 2D image; receiving one or more additional intraoral scans of the dental site; receiving one or more additional 2D images of the dental site, each of the one or more additional 2D images associated with one of the one or more additional intraoral scans; determining a second estimate of the position of the dental site on the dental arch based on the first intraoral scan and the one or more additional intraoral scans, wherein the second estimate is more accurate than the first estimate; and outputting for display a depiction of the dental site on the dental arch according to at least one of the first estimate or the second estimate.

A 30th aspect of the disclosure may further extend the 29th aspect of the disclosure. In the 30th aspect of the disclosure, determining the first estimate of the position of the dental site on the dental arch comprises: inputting an input based on the first 2D image into a trained machine learning model, wherein the trained machine learning model outputs the first estimate of the position of the dental site on the dental arch.

A 31st aspect of the disclosure may further extend the 29th or 30th aspect of the disclosure. In the 30th aspect of the disclosure, determining the second estimate of the position of the dental site on the dental arch comprises: generating a three-dimensional (3D) surface based on the first intraoral scan and the one or more additional intraoral scans; and inputting an input based on the 3D surface into a trained machine learning model, wherein the trained machine learning model outputs the second estimate of the position of the dental site on the dental arch.

A 32nd aspect of the disclosure may further extend the 29th through 31st aspects of the disclosure. In the 32nd aspect of the disclosure, the method further comprises: outputting for display a first depiction of the dental site on the dental arch according to the first estimate; and subsequently outputting for display a second depiction of the dental site on the dental arch according to the second estimate.

In a 33rd aspect of the disclosure, a method comprises: receiving a plurality of intraoral scans during an intraoral scanning session; registering the plurality of intraoral scans together based on overlapping features of the plurality of intraoral scans using a first registration algorithm; generating a first three-dimensional (3D) surface based on the plurality of intraoral scans; receiving one or more additional intraoral scans; determining that the one or more additional intraoral scans fail to satisfy one or more registration criteria for registering to at least one of the plurality of intraoral scans or the first 3D surface based on overlapping features of the one or more additional intraoral scans with at least one of the plurality of intraoral scans or the first 3D surface; and registering the one or more additional intraoral scans to at least one of the plurality of intraoral scans or the first 3D surface based on information other than overlapping features of the one or more additional intraoral scans with at least one of the plurality of intraoral scans, the first 3D surface or a previously generated 3D model of the dental site using a second registration algorithm.

In a 34th aspect of the disclosure, a method comprises: receiving a plurality of intraoral scans of a dental site during an intraoral scanning session; registering the plurality of intraoral scans together; generating a three-dimensional (3D) surface of the dental site based on the plurality of intraoral scans, the 3D surface comprising a plurality of regions, wherein each region of the plurality of regions is associated with a distinct subset of the plurality of intraoral scans; determining a plurality of values for the 3D surface, wherein each value is associated with a region of the plurality of regions and is determined based on application of one or more criteria to the subset of the plurality of intraoral scans associated with the region; determining a region of the plurality of regions having a value that fails to satisfy the one or more criteria; and outputting a recommendation to rescan a region of the dental site associated with the region of the 3D surface having the value that fails to satisfy the one or more criteria.

A $35^{th}$ aspect of the disclosure may further extend the $34^{th}$ aspect of the disclosure. In the $35^{th}$ aspect of the disclosure, the one or more criteria comprise at least one of: an overlapping features criterion; an intraoral scanner movement speed criterion; or a data sufficiency criterion.

A $36^{th}$ aspect of the disclosure may further extend the $34^{th}$ or $35^{th}$ aspects of the disclosure. In the $36^{th}$ aspect of the disclosure, a value for a region of the plurality of regions is determined based at least in part on an amount of intraoral scans included in the subset of the plurality of intraoral scans associated with region that failed to satisfy the one or more registration criteria.

In a $37^{th}$ aspect of the disclosure, a method comprises: determining scan quality metric values of one or more intraoral scans performed by a first intraoral scanner operator; comparing the scan quality metric values to one or more scan quality criteria; determining a scan quality criterion of the one or more scan quality criteria that was not satisfied in the one or more intraoral scans; generating a challenge for the first intraoral scanner operator to perform an intraoral scan in which the scan quality criterion is satisfied; and outputting the challenge for the first intraoral scanner operator.

A $38^{th}$ aspect of the disclosure may further extend the $37^{th}$ aspect of the disclosure. In the $38^{th}$ aspect of the disclosure, the method further comprises: determining additional scan quality metric values of a plurality of additional intraoral scans performed by a plurality of additional intraoral scanner operators; determining a first scan quality score for the first intraoral scanner operator based on the scan quality metric values; determining a plurality of additional scan quality scores, wherein a separate scan quality score is generated for each intraoral scanner operator of the plurality of intraoral scanner operators; ranking the first intraoral scanner operator and the plurality of additional intraoral scanner operators based on respective scan quality scores; and outputting a result of the ranking.

In a $39^{th}$ aspect of the disclosure, a method comprises: receiving a plurality of intraoral scans of a dental arch; generating a first three-dimensional (3D) surface of a first portion of the dental arch based on a first subset of the plurality of intraoral scans of the dental arch; generating a second 3D surface of a second portion of the dental arch based on a second subset of the plurality of intraoral scans of the dental arch; performing a first registration operation to determine a first relative position and orientation between the second 3D surface and the first 3D surface, wherein the second 3D surface is disconnected from the first 3D surface; receiving one or more additional intraoral scans of the dental arch; updating the second 3D surface based on the one or more additional intraoral scans; and performing a second registration operation to determine a second relative position and orientation between the second 3D surface and the first 3D surface, wherein the second 3D surface remains disconnected from the first 3D surface, and wherein the second relative position and orientation between the second 3D surface and the first 3D surface is more accurate than the first relative position and orientation between the second 3D surface and the first 3D surface.

A $40^{th}$ aspect of the disclosure may further extend the $39^{th}$ aspect of the disclosure. In the $40^{th}$ aspect of the disclosure, the method further comprises: receiving one or more further intraoral scans of a region of the dental arch between the first portion and the second portion, wherein first features of the one or more further intraoral scans overlap with features of the first 3D surface, and wherein second features of the one or more further intraoral scans overlap with features of the second 3D surface; and performing a third registration operation to determine a third relative position and orientation between the second 3D surface and the first 3D surface, wherein the third relative position and orientation between the second 3D surface and the first 3D surface is more accurate than the second relative position and orientation between the second 3D surface and the first 3D surface.

A $41^{st}$ aspect of the disclosure may further extend the $40^{th}$ aspect of the disclosure. In the $41^{st}$ aspect of the disclosure, the method further comprises: merging the first 3D surface and the second 3D surface based on the one or more further intraoral scans.

A $42^{nd}$ aspect of the disclosure may further extend the $40^{th}$ or $41^{st}$ aspect of the disclosure. In the $40^{th}$ aspect of the disclosure, the method further comprises: determining an active 3D surface from the first 3D surface and the second 3D surface, wherein the active 3D surface is a 3D surface that includes data from a most recently received intraoral scan; displaying the active 3D surface with a first visualization that is different from a second visualization used for any inactive 3D surfaces.

In a $43^{rd}$ aspect of the disclosure, a method comprises: receiving a first plurality of intraoral scans of a first dental arch of a patient during an intraoral scanning session; generating a first three-dimensional (3D) surface of a first portion of the first dental arch of the patient using the first plurality of intraoral scans; receiving a second plurality of intraoral scans of a second dental arch of the patient during the intraoral scanning session; determining that the second plurality of intraoral scans fail to satisfy one or more registration criteria for registering to at least one of the first plurality of intraoral scans or the first 3D surface; and generating a second 3D surface of a first portion of the second dental arch of the patient using the second plurality of intraoral scans without interrupting the intraoral scanning session.

A $44^{th}$ aspect of the disclosure may further extend the $43^{rd}$ aspect of the disclosure. In the $44^{th}$ aspect of the disclosure, the method further comprises: displaying the first 3D surface in a first region of a display and the second 3D surface in a second region of the display.

A $45^{th}$ aspect of the disclosure may further extend the $43^{rd}$ or $44^{th}$ aspect of the disclosure. In the $45^{th}$ aspect of the disclosure, the method further comprises: estimating a relative position and orientation between the second 3D surface and the first 3D surface.

A $46^{th}$ aspect of the disclosure may further extend the $43^{rd}$ through $45^{th}$ aspects of the disclosure. In the $46^{th}$ aspect of the disclosure, the method further comprises: displaying the first 3D surface and the second 3D surface in accordance with the estimated relative position and orientation between the first 3D surface and the second 3D surface.

A 47th aspect of the disclosure may further extend the 43rd through 46th aspects of the disclosure. In the 47th aspect of the disclosure, the first dental arch is a first one of an upper dental arch or a lower dental arch, and the second dental arch is a second one of the upper dental arch or the lower dental arch, the method further comprising: automatically determining, based on processing of the first plurality of intraoral scans, that the first plurality of intraoral scans are of the first dental arch; and automatically determining, based on processing of the second plurality of intraoral scans, that the second plurality of intraoral scans are of the second dental arch.

A 48th aspect of the disclosure may further extend the 47th aspect of the disclosure. In the 48th aspect of the disclosure, processing the first plurality of intraoral scans comprises inputting the first plurality of intraoral scans into a machine learning model that has been trained to classify intraoral scans as being associated with at least one of an upper dental arch role or a lower dental arch role, wherein the machine learning model outputs a first one of the upper dental arch role or the lower dental arch role; and processing the second plurality of intraoral scans comprises inputting the second plurality of intraoral scans into the machine learning model, wherein the machine learning model outputs a second one of the upper dental arch role or the lower dental arch role.

A 49th aspect of the disclosure may further extend the 43rd through 48th aspects of the disclosure. In the 49th aspect of the disclosure, the method further comprises: receiving a third plurality of intraoral scans of the first dental arch or the second dental arch; determining that the third plurality of intraoral scans fail to satisfy the one or more registration criteria for registering to the first 3D surface and fails to satisfy the one or more registration criteria for registering to the second 3D surface; and generating a third 3D surface of a second portion of the upper dental arch or the lower dental arch based on the third plurality of intraoral scans without interrupting the intraoral scanning session.

In a 50th aspect of the disclosure, a method comprises: receiving a plurality of intraoral scans of a dental arch; and automatically generating multiple three-dimensional surfaces of the dental arch without discarding any of the plurality of intraoral scans.

A 51st aspect of the disclosure may further extend the 50th aspect of the disclosure. In the 51st aspect of the disclosure, the method further comprises: determining relative positions and orientations of the multiple three-dimensional surfaces of the dental arch; and displaying the multiple three-dimensional surfaces having the determined relative positions and orientations.

In a 52nd aspect of the disclosure, a computer readable medium (e.g., a non-transitory computer readable medium) includes instructions that, when executed by a processing device, cause the processing device to perform the method of any of the first through 51st aspects of the disclosure.

In a 53rd aspect of the disclosure, a system comprises an intraoral scanner and a computing device, wherein the computing device is configured to perform the method of any of the first through 51st aspects of the disclosure.

BRIEF DESCRIPTION OF THE DRAWINGS

The present disclosure is illustrated by way of example, and not by way of limitation, in the figures of the accompanying drawings.

DETAILED DESCRIPTION

Figure 1:
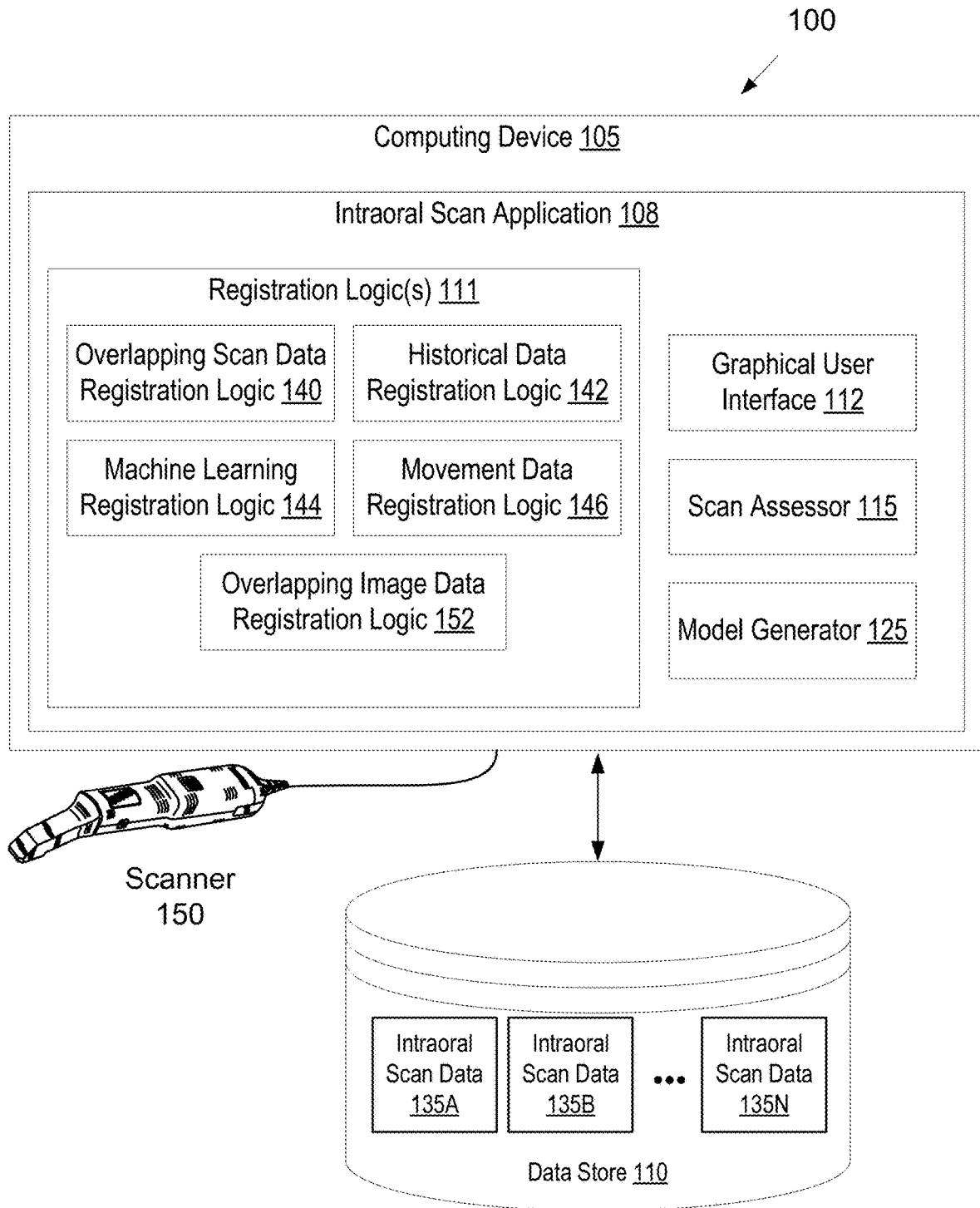
FIG. 1 illustrates one embodiment of a system for performing intraoral scanning and generating a virtual three dimensional model of a dental site.

Described herein is a method and apparatus for improving the ease of performing intraoral scans, such as intraoral scans taken of dental sites for patients. Embodiments may also improve the quality of intraoral scans. Further described herein are an intuitive intraoral scanning process and an intraoral scanning system configured to perform the intuitive intraoral scanning process. The intuitive intraoral scanning process can be performed by an operator who has received little or no training on use of the intraoral scanning system to achieve high quality scan results. The intraoral scanning process is performed in embodiments without any scanning protocol. For example, an operator is not directed to start scanning at a particular region, to scan in a particular direction, to scan an identified second region after a first region, and so on in embodiments. In embodiments, an operator may begin scanning at any region of a patient's oral cavity, may scan along any direction in the intraoral cavity, may skip around between regions of the oral cavity at their discretion, and so on, optionally without constraint. The intraoral scanning system may receive and use the intraoral scan data without dropping scans, regardless of whether intraoral scans successfully register with other intraoral scans at the time of their creation. Moreover, intraoral scans may be generated and stitched together in embodiments to generate 3D surfaces and ultimately to generate 3D models of a patient's dental arches without any need for an operator to input information associated with what is being scanned (e.g., without a need for a user to indicate which dental arch they are scanning, which preparation tooth they are scanning, and so forth), whether or not a 3D model of the patient's dental arch (e.g., a historical template of the dental arch) was previously generated.

Also described herein is a method and apparatus for providing detailed and/or useful feedback on a current scanning session to help guide an operator to improve their scanning technique. As scans are generated, the intraoral scanning system may analyze the generated scans and determine whether an operator is moving an intraoral scanner too fast, whether they are generating scans with too little overlap, whether a window of the scanner is too dirty, whether moving tissue, blood and/or saliva are detected, and so on. In embodiments, a user interface of the intraoral scanning system provides a dashboard on which such information is displayed. In embodiments, the dashboard is hidden until one or more issues are detected that could potentially negatively impact scan quality, at which point the full dashboard may be displayed and/or graphics associated with specific identified issues are displayed. This can help an operator to understand why a current intraoral scanning session may not be going well and/or how to correct their scanning technique during the scanning process.

During a scanning session, a user or operator (e.g., a dental practitioner) of an intraoral scanner may generate multiple different intraoral scans of a dental site, model of a dental site, or other object until enough scans have been taken to generate an accurate model of the dental site (e.g., of an upper and/or lower dental arch). As scans are acquired, these scans are registered with and stitched to previously acquired scans and/or a 3D surface generated based on such previously acquired scans. However, multiple factors may prevent an intraoral scan from registering with and/or stitching to previous intraoral scans and/or a 3D surface generated from such previous intraoral scans. For example, an intraoral scan may have poor data or too little useful data to be used to register the intraoral scan with any previously acquired intraoral scans or a 3D surface based on overlapping data. This may occur, for example, if an operator moves the intraoral scanner too quickly during scanning, if moving tissue obscures a tooth being scanned, if blood and/or saliva obscure the tooth being scanned, if a window, mirror or lens of the intraoral scanner is dirty, and so on. Additionally, the intraoral scan may have too few overlapping regions or features with previously acquired intraoral scans and/or a 3D surface to register with and/or stitch to the previously acquired intraoral scans and/or the 3D surface. Additionally, an operator may move the intraoral scanner too quickly, which can cause distorted scan data that does not register to prior scans and/or a generated 3D surface. Such instances of failure to register a current scan to previous scans readily using overlapping scan data does not pose any problem in embodiments.

Historically, scans that cannot or should not be registered to other scans in the scanning session based on overlapping features of the scans are discarded, leaving the user to rescan the areas not captured. Many systems enter a recovery mode in which an operator is instructed to move the scanner back to a region that was previously captured, at which point new scans can start being generated and registered with the existing scans. This can result in confusion on the part of the operator, lost scan data (as no scan data is being recorded until one of the new scans can register with a generated 3D surface) and a longer scanning session.

In embodiments described herein, such intraoral scans that fail registration with previously generated scans and/or a generated 3D surface are not dropped. Instead, scans that fail registration to previous scans and/or a previously generated 3D surface may be used to generate a new 3D surface. Thus, there may be multiple different 3D surfaces for the same dental arch. As new scans are received, those scans may be registered and/or stitched to one or more 3D surfaces. As enough information is received for a region between two or more 3D surfaces, those two or more 3D surfaces may be joined into a single 3D surface. This can facilitate quick and accurate scan sessions by reducing or eliminating discarded intraoral scans.

In embodiments described herein, an intraoral scan application may periodically or continually determine values of one or more metrics associated with scan quality and/or with an ability to register scans with previous scans and/or 3D surfaces. Examples of such metrics include a speed of scanner movement metric, an angle of incidence metric, a dirty optical surface metric, a distance between scanner head and dental site metric, and so on. Current values for some or all of these metrics may be shown on a dashboard of a graphical user interface. In some embodiments, values for scanning quality metrics are shown when those values approach one or more thresholds that, if exceeded, reduce an ability of the intraoral scan application to register scans to previous scans and/or 3D surfaces. As additional scans are generated and the values of the metrics are updated, a notice or alarm may be generated if any of the metric values fails to satisfy a scanning quality metric criterion (e.g., a scan quality metric threshold). If any of the metric values falls outside of one or more acceptable ranges associated with high quality scans, then the metric values may be shown in the dashboard. If any of the metric values then later falls within the one or more acceptable ranges associated with high quality scans, then the metric values may be removed from the dashboard. Thus, users of the intraoral scanner may automatically be alerted during a scanning session if one or more aspects of their scanning technique would impair a scanning quality and/or an ability to register and stitch together scans. This enables users to adjust their technique in real time during intraoral scanning responsive to indicators on the dashboard, improving an overall quality of the intraoral scanning and potentially shortening scan time and reducing or eliminating a need to rescan portions of a dental arch.

FIG. 1 illustrates one embodiment of a system 100 for performing intraoral scanning and/or generating a virtual three dimensional model of a dental site. In embodiments, system 100 may carry out one or more operations below described with reference to the following figures. System 100 includes a computing device 105 that may be coupled to an intraoral scanner 150 (also referred to as a scanner) and/or a data store 110 via a wired or wireless connection.

In one embodiment, scanner 150 is wirelessly connected to computing device 105 via a direct wireless connection. In one embodiment, scanner 150 is wirelessly connected to computing device 105 via a wireless network. In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, computing device 105 may be physically connected to one or more wireless access points and/or wireless routers (e.g., Wi-Fi access points/routers). Intraoral scanner 150 may include a wireless module such as a Wi-Fi module, and via the wireless module may join the wireless network via the wireless access point/router.

In embodiments, scanner 150 includes an inertial measurement unit (IMU). The IMU may include an accelerometer, a gyroscope, a magnetometer, a pressure sensor and/or other sensor. For example, scanner 150 may include one or more micro-electromechanical system (MEMS) IMU. The IMU may generate inertial measurement data (referred to herein as movement data or motion data), including acceleration data, rotation data, and so on.

Computing device 105 may include a processing device, memory, secondary storage, one or more input devices (e.g., such as a keyboard, mouse, tablet, and so on), one or more output devices (e.g., a display, a printer, etc.), and/or other hardware components. Computing device 105 may be connected to data store 110 either directly or via a network. The network may be a local area network (LAN), a public wide area network (WAN) (e.g., the Internet), a private WAN (e.g., an intranet), or a combination thereof. The computing device 105 may be integrated into the scanner 150 in some embodiments.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

Computing device 105 and/or data store 110 may be located at dental office, at dental lab, or at one or more other locations such as a server farm that provides a cloud computing service. Computing device 105 and/or data store 110 may connect to components that are at a same or a different location from computing device 105 (e.g., components at a second location that is remote from the dental office, such as a server farm that provides a cloud computing service). For example, computing device 105 may be connected to a remote server, where some operations of an intraoral scan application 108 are performed on computing device 105 and some operations of intraoral scan application 108 are performed on the remote server.

Some additional computing devices may be physically connected to the computing device 105 via a wired connection. Some additional computing devices may be wirelessly connected to computing device 105 via a wireless connection, which may be a direct wireless connection or a wireless connection via a wireless network. In embodiments, one or more additional computing devices may be mobile computing devices such as laptops, notebook computers, tablet computers, mobile phones, portable game consoles, and so on. In embodiments, one or more additional computing devices may be traditionally stationary computing devices, such as desktop computers, set top boxes, game consoles, and so on. The additional computing devices may act as thin clients to the computing device 105. In one embodiment, the additional computing devices access computing device 105 using remote desktop protocol (RDP). In one embodiment, the additional computing devices access computing device 105 using virtual network control (VNC). Some additional computing devices may be passive clients that do not have control over computing device 105 and that receive a visualization of a user interface of intraoral scan application 108. In one embodiment, one or more additional computing devices may operate in a master mode and computing device 105 may operate in a slave mode.

Intraoral scanner 150 may include a probe (e.g., a hand held probe) for optically capturing three dimensional structures (e.g., by confocal focusing of an array of light beams). Intraoral scanner 150 may be used to perform intraoral scanning of a patient's oral cavity. An intraoral scan application 108 running on computing device 105 may communicate with the scanner 150 to effectuate the intraoral scanning. A result of the intraoral scanning may be intraoral scan data 135A, 135B through 135N that may include one or more sets of intraoral scans and/or intraoral images (e.g., 2D images, near infrared (NIRI) images, etc.). Each intraoral scan may include a point cloud that may include depth information (e.g., a height map) of a portion of a dental site. One example intraoral scan is a height map, which may be or include an image with depth information. In embodiments, intraoral scans include x, y and z information.

In one embodiment, the intraoral scanner 150 generates numerous discrete (i.e., individual) intraoral scans. In some embodiments, sets of discrete intraoral scans are merged into a smaller set of blended intraoral scans, where each blended scan is a combination of multiple discrete scans. The intraoral scan data 135A-N may include raw scans and/or blended scans, each of which may be referred to as intraoral scans (and in some instances as intraoral images). While scanning, the intraoral scanner may generate multiple (e.g., tens) of scans (e.g., height maps) per second (referred to as raw scans). In order to improve the quality of the data captured, a blending process may be used to combine a sequence of raw scans into a blended scan by some averaging process. Additionally, intraoral scanner 150 may generate many scans per second. This may be too much data to process using a machine learning model in real time. Accordingly, groups of similar scans may be combined into the blended scans, and the blended scans may be input into one or more trained machine learning model. This may vastly reduce the computation resources used to process the intraoral scans without degrading quality. In one embodiment, each blended scan includes data from up to 20 raw scans, and further includes scans that differ by less than a threshold angular difference from one another and/or by less than a threshold positional difference from one another. Accordingly, some blended scans may include data from 20 scans, while other blended scans may include data from fewer than 20 scans. In one embodiment, the intraoral scan (which may be a blended scan) includes height values and intensity values for each pixel in the image.

Intraoral scan data 135A-N may also include color 2D images and/or images of particular wavelengths (e.g., near-infrared (NIRI) images, infrared images, ultraviolet images, etc.) of a dental site in embodiments. In embodiments, intraoral scanner 150 alternates between generation of 3D intraoral scans and one or more types of 2D intraoral images (e.g., color images, NIRI images, etc.) during scanning. For example, one or more 2D color images may be generated between generation of a fourth and fifth intraoral scan. For example, some scanners may include multiple image sensors that generate different 2D color images of different regions of a patient's dental arch concurrently. These 2D color images may be stitched together to form a single color representation of a larger field of view that includes a combination of the fields of view of the multiple image sensors.

The scanner 150 may transmit the intraoral scan data 135A, 135B through 135N to the computing device 105. Computing device 105 may store the intraoral scan data 135A-135N in data store 125.

According to an example, a user (e.g., a practitioner) may subject a patient to intraoral scanning. In doing so, the user may apply scanner 150 to one or more patient intraoral locations. The scanning may be divided into one or more segments (also referred to as roles). As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan data sets, each of which may include 2D intraoral images (e.g., color 2D images) and/or 3D intraoral scans of particular teeth and/or regions of an intraoral site. In one embodiment, separate intraoral scan data sets are created for the maxillary arch, for the mandibular arch, for a patient bite, and/or for each preparation tooth. Alternatively, a single large intraoral scan data set is generated (e.g., for a mandibular and/or maxillary arch). Intraoral scans may be provided from the scanner 150 to the computing device 105 in the form of one or more points (e.g., one or more pixels and/or groups of pixels). For instance, the scanner 150 may provide an intraoral scan as one or more point clouds. The intraoral scans may each comprise height information (e.g., a height map that indicates a depth for each pixel).

The manner in which the oral cavity of a patient is to be scanned may depend on the procedure to be applied thereto. For example, if an upper or lower orthodontic appliance is to be created, then a full scan of the mandibular or maxillary edentulous arches may be performed. In contrast, if a bridge is to be created, then just a portion of a total arch may be scanned which includes an edentulous region, the neighboring abutment teeth and the opposing arch and dentition.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances.

Intraoral scanners may work by moving the scanner 150 inside a patient's mouth to capture all viewpoints of one or more tooth. During scanning, the scanner 150 generates intraoral scans, which may include calculating distances to solid surfaces in some embodiments. These distances may be recorded as images called 'height maps'. Each scan (e.g., optionally height map) is overlapped algorithmically, or 'stitched', with the previous set of scans to generate a growing 3D surface. As such, each scan is associated with a rotation and/or displacement in space, or a projection, to how it fits into the 3D surface.

In one embodiment, intraoral scan application 108 includes one or more registration logic(s) 111, a graphical user interface 112, a scan assessor 115, and a model generator 125. Alternatively, the operations of one or more of the registration logic(s) 111, the graphical user interface 112, the scan assessor 115, or the model generator 125 may be combined into a single module and/or divided into multiple modules.

Registration logic(s) 111 are responsible for registering and/or stitching together intraoral scans received during a scan session. Registration logics 111 may include multiple different logics each of which may apply one or more different registration algorithms or techniques to determine relative positions and orientations of intraoral scans and/or 3D surfaces. In one embodiment, registration logics 111 include an overlapping scan data registration logic 140, a historical data registration logic 142, a machine learning registration logic 144, a movement data registration logic 146, and an overlapping image data registration logic 152.

Performing scan registration may include capturing 3D data of various points of a surface in multiple scans (e.g., views from one or more camera), and registering the scans together and/or to 3D surfaces already generated from multiple intraoral scans by computing transformations between the scans and/or 3D surfaces. This may include determining the relative positions and/or orientations of the different scans and/or 3D surfaces. The scans and/or 3D surfaces may then be integrated into a common reference frame by applying appropriate transformations to points of each registered scan and/or 3D surface. For example, canonical position information (including a canonical position and a canonical orientation) may be determined for each intraoral scan and/or for each 3D surface. The canonical position information may be coordinates in a common reference frame referred to as the canonical reference frame. In one embodiment, the canonical position information includes canonical coordinates that describe the position and orientation of the intraoral scans and/or 3D surfaces in the common reference frame. In one embodiment, the canonical position information includes a position and/or orientation relative to a reference jaw. For example, canonical position information may include a direction relative to vertical and/or a displacement along an arch having a set length and width. Canonical position information may be scaled based on sizes of scanned teeth and/or jaw segments. For example, processing logic may estimate teeth size and create canonical coordinates for a jaw sized appropriately for the estimated teeth size. This may include determining an estimated arch width and/or arch length based on the determined teeth size. Generated 3D surfaces may then be assigned canonical coordinates based on a rough registration to the reference jaw.

Registration logic(s) 111 may repeat registration for all intraoral scans of a sequence of intraoral scans to obtain transformations for each intraoral scan, to register each intraoral scan with previous intraoral scan(s), with generated 3D surface(s), and/or with a common reference frame. Registration logic(s) 111 may integrate intraoral scans into a single virtual 3D surface and/or into multiple 3D surfaces by applying the appropriate determined transformations to each of the intraoral scans. Each transformation may include rotations about one to three axes and translations within one to three planes. Additionally, registration logic(s) 111 may register intraoral scans to other intraoral scans and/or 3D surface(s) even in the absence of any overlapping scan data and/or insufficient overlapping scan data with other intraoral scans and/or 3D surface(s). Such registration to scans and/or 3D surfaces with no or insufficient overlapping scan data may be performed even in the absence of any particular scanning protocol. Accordingly, a user may start scanning at any location in a patient's mouth, scan in any direction, start and stop in any manner, skip scanning of any regions of the patient's mouth, and so on, and the registration logic(s) 111 will still register the intraoral scans together and will not drop intraoral scans.

In one embodiment, the intraoral scans and/or 3D surfaces may be registered together in real time, during the current scan session. As intraoral scans are registered together, their combined data may be used to generate and/or update a 3D surface. One or more 3D surfaces may be generated based on the registered and stitched together intraoral scans during the intraoral scanning. The one or more 3D surfaces may be output to a display during intraoral scanning so that a doctor or technician can view their scan progress thus far. As each new intraoral scan is captured and registered to previous intraoral scans and/or a 3D surface, the one or more 3D surfaces may be updated, and the updated 3D surface(s) may be output to the display. In embodiments, separate 3D surfaces are generated for the upper jaw and the lower jaw. Additionally, as set forth in detail below, multiple different 3D surfaces may be generated for the same dental site (e.g., for the same dental arch). This process may be performed in real time or near-real time to provide an updated view of the captured 3D surfaces during the intraoral scanning process. When multiple 3D surfaces of the same dental arch are generated, different visualizations (e.g., different colors, different fill patterns, different levels of transparency, etc.) may be used to display a currently active 3D surface (a 3D surface that includes data from a most recently received intraoral scan) than is used to display other 3D surfaces. Accordingly, even if two 3D surfaces overlap, a user may still see that the two 3D surfaces are in fact distinct 3D surfaces and not a single 3D surface. This may inform the user that further scans should be acquired for the region at the interface between the two 3D surfaces. Other visualization techniques may additionally or alternatively be used to enable a user to distinguish between overlapping 3D surfaces. For example, a line or spacing at the interface of the two 3D surfaces may be shown to indicate that they are distinct 3D surfaces.

In one embodiment, as each new intraoral scan is received, overlapping scan data registration logic 140 compares that new intraoral scan to some or all previous intraoral scans received during a current scan session and/or to one or more previously generated 3D surface generated during the current intraoral scanning session. In one embodiment, registration is performed using blended scans. If there is sufficient overlap between the current intraoral scan and one or more of the previous intraoral scans (or one or more determined 3D surface), then the current intraoral scan may be registered with those one or more previous intraoral scans and/or 3D surface(s) and stitched to those one or more previous intraoral scans and/or 3D surfaces. First registration algorithms may be carried out by overlapping data registration logic 140 to register intraoral scans having overlapping scan data, which essentially involves determination of the transformations which align one intraoral scan with another intraoral scan (or with a 3D surface). Scan registration may involve identifying multiple points in each intraoral scan and/or 3D surface (e.g., point clouds) of a pair of intraoral scans (or a scan and a 3D surface, or a pair of 3D surfaces), surface fitting to the points of each intraoral scan (or a scan and a 3D surface, or a pair of 3D surfaces), and using local searches around points to match points of the two adjacent intraoral scans (or a scan and a 3D surface, or a pair of 3D surfaces). For example, overlapping scan data registration logic 140 may match points of one intraoral scan with the closest points interpolated on the surface of the other intraoral scan, and iteratively minimize the distance between matched points. Overlapping scan data registration logic 140 may also find the best match of curvature features, spin-image point features, edges, and so on at points of one intraoral scan with curvature features, spin-image point features, edges, and so on at points interpolated on the surface of the other intraoral scan, with or without iteration. Other techniques that may be used for registration include those based on determining point-to-point correspondences using other features and minimization of point-to-surface distances, for example. Other registration techniques that rely on overlapping scan data between scans and/or 3D surfaces may also be used by overlapping data registration logic 140.

In some instances, a received intraoral scan may not be registerable with any other intraoral scan from a current scan session using the one or more first intraoral scan registration algorithms that operate based on overlapping scan data. For example, a user may generate a first set of intraoral scans of a left side of a patients lower jaw, may remove the scanner from the patient's mouth, and may then reinsert the scanner into the patient's mouth and scan the right side of the patient's lower jaw without having scanned the middle of the patient's lower jaw. In another example, a user may move the scanner too quickly during scanning such that scans are blurred or lack sufficient overlap for registration based on overlapping scan data. In another example, an optical surface (e.g., a window or mirror) of the intraoral scanner may be dirty, obscuring enough of an intraoral scan that it lacks sufficient data to register to previously generated intraoral scans. In another example, moving tissue (e.g., a tongue), blood and/or saliva may obscure some portion of the intraoral scan, such that it lacks sufficient data to register to existing scans using overlapping data registration logic 140. Other issues may also prevent the registration of intraoral scans to other intraoral scans and/or a 3D surface during intraoral scanning by overlapping scan data registration logic 140. In traditional systems such intraoral scans that fail to register to any other intraoral scans or to a 3D surface using overlapping scan data would be discarded, and a user would be asked to rescan one or more areas. Embodiments of the present disclosure enable such intraoral scans that do not register to other intraoral scans or a 3D surface using overlapping scan data to be registered using other techniques, such as by applying the intraoral scans to a trained machine learning model that has been trained to output canonical position information (e.g., position and/or orientation in a common reference frame or on a reference jaw) of a 3D surface or an intraoral scan. One or more registration logics 111 (e.g., historical data registration logic 142, machine learning registration logic 144, movement data registration logic 146 and/or overlapping image data registration logic 152) may estimate a rough relative position and orientation of an intraoral scan to one or more already generated 3D surface to perform a rough registration in the absence of sufficient overlapping scan data. The relative position and orientation may be estimated even though there is insufficient overlapping scan data between the intraoral scan(s) and/or 3D surface(s) to directly register them using overlapping scan data registration logic 140.

When an intraoral scan fails to register to any other intraoral scan or to a 3D surface generated from one or more intraoral scans using the first registration algorithm(s) applied by overlapping scan data registration logic 140 that operate based on overlapping scan data, registration logic(s) 111 (e.g., historical data registration logic 142, machine learning registration logic 144, movement data registration logic 146, overlapping image data registration logic 152) may attempt to register the intraoral scan to other intraoral scans and/or 3D surfaces using one or more additional (second) registration algorithms. The one or more additional registration algorithms do not rely on overlapping scan data between intraoral scans and/or 3D surfaces to perform registration. Instead, the additional registration algorithms use other information to perform registration and/or to determine relative positions and/or orientations between intraoral scans and/or 3D surfaces. Such relative positions and orientations determined by the other registration logics 111 may be estimates that are not as accurate as relative positions and orientations determined by overlapping scan data registration logic 140. However, these estimates may be accurate enough to enable scans to be kept and used to generate additional 3D surfaces, which may later be stitched together to ultimately generate a single 3D surface of a dental arch. This makes scanning much more intuitive, quicker and easier to perform, as scanning protocols may be omitted and a user may scan a dental site in any manner they desire without loss of accuracy or efficiency.

In one embodiment, overlapping image data registration logic 152 uses overlapping 2D images to register an intraoral scan to a 3D surface or other intraoral scan. Scanner 150 may alternate between generation of intraoral scans (which contain 3D information) and one or more types of 2D intraoral images. Each of the intraoral scans may therefore be associated with one or more 2D images generated close in time to when the intraoral scans were generated. The 2D images may contain more dense data (e.g., data for more points of a dental site) than a single intraoral scan. Accordingly, even if an intraoral scan fails to register to a 3D surface or other intraoral scan based on overlapping scan data, the 2D image associated with that intraoral scan may be registrable with another 2D image associated with the 3D surface or earlier intraoral scan. Such registration may be performed in a similar manner to how registration is performed using overlapping scan data, but is inherently less accurate in three dimensions since it contains only two dimensional data. However, registration using 2D images provides a sufficient estimate of the relative position and orientation of an intraoral scan to a 3D surface to provide useful information to a user.

In embodiments, timing of when intraoral scans and when 2D images were generated may be taken into consideration when estimating the relative position and orientation of 3D scans based on 2D images. A trajectory may be determined using one or more 3D scans generated before a 2D image was generated and one or more 3D scans generated after the 2D image was generated. The trajectory may then be used to interpolate a position and orientation of the 2D image relative to the positions and orientations of the 3D surfaces. The interpolated position and orientation of the 2D image may then be used for registration.

In one embodiment, historical data registration logic 142 uses historical scan data (e.g., 3D models and/or 3D surfaces generated from previous intraoral scans that were generated either earlier in a current patient visit or in a previous patient visit) to determine a relative position and orientation of an intraoral scan to a 3D surface or to determine a relative position and orientation of a second 3D surface to a first 3D surface, where both 3D surfaces represent different regions of a same dental arch. Historical data registration logic 142 may determine whether historical scans exist for a particular patient and register intraoral scans and/or 3D surfaces of a current scan session to a 3D model generated based on those historical intraoral scans based on overlapping data from the current intraoral scans and/or 3D surfaces and the historical scan data (e.g., the 3D model generated from the historical intraoral scans). The historical scan data of the patient may have been generated during past visits of the patient or may have been generated during a current patient visit before dental work was performed. For example, a doctor may scan a patient's oral cavity to generate a pre-scan 3D model of the patient's oral cavity prior to performing one or more restorative operations, such as grinding a tooth to form a preparation, pulling a tooth, inserting an implant, and so on. Then the doctor may then perform intraoral scanning again during and/or after the one or more restorative operations. The intraoral scans generated during such subsequent intraoral scanning may be registered to each other based on registration to the pre-scan 3D model by historical data registration logic 142 if overlapping data registration logic fails to register them.

In one embodiment, movement data registration logic 146 uses movement data to perform registration. Even if there is insufficient overlapping data between two intraoral scans (or between an intraoral scan and a 3D surface), movement data may indicate how much an intraoral scanner moved and/or rotated between generation of a current intraoral scan and a previous intraoral scan. This movement data may be used to determine a position and orientation of the new intraoral scan relative to the position and orientation of the previously generated intraoral scan (or 3D surface to which the previously generated intraoral scan was stitched).

In one embodiment, movement data is generated by an inertial measurement unit (IMU) of the intraoral scanner. The IMU may generate inertial measurement data, including acceleration data, rotation data, and so on. The inertial measurement data may identify changes in position in up to three dimensions (e.g., along three axes) and/or changes in orientation or rotation about up to three axes. The movement data from the IMU may be used to perform dead reckoning of the scanner 150. Use of data from the IMU for registration may suffer from accumulated error and drift, and so may be most applicable for scans generated close in time to one another. In embodiments, movement data from the IMU is particularly accurate for detecting rotations of the scanner 150. Data from the IMU may not take into account a patient's head motions, which would affect a relative position and orientation of 3D scans even in the absence of any movement of the scanner 150. In embodiments patient motions are identified accounted for in estimating relative positions and orientations between 3D scans, as set forth in FIGS. 7B-7C below.

In one embodiment, movement data is generated by extrapolating changes in position and orientation (e.g., current motion) based on recent intraoral scans that successfully registered together by overlapping scan data registration logic 140. Movement data registration logic 146 may compare multiple intraoral images (e.g., 2D intraoral images) and/or 3D surfaces and determine a distance between a same point or sets of points that are represented in each of the multiple intraoral images and/or scans. For example, movement data may be generated based on the transformations performed to register and stitch together multiple intraoral scans. Movement data registration logic 146 may determine times at which each of the images and/or scans was generated and the distances between the features in the images and/or scans to determine a rate of change of the distances between the features (e.g., a speed of the intraoral scanner between scans). This information may be used to estimate a motion of the scanner, which may be applied to new scans to estimate a relative position and orientation of the scanner at the time that the new scans were generated. In one embodiment, movement data registration logic 146 may determine times at which each of the images and/or scans was generated and the transformations between scans to determine a rate of rotation and/or movement between scans. When a new intraoral scan is generated that does not register to a previously generated intraoral scan or to a 3D surface by overlapping scan data registration logic 140, movement data registration logic 146 may determine a time at which the new scan was generated and extrapolate the estimated movement (e.g., rate of change of distance, or determined rate of rotation and/or movement) and last known position of the scanner to determine a position and/or orientation of the features and/or dental site represented in the new intraoral scan. In embodiments, movement data determined based on intraoral scans and/or 2D images is particularly accurate for translations.

In one embodiment, intraoral scanner 150 includes multiple cameras that are at different angles to one another. In such instances, the images and/or scans generated by the multiple cameras are usable to compute movement data for up to six degrees of freedom (e.g., rotation about three axes and translations along three axes). For example, in one embodiment intraoral scanner 150 corresponds to the intraoral scanner described in U.S. application Ser. No. 16/910,042, filed Jun. 23, 2020 and entitled "Intraoral 3D Scanner Employing Multiple Miniature Cameras and Multiple Miniature Pattern Projectors", which is incorporated by reference herein. In one embodiment, intraoral scanner 150 corresponds to the intraoral scanner described in U.S. application Ser. No. 16/446,181, filed Jun. 19, 2019 and entitled "Intraoral 3D Scanner Employing Multiple Miniature Cameras and Multiple Miniature Pattern Projectors", which is incorporated by reference herein.

In one embodiment, machine learning registration logic 144 uses one or more trained machine learning model to perform registration (e.g., to determine relative positions and orientations of intraoral scans and/or 3D surfaces). Data from intraoral scan(s) and/or 3D surface(s) may be input into the trained machine learning model, which may then generate an output indicating canonical position and orientation for the intraoral scan(s) and/or 3D surface(s) and/or relative position and orientation of intraoral scans and/or 3D surfaces. The data may be 3D data (e.g., 3D surfaces) and/or 2D data (e.g., projections of a 3D surface onto one or more planes). For example, one or more height maps may be input into the machine learning model. In addition to intraoral scan data and/or 3D surface data, other information such as 2D intraoral images (e.g., 2D color images), movement data (e.g., from an inertial measurement unit (IMU)), and/or other data may be input into the machine learning model along with the scan data. In some embodiments, 2D images are input into the trained machine learning model instead of intraoral scans. In one embodiment, the intraoral scanner includes multiple cameras that may have different positions and orientations relative to one another on a probe of the intraoral scanner. For example, the intraoral scanner may include six cameras. Each camera may have a different field of view and may have a different angle than the other cameras. In one embodiment, the 2D images from each of these cameras may together be input into the trained machine learning model. In an example, a set of 2D images may all be generated at a same time, and may be associated with a particular intraoral scan. The set of 2D images may be input into a trained machine learning model to determine canonical coordinates of the 2D images and the associated intraoral scan.

In one embodiment, a single 3D surface or intraoral scan (and/or one or more 2D images associated with the 3D surface or intraoral scan) may be input into the trained machine learning model, which may output canonical coordinates (e.g., representing position and orientation) for the 3D surface or intraoral scan. In one embodiment, the trained machine learning model outputs canonical coordinates for each point on the intraoral scan or 3D surface. In one embodiment, data for multiple intraoral scans (and/or one or more 2D images associated with each of the intraoral scans) is input into the trained machine learning mode, which may output relative position and orientation of the objects in each of the intraoral scans. The relative position and orientation may or may not be output as canonical position and orientation for each of the scans. In one embodiment, data for one or more intraoral scans and data for a 3D surface are input into the trained machine learning model, which may output position and orientation of the objects in the one or more intraoral scans relative to the position and orientation of the 3D surface. The relative position and orientation may be output as canonical position and orientation for each of the scan(s) and the 3D surface. In one embodiment, data for multiple 3D surfaces is input into the trained machine learning mode, which may output position and orientation of the first 3D surface relative to the position and orientation of the second 3D surface. In some embodiments, the trained machine learning model outputs position and/or orientation data for the intraoral scanner that generated an input 3D scan (e.g., an angle of the intraoral scanner at the time that the intraoral scan was generated). The relative position and orientation may be output as canonical position and orientation for each of the 3D surfaces. Any of the aforementioned data that is input into the trained machine learning model may be accompanied by additional data such as 2D intraoral images (e.g., 2D color images), movement data (e.g., from an inertial measurement unit (IMU)), and/or other data.

As more intraoral scans are generated and are registered to a 3D surface, the information for that 3D surface increases. Information for the updated 3D surface may be input into the trained machine learning model, which may output updated position and orientation information (e.g., updated canonical coordinates), which may be more accurate than previously output position and orientation information. Data from intraoral scans and/or 3D surfaces may be periodically or continuously input into the trained machine learning model, which outputs updated position and orientation information with increasing accuracy.

Scan assessor 115 is responsible for assessing a quality of intraoral scans and/or of regions of 3D surfaces generated from intraoral scans. Scan assessor 115 may additionally or alternatively determine values of one or more scanning metrics during scanning, where the scanning metrics are associated with scan quality and/or 3D surface quality. Examples of scan quality metrics include scan speed, scan distance, scanner cleanliness (or dirtiness), amount of moving tissue, amount of blood and/or saliva, scan angle, voids, data density, and so on.

During intraoral scanning, scan assessor 115 may determine values for multiple different scan quality metrics. Each of the scan quality metric values may be compared to respective scan quality criteria. Examples of scan quality criteria include an overlapping features criterion, an intraoral scanner movement speed criterion, and a data sufficiency criterion. If any of the scan quality metric values approach or fall outside of the scan quality criteria, then one or more indicators (e.g., warnings) may be output to a user via graphical user interface 112. For example, a scanning speed (speed at which scanner probe is moved during scanning) may be computed and compared to a scan speed threshold. If the scan speed is approaching an upper scan speed threshold, then scan speed values may be output to the GUI to notify a user that they are close to moving the scanner too quickly. If the scan speed exceeds the scan speed threshold, then the scan speed visualization may change (e.g., from orange to red) and/or an additional indicator may be displayed. Similarly, if a scanner is moved too slowly (e.g., is slower than a lower scan speed threshold), then the scan speed values may be shown on the GUI to show that they can scan faster. Similarly, other scan quality metric values may be shown on the GUI, either all the time or when they approach one or more scan quality thresholds. In one embodiment, a dashboard may be shown in the GUI that shows values of multiple different scan quality metrics.

Scan assessor 115 may identify areas of interest (AOIs) from intraoral scan data (e.g., intraoral images) and/or 3D surfaces generated from intraoral scan data. In one embodiment, areas of interest are determined by analyzing 3D surfaces to identify voids (e.g., areas for which scan data is missing or for which density of data for a surface is below a threshold, resulting in a failure to satisfy a data sufficiency criterion), areas of conflict or flawed scan data (e.g., areas for which overlapping surfaces of multiple intraoral images fail to match, areas having blurriness, areas of unclear gum line, areas of unclear patient bite, areas of unclear margin line of one or more preparation teeth, areas having scan quality metric values below thresholds, and so forth). An identified void may be a void in a 3D surface or an area of a 3D surface with too few data points. Examples of surface conflict include double incisor edge and/or other physiologically unlikely tooth edge, and/or bite line shift. Flawed scan data may be regions of a 3D surface associated with scan quality metrics or scores that fail to satisfy one or more scan quality criteria (e.g., that are below one or more scan quality threshold). For example, flawed scan data may be identified for a region of a 3D surface that was generated while an optical surface of the intraoral scanner was dirty, while a tooth was covered by blood or saliva, while a tooth was obscured by moving tissue, while the scanner was moving too fast, while the scanner had an improper angle relative to the tooth it was scanning, while the scanner was too close or too far from the tooth that it was scanning, and so on. Areas of insufficient scan data other than voids may also be identified, which may include areas lacking at least a threshold density of data points, or areas associated with less than a threshold number of intraoral scans. Identifying of areas of interest concerning missing and/or flawed scan data may involve the scan assessor 115 performing direct analysis, for instance determining one or more pixels or other points to be missing from patient scan data and/or one or more virtual 3D surfaces. Identifying of areas of interest may additionally or alternatively be performed by determining values of one or more scan quality metrics for each region of a 3D surface, and determining which of those regions have scan quality metric values that fail to satisfy scan quality criteria. In some embodiments, scan data is input into one or more trained machine learning models which outputs one or more scan quality values, or an output usable to determine one or more scan quality metric values and/or scan quality scores.

Scan assessor 115 may determine how to present and/or call out the identified areas of interest. Scan assessor 115 may provide indications or indicators regarding areas of interest as those areas are identified during scanning and/or after scanning is complete (e.g., on a 3D model of a dental arch generated after scanning is complete). Therefore, areas of interest may be determined, and indicators of the areas of interest may be provided, during and/or after an intraoral scan session. Such indications may be provided prior to and/or without construction of an intraoral virtual 3D model. Alternatively, indications may be provided after construction of an intraoral virtual 3D model of a dental site. The indications may be presented (e.g., via a graphical user interface 112) to a user (e.g., a doctor) in connection with and/or apart from one or more depictions of teeth and/or gingivae of a patient. Indication presentation in connection with depictions of patient teeth and/or gingivae may involve the indications being placed so as to correlate an indication with the corresponding portion of the teeth and/or gingivae. The indications may be provided in the form of flags, markings, contours, text, images, and/or sounds (e.g., in the form of speech). Such a contour may be placed (e.g., via contour fitting) so as to follow an extant tooth contour and/or gingival contour. As an illustration, a contour corresponding to flawed scan data indication may be placed so as to follow a contour of the teeth and/or gingiva that were generated using flawed scan data. In placing indications (e.g., flags) the scan assessor 115 may or may not take into account factors such as available lighting, available angle, available zoom, available axes of rotation, and/or other factors corresponding to user viewing of the teeth and/or gingiva depiction (e.g., the virtual 3D model or 3D surface), and may seek indication (e.g., flag) placement which seeks to optimize user viewing in view of these factors). Scan assessor 115 may key the indications (e.g., via color, symbol, icon, size, text, and/or number). The keying of an indication may serve to convey information about that indication. The conveyed information may include classification of an AOI, a size of an AOI and/or an importance rank of an AOI. Accordingly, different flags or indicators may be used to identify different types of AOIs. Scan assessor 115 may determine a classification, size and/or importance rank of an AOI, and may then determine a color, symbol, icon, text, etc. for an indicator of that AOI based on the classification, size and/or importance rank. In embodiments, importance of an AOI may be determined based on one or more scan quality metric values associated with the AOI.

When a scan session is complete (e.g., all intraoral scans for a dental site have been captured), model generator 125 may generate a virtual 3D model of the scanned dental site. Model generator 125 may integrate some or all intraoral scans into a single virtual 3D model by applying the appropriate determined transformations to each of the intraoral scans (e.g., that place the intraoral scans in a common reference frame according to canonical coordinates). The 3D model may additionally include indicators showing regions of the 3D model that contain AOIs, such as regions of the 3D model having voids and/or regions of the 3D model associated with flawed scan data.

Graphical user interface (GUI) 112 is a user interface of intraoral scan application 108 that shows graphical information associated with intraoral scanning. The GUI 112 may display one or more 3D surface generated during scanning based on received intraoral scans. As new intraoral scans are received, those intraoral scans may be stitched to a 3D surface (or multiple 3D surfaces), and a view of the 3D surface(s) may be updated in the GUI. A region of the 3D surface generated based on a most recent intraoral scan may be shown with a first visualization that may be different from a visualization used for regions of the 3D surface generated from previously generated intraoral scans. For example, a different color may be used to represent the region of the 3D surface generated from the most recent intraoral scan than is used for a remainder of the 3D surface. The GUI 112 may also display a dashboard with one or more current scan quality metric values. The GUI 112 may also display, for example, a viewfinder image (e.g., a color 2D image of a view of the scanner), which may enable a user to determine where the probe of the scanner 150 is placed in a user's mouth.

Figure 2:
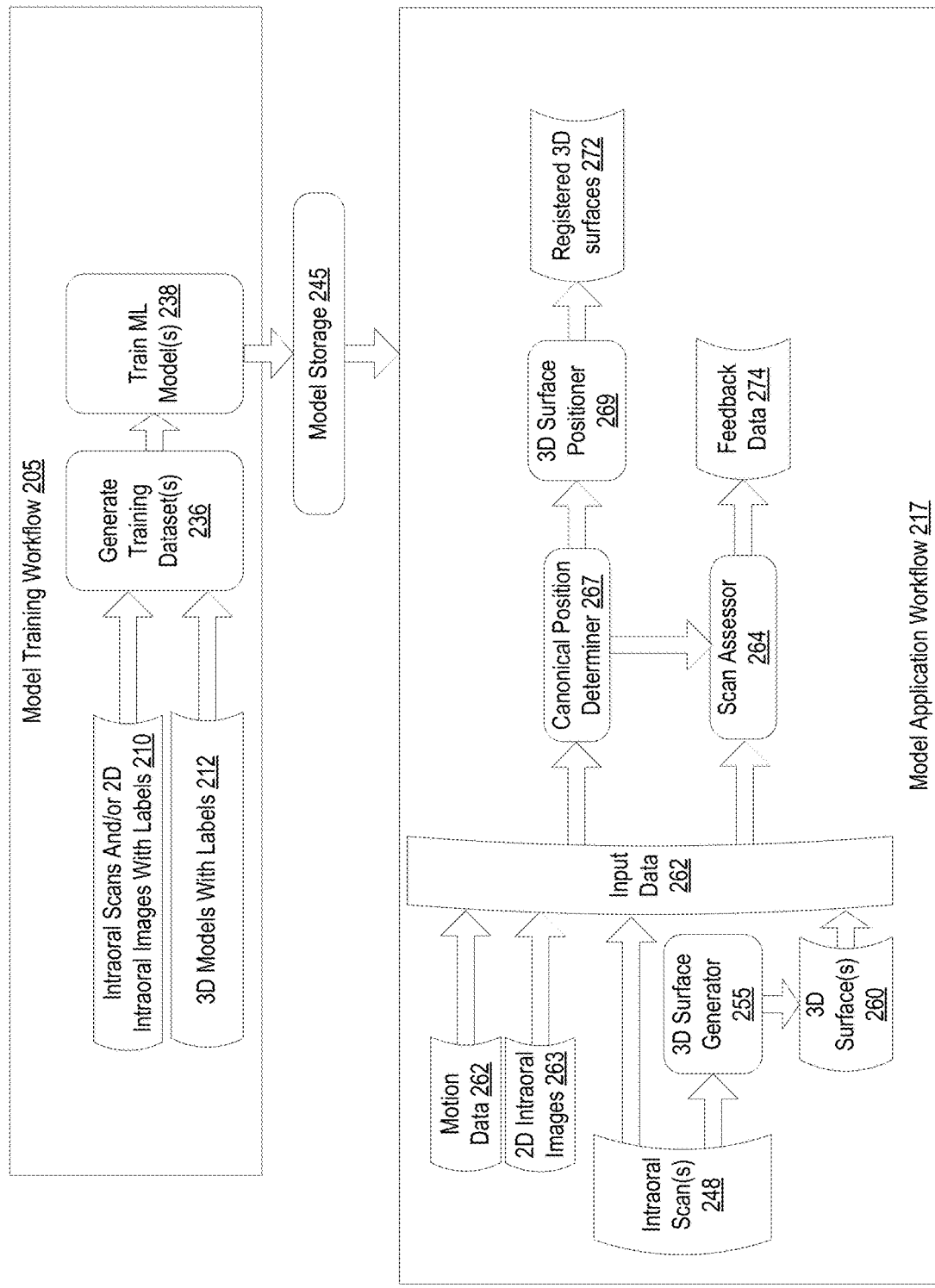
FIG. 2 illustrates a model training workflow and a model application workflow for an intraoral scanning application, in accordance with an embodiment of the present disclosure.

FIG. 2 illustrates a model training workflow 205 and a model application workflow 217 for an intraoral scanning application, in accordance with an embodiment of the present disclosure. In embodiments, the model training workflow 205 may be performed at a server which may or may not include an intraoral scan application, and the trained models are provided to an intraoral scan application (e.g., on computing device 105 of FIG. 1), which may perform the model application workflow 217. The model training workflow 205 and the model application workflow 217 may be performed by processing logic executed by a processor of a computing device. One or more of these workflows 205, 217 may be implemented, for example, by one or more machine learning modules implemented in an intraoral scan application 115 or other software and/or firmware executing on a processing device of computing device 1500 shown in FIG. 15.

The model training workflow 205 is to train one or more machine learning models (e.g., deep learning models) to perform one or more classifying, segmenting, detection, recognition, prediction, etc. tasks for intraoral scan data (e.g., 3D scans, height maps, 2D color images, NIRI images, etc.) and/or 3D surfaces generated based on intraoral scan data. The model application workflow 217 is to apply the one or more trained machine learning models to perform the classifying, segmenting, detection, recognition, prediction, etc. tasks for intraoral scan data (e.g., 3D scans, height maps, 2D color images, NIRI images, etc.) and/or 3D surfaces generated based on intraoral scan data. One or more of the machine learning models may receive and process 3D data (e.g., 3D point clouds, 3D surfaces, portions of 3D models, etc.). One or more of the machine learning models may receive and process 2D data (e.g., 2D images, height maps, projections of 3D surfaces onto planes, etc.).

Many different machine learning outputs are described herein. Particular numbers and arrangements of machine learning models are described and shown. However, it should be understood that the number and type of machine learning models that are used and the arrangement of such machine learning models can be modified to achieve the same or similar end results. Accordingly, the arrangements of machine learning models that are described and shown are merely examples and should not be construed as limiting.

In embodiments, one or more machine learning models are trained to perform one or more of the below tasks. Each task may be performed by a separate machine learning model. Alternatively, a single machine learning model may perform each of the tasks or a subset of the tasks. Additionally, or alternatively, different machine learning models may be trained to perform different combinations of the tasks. In an example, one or a few machine learning models may be trained, where the trained ML model is a single shared neural network that has multiple shared layers and multiple higher level distinct output layers, where each of the output layers outputs a different prediction, classification, identification, etc. The tasks that the one or more trained machine learning models may be trained to perform are as follows:

I) Canonical position determination—this can include determining canonical position and/or orientation of a 3D surface or of objects in an intraoral scan.

II) Scan registration—this may include registering two intraoral scans together and/or registering an intraoral scan to a 3D surface and/or registering two 3D surfaces together using a machine learning model. For example, this may include determining relative position and/or orientation between two intraoral scans, between an intraoral scan and a 3D surface, or between two 3D surfaces that represent different portions of a same dental arch.

III) Scan assessment—this can include determining scan quality metric values associated with intraoral scans and/or regions of 3D surfaces. This can include assigning a quality value to individual scans, 3D surfaces, portions of 3D surface, 3D models, portions of 3D models, etc. Quality values above a threshold may be determined to be a scanning success. This can also include assigning quality values to portions or regions of 3D surfaces or 3D models. Portions or regions with quality values that are below a threshold may be flagged for rescanning.

IV) Blood/saliva determination—this can include performing point-level classification (e.g., pixel-level classification or voxel-level classification) to identify those points/patches classified as blood/saliva and those points/patches not classified as blood/saliva.

V) Dirty optical surface detection—this can include classifying an intraoral scanner or protective sleeve/attachment as dirty based on one or more intraoral scans. Additionally, this can include performing pixel-level or patch-level classification of regions of a scan as dirty and/or can include determining which portions of a scanner are dirty (e.g., a window of a protective sleeve, a window of a scanner head, a lens, a folding mirror, etc.).

VI) Moving tissue (excess tissue) identification/removal—this can include performing pixel-level identification/classification of moving tissue (e.g., tongue, finger, lips, etc.) from intraoral scans and optionally removing such moving tissue from intraoral scans. Moving tissue identification and removal is described in US Publication No. 2020/0349698, entitled "Excessive material removal using machine learning," which is incorporated by reference herein.

VII) Scanning role classification—this can include classifying intraoral scans, sets of intraoral scans, 3D surfaces generated from multiple intraoral scans, 3D models generated from multiple intraoral scans, etc. as associated with an upper jaw role (also referred to as upper dental arch role), a lower jaw role (also referred to as lower dental arch role), or a bite role.

Note that for any of the above identified tasks associated with intraoral scans/3D surfaces/3D models, though they are described as being performed based on an input of intraoral scans, 3D surface and/or 3D models, it should be understood that these tasks may also be performed based on 2D images such as color images, NIRI images, and so on. Additionally, any of the above identified tasks may also receive additional inputs of, for example, 2D images and/or movement data. Any of these tasks may be performed using ML models with multiple input layers or channels, where a first layer may include an intraoral scan/3D surface (or projection of a 3D surface)/3D model (or projection of a 3D model), a second layer may include a 2D color image, a third layer may include a 2D NIRI image, a forth layer may include movement data from an IMU, a fifth layer may include movement data as calculated from intraoral scans and/or 2D images, and so on. In another example, a first layer or channel may include a first 3D scan, a second layer or channel may include a second 3D scan, and so on. In another example, some layers may be for scans and/or 2D images associated with a first 3D surface or intraoral scan and other layers may be for scans and/or 2D images associated with a second 3D surface or intraoral scan.

One type of machine learning model that may be used to perform some or all of the above asks is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize a scanning role. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

In one embodiment, a graph neural network (GNN) architecture is used that operates on three-dimensional data. Unlike a traditional neural network that operates on two-dimensional data, the GNN may receive three-dimensional data (e.g., 3D surfaces) as inputs, and may output predictions, estimates, classifications, etc. based on the three-dimensional data.

In one embodiment, a U-net architecture is used for one or more machine learning model. A U-net is a type of deep neural network that combines an encoder and decoder together, with appropriate concatenations between them, to capture both local and global features. The encoder is a series of convolutional layers that increase the number of channels while reducing the height and width when processing from inputs to outputs, while the decoder increases the height and width and reduces the number of channels. Layers from the encoder with the same image height and width may be concatenated with outputs from the decoder. Any or all of the convolutional layers from encoder and decoder may use traditional or depth-wise separable convolutions.

In one embodiment, one or more machine learning model is a recurrent neural network (RNN). An RNN is a type of neural network that includes a memory to enable the neural network to capture temporal dependencies. An RNN is able to learn input-output mappings that depend on both a current input and past inputs. The RNN will address past and future scans and make predictions based on this continuous scanning information. RNNs may be trained using a training dataset to generate a fixed number of outputs (e.g., to classify time varying data such as video data as belonging to a fixed number of classes). One type of RNN that may be used is a long short term memory (LSTM) neural network.

A common architecture for such tasks is LSTM (Long Short Term Memory). Unfortunately, LSTM is not well suited for images since it does not capture spatial information as well as convolutional networks do. For this purpose, one can utilize ConvLSTM—a variant of LSTM containing a convolution operation inside the LSTM cell. ConvLSTM is a variant of LSTM (Long Short-Term Memory) containing a convolution operation inside the LSTM cell. ConvLSTM replaces matrix multiplication with a convolution operation at each gate in the LSTM cell. By doing so, it captures underlying spatial features by convolution operations in multiple-dimensional data. The main difference between ConvLSTM and LSTM is the number of input dimensions. As LSTM input data is one-dimensional, it is not suitable for spatial sequence data such as video, satellite, radar image data set. ConvLSTM is designed for 3-D data as its input. In one embodiment, a CNN-LSTM machine learning model is used. A CNN-LSTM is an integration of a CNN (Convolutional layers) with an LSTM. First, the CNN part of the model processes the data and a one-dimensional result feeds an LSTM model.

In one embodiment, a class of machine learning model called a MobileNet is used for one or more neural networks. A MobileNet is an efficient machine learning model based on a streamlined architecture that uses depth-wise separable convolutions to build light weight deep neural networks. MobileNets may be convolutional neural networks (CNNs) that may perform convolutions in both the spatial and channel domains. A MobileNet may include a stack of separable convolution modules that are composed of depth-wise convolution and pointwise convolution (cony 1×1). The separable convolution independently performs convolution in the spatial and channel domains. This factorization of convolution may significantly reduce computational cost from $HWNK^2M$ to $HWNK^2$ (depthwise) plus HWNM (cony 1×1), $HWN(K^2+M)$ in total, where N denotes the number of input channels, $K^2$ denotes the size of convolutional kernel, M denotes the number of output channels, and H×W denotes the spatial size of the output feature map. This may reduce a bottleneck of computational cost to cony 1×1.

In one embodiment, a generative adversarial network (GAN) is used for one or more machine learning models. A GAN is a class of artificial intelligence system that uses two artificial neural networks contesting with each other in a zero-sum game framework. The GAN includes a first artificial neural network that generates candidates and a second artificial neural network that evaluates the generated candidates. The GAN learns to map from a latent space to a particular data distribution of interest (a data distribution of changes to input images that are indistinguishable from photographs to the human eye), while the discriminative network discriminates between instances from a training dataset and candidates produced by the generator. The generative network's training objective is to increase the error rate of the discriminative network (e.g., to fool the discriminator network by producing novel synthesized instances that appear to have come from the training dataset). The generative network and the discriminator network are co-trained, and the generative network learns to generate images that are increasingly more difficult for the discriminative network to distinguish from real images (from the training dataset) while the discriminative network at the same time learns to be better able to distinguish between synthesized images and images from the training dataset. The two networks of the GAN are trained once they reach equilibrium. The GAN may include a generator network that generates artificial intraoral images and a discriminator network that segments the artificial intraoral images. In embodiments, the discriminator network may be a MobileNet.

In one embodiment, one or more machine learning model is a conditional generative adversarial (cGAN) network, such as pix2pix. These networks not only learn the mapping from input image to output image, but also learn a loss function to train this mapping. GANs are generative models that learn a mapping from random noise vector z to output image y, $G:z \rightarrow y$. In contrast, conditional GANs learn a mapping from observed image x and random noise vector z, to y, $G:\{x, z\} \rightarrow y$. The generator G is trained to produce outputs that cannot be distinguished from "real" images by an adversarially trained discriminator, D, which is trained to do as well as possible at detecting the generator's "fakes". The generator may include a U-net or encoder-decoder architecture in embodiments. The discriminator may include a MobileNet architecture in embodiments. An example of a cGAN machine learning architecture that may be used is the pix2pix architecture described in Isola, Phillip, et al. "Image-to-image translation with conditional adversarial networks." *arXiv preprint* (2017).

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and back-propagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

For the model training workflow 205, a training dataset containing hundreds, thousands, tens of thousands, hundreds of thousands or more intraoral scans, images and/or 3D models should be used to form a training dataset. In embodiments, up to millions of cases of patient dentition that may have underwent a prosthodontic procedure and/or an orthodontic procedure may be available for forming a training dataset, where each case may include various labels of one or more types of useful information. Each case may include, for example, data showing a 3D model, intraoral scans, height maps, color images, NIRI images, etc. of one or more dental sites, data showing pixel-level segmentation of the data (e.g., 3D model, intraoral scans, height maps, color images, NIRI images, etc.) into various dental classes (e.g., tooth, gingiva, moving tissue, saliva, blood, etc.), data showing one or more assigned scan quality metric values for the data, movement data associated with the 3D scans, and so on. This data may be processed to generate one or multiple training datasets 236 for training of one or more machine learning models. The machine learning models may be trained, for example, to detect blood/saliva, to detect moving tissue, to detect dirty surfaces, to determine canonical position and orientation for an intraoral scan, to determine relative position and orientation of multiple intraoral scans, and so on.

In one embodiment, generating one or more training datasets 236 includes gathering one or more intraoral scans with labels 210 and/or one or more 3D models with labels 212. The labels that are used may depend on what a particular machine learning model will be trained to do. For example, to train a machine learning model to determine canonical positioning for intraoral scans and/or to register intraoral scans, a training dataset 236 may include canonical position and orientation information and/or relative position and/or orientation information. Training datasets may also be generated that include movement data and/or other information.

Processing logic may gather a training dataset 236 comprising 2D or 3D images, intraoral scans, 3D surfaces, 3D models, height maps, etc. of dental sites (e.g., of dental arches) having one or more associated labels (e.g., canonical coordinate values, scan quality metric values, etc.). One or more images, scans, surfaces, and/or models and optionally associated probability maps in the training dataset 236 may be resized in embodiments. For example, a machine learning model may be usable for images having certain pixel size ranges, and one or more image may be resized if they fall outside of those pixel size ranges. The images may be resized, for example, using methods such as nearest-neighbor interpolation or box sampling. The training dataset may additionally or alternatively be augmented. Training of large-scale neural networks generally uses tens of thousands of images, which are not easy to acquire in many real-world applications. Data augmentation can be used to artificially increase the effective sample size. Common techniques include random rotation, shifts, shear, flips and so on to existing images to increase the sample size.

To effectuate training, processing logic inputs the training dataset(s) 236 into one or more untrained machine learning models. Prior to inputting a first input into a machine learning model, the machine learning model may be initialized. Processing logic trains the untrained machine learning model(s) based on the training dataset(s) to generate one or more trained machine learning models that perform various operations as set forth above.

Training may be performed by inputting one or more of the images, scans or 3D surfaces (or data from the images, scans or 3D surfaces) into the machine learning model one at a time. Each input may include data from an image, intraoral scan or 3D surface in a training data item from the training dataset. The training data item may include, for example, a height map and an associated probability map, which may be input into the machine learning model. As discussed above, training data items may also include color images, images generated under specific lighting conditions (e.g., UV or IR radiation), movement data, and so on. Additionally, pixels of images may include height values or may include both height values and intensity values.

The machine learning model processes the input to generate an output. An artificial neural network includes an input layer that consists of values in a data point (e.g., intensity values and/or height values of pixels in a height map). The next layer is called a hidden layer, and nodes at the hidden layer each receive one or more of the input values. Each node contains parameters (e.g., weights) to apply to the input values. Each node therefore essentially inputs the input values into a multivariate function (e.g., a non-linear mathematical transformation) to produce an output value. A next layer may be another hidden layer or an output layer. In either case, the nodes at the next layer receive the output values from the nodes at the previous layer, and each node applies weights to those values and then generates its own output value. This may be performed at each layer. A final layer is the output layer, where there is one node for each class, prediction and/or output that the machine learning model can produce. For example, for an artificial neural network being trained to determine canonical positioning, the output may be one or more transformation for positioning and orienting the surface in the intraoral scan in a reference coordinate system at an appropriate location on a jaw. For example, an intraoral scan of a left molar of a lower dental arch may be positioned at the lower left side in the GUI.

Processing logic may then compare the determined canonical coordinates (e.g., canonical position information and canonical orientation information) for the intraoral scan to known canonical coordinates for the intraoral scan. Processing logic determines an error (i.e., a positioning error) based on the differences between the output position or transformation and the provided position or transformation. Processing logic adjusts weights of one or more nodes in the machine learning model based on the error. An error term or delta may be determined for each node in the artificial neural network. Based on this error, the artificial neural network adjusts one or more of its parameters for one or more of its nodes (the weights for one or more inputs of a node). Parameters may be updated in a back propagation manner, such that nodes at a highest layer are updated first, followed by nodes at a next layer, and so on. An artificial neural network contains multiple layers of "neurons", where each layer receives as input values from neurons at a previous layer. The parameters for each neuron include weights associated with the values that are received from each of the neurons at a previous layer. Accordingly, adjusting the parameters may include adjusting the weights assigned to each of the inputs for one or more neurons at one or more layers in the artificial neural network.

Once the model parameters have been optimized, model validation may be performed to determine whether the model has improved and to determine a current accuracy of the deep learning model. After one or more rounds of training, processing logic may determine whether a stopping criterion has been met. A stopping criterion may be a target level of accuracy, a target number of processed images from the training dataset, a target amount of change to parameters over one or more previous data points, a combination thereof and/or other criteria. In one embodiment, the stopping criteria is met when at least a minimum number of data points have been processed and at least a threshold accuracy is achieved. The threshold accuracy may be, for example, 70%, 80% or 90% accuracy. In one embodiment, the stopping criteria is met if accuracy of the machine learning model has stopped improving. If the stopping criterion has not been met, further training is performed. If the stopping criterion has been met, training may be complete. Once the machine learning model is trained, a reserved portion of the training dataset may be used to test the model.

Once one or more trained ML models 238 are generated, they may be stored in model storage 245, and may be added to an intraoral scan application (e.g., intraoral scan application 115). Intraoral scan application 115 may then use the one or more trained ML models 238 as well as additional processing logic to implement intuitive intraoral scanning, in which a user can start and stop scanning as desired without following any scanning protocol, and in which scans that fail to register to other scans are not discarded.

In one embodiment, model application workflow 217 includes one or more trained machine learning models that function as a canonical position determiner 267 and/or as a scan assessor 264. These logics may be implemented as separate machine learning models or as a single combined machine learning model in embodiments. According to one embodiment, an intraoral scanner generates a sequence of intraoral scans 248. A 3D surface generator 255 may perform registration between these intraoral scans using overlapping data registration logic 140, stitch the intraoral scans together, and generate a 3D surface 260 from the intraoral scans. As further intraoral scans are generated, these may be registered and stitched to a 3D surface 260, increasing a size of the 3D surface 260 and an amount of data for the 3D surface 260. Additionally, 2D intraoral images (e.g., color 2D images and/or NIRI 2D images) 263 may be generated. Additionally, as intraoral scans 248 are generated, motion data 262 may be generated by an IMU of the intraoral scanner and/or based on analysis of the intraoral scans 248 and/or 2D intraoral images 263.

Input data 262 may include one or more of the intraoral scans 248 and/or a generated 3D surface 260. Input data 262 may additionally include 2D images 263 and/or motion data 262.

Input data 262 may be input into canonical position determiner 267 and/or to scan assessor 264. In embodiments, different input data may be input into each of these logics, which may include a trained neural network. Based on the input data 262, canonical position determiner 267 outputs information on a position and/or orientation of a surface (e.g., the determined 3D surface 260 or a surface from the intraoral scan(s) 248). The output may include one or more vector that transforms the surface to properly place it according to a reference coordinate system. The output may include coordinates for one or more points on the surface. In some embodiments, multiple intraoral scans and/or 3D surfaces that did not register together at block 255 are input into the canonical position determiner 267. Canonical position determiner 267 may then output relative position and orientation for each of the intraoral scans and/or 3D surfaces. For example, canonical position determiner 267 may output a first position and orientation for a first 3D surface and a second position and orientation for a second 3D surface that is a portion of a same jaw as the first 3D surface.

In some embodiments, canonical position determiner 267 may rely on motion data 262 and timing information on when intraoral scans and/or 2D images were generated to register intraoral scans and/or 3D surfaces together. In some embodiments, canonical position determiner 267 performs such registration without the use of a machine learning model (e.g., by extrapolation and/or interpolation of scanner positioning using motion data 262).

A 3D surface positioner 269 determines relative positions and/or orientations of two or more 3D surfaces based on an output of canonical position determiner 267, where one of the 3D surfaces may be based on data from a single intraoral scan. The output of the canonical position determiner 267 can be used to register together two non-overlapping intraoral scans, or an intraoral scan with a 3D surface that it does not overlap with, or two non-overlapping 3D surfaces, for example. An output of the 3D surface positioner 269 may be multiple registered 3D surfaces, which may or may not have any overlapping data.

When a single intraoral scan 248 has been generated, input data 262 for dental site classifier 268 may include that single scan. Once multiple scans 248 have been generated, input data 262 for dental site classifier 268 may include the multiple scans. Classifications based on multiple scans may be more accurate than classifications based on a single scan. Once a 3D surface 260 has been generated, input data 262 to dental site classifier 268 may include the 3D surface (e.g., one or more projections of the 3D surface onto one or more planes), which may result in still more accurate segmentation.

Scan assessor 264 may process the input data 262 to determine one or more scan quality metric scores or values for the intraoral scan(s) 248, 3D surface(s) 260 and/or regions of the 3D surface(s). In one embodiment, scan assessor 264 additionally receives an output from canonical position determiner 267, and uses such information as an input in addition to input data 262. These scan quality metric values may be output in feedback data 274, optionally with one or more notices and/or warnings if the scan quality metric values fail to satisfy one or more scan quality criteria. Distinct scan quality metric scores may be determined for different regions of a 3D surface.

Scan assessor 264 may include one or multiple trained machine learning models trained to identify and/or classify different problems. For example, scan assessor 264 may output a blurriness rating or value for scans and/or 3D surfaces, may identify surfaces as being covered with blood and/or saliva (e.g., via a blood/saliva scan quality metric value), may classify moving tissue (e.g., via a moving tissue scan quality metric value), may output a data density value or rating for regions of a 3D surface, and so on. Scan assessor 264 may additionally or alternatively detect dirty optical surfaces, and output a cleanliness or dirtiness rating or value associated with the detected dirty optical surfaces. In one embodiment, scan assessor 264 detects dirty optical surfaces as set forth in co-pending U.S. patent application Ser. No. 17/230,825, filed Apr. 14, 2021 and entitled "Smart Scanning for Intraoral Scanners," which is incorporated by reference herein.

In some implementations of model application workflow 217, a dirty scanner determiner of scan assessor 264 automatically detects one or more dirty optical surfaces of a scanner. The dirty scanner determiner may or may not use a trained ML model to detect dirty optical surfaces. Instead of, or in addition to, the use of an ML model to identify dirty regions of optical surfaces, scan assessor 264 may use image processing techniques to identify dirty regions of optical surfaces. In one embodiment, scan assessor 264 determines dirty regions of optical surfaces based on depth information from intraoral scans. If a region of an optical surface is marred by grime, dirt, blood, and so on, then a detected depth of pixels associated with that region will generally be much less than depths of pixels that are not associated with dirty regions. Detected depths (or heights) may be compared to one or more depth thresholds (or one or more height thresholds), and dirty regions may be detected for depths that are at or below the one or more depth thresholds (or at or above one or more height thresholds).

Scan assessor 264 may determine sizes of dirty regions and/or a percentage of an optical surface that is dirty. If dirty regions have sizes that exceed a size threshold are detected and/or a percentage of the optical surface that is dirty exceeds a threshold, then scan assessor 264 may determine that the scanner (or a sleeve or attachment on the scanner) is dirty. Scanner cleanliness information may be included in feedback data 274 output by scan assessor 264, for example. If feedback data 274 indicates a dirty scanner, then scan assessor 264 may output a notification to replace a sleeve or attachment on the scanner, or to clean the scanner. Alternatively, or additionally, processing logic may output an indication of an amount or percentage of an optical surface (e.g., a window of a sleeve) that is dirty (e.g., a cleanliness metric value). This indication may appear once a threshold amount of the optical surface is dirty, and may be updated as the optical surface becomes dirtier and/or cleaner. In some embodiments, different dirtiness thresholds are used. If an amount obscured pixels exceeds a first dirtiness threshold, then a notification may be output. If the amount of obscured pixels exceeds a second, greater, dirtiness threshold, then scanning may be automatically paused.

A cleanliness or dirtiness scan quality metric value may be used as a cleanliness or dirtiness scan quality score. Alternatively, a cleanliness or dirtiness scan score may be computed based on the cleanliness or dirtiness scan quality metric value (e.g., as an inverse of the dirtiness scan quality metric value). For example, an increased amount of detected dirty surfaces may result in a lower cleanliness score.

In one embodiment, scan assessor 264 automatically detects a dirty optical surface of an intraoral scanner or protective sleeve or attachment on the intraoral scanner. Processing logic may receive intraoral scans and/or 2D images of an oral cavity, where the scans and/or images were generated by an intraoral scanner. The scans may be generated by generating coherent light or non-coherent light by an intraoral scanner, which is reflected off of an intraoral object back into the intraoral scanner and detected to generate the intraoral scans and/or 2D images. The light may include structured light and/or unstructured light. The intraoral scanner may be inserted into a disposable sleeve, which may act as a protective sleeve to protect the intraoral scanner from contact with the patient's oral cavity.

Processing logic determines, for each of the intraoral scans, an amount of points in the intraoral scans that represent a dirty region of an optical surface associated with the intraoral scanner. Such optical surfaces may include lenses, windows, mirrors, and so on of the scanner and/or of a protective sleeve or protective attachment of the intraoral scanner.

In one embodiment, the intraoral scans include height information (e.g., the intraoral scans may be height maps, which may be 2D monochrome images in which each pixel includes a height value), and at block 2806 processing logic identifies points representing dirty regions of an optical surface based on the height information. For example, processing logic may compare heights detected for pixels with one or more height thresholds (or depth thresholds). If a height is greater than a height threshold (or a depth is less than a depth threshold), then this may indicate that the detected surface is not a point on an intraoral surface but is instead a dirty point on an optical surface associated with the scanner. Thus, points that have a height greater than a height threshold (or depths less than a depth threshold) may be identified as dirty points.

In one embodiment, processing logic identifies unmoving points between multiple intraoral scans and/or images. As the intraoral scanner is moved and multiple scans and/or images are generated, all of the points or pixels on the scans/images should have changing values. For example, a video of the scans/images played in sequence should show movement of intraoral objects relative to the scanner. However, a dirty surface is going to be the same between the scans and/or images. Accordingly, unmoving surfaces may be indicative of dirty pixels. Accordingly, processing logic may compare multiple scans together to identify unmoving pixels between those scans. If a majority of pixels between scans show movement, then those pixels that do not show movement may be identified as dirty pixels.

In some embodiments, distance and non-moving pixel information may be used together to determine which pixels are associated with dirty regions of the scanner.

In one embodiment, processing logic inputs the intraoral scan(s) and/or 2D image(s) into a trained ML model trained to identify dirty optical surfaces of scanners. The ML model may output a map (e.g., a probability map) that includes pixel-level classification of each pixel as being a dirty point or a clean point.

Processing logic determines whether an amount of points that represent a dirty region in the intraoral scan(s) satisfy one or more size threshold. One size threshold may be an overall dirty pixel count threshold. If the total number of dirty points exceeds the overall dirty count threshold, this may indicate that an optical surface of the scanner is dirty. The overall dirty pixel count threshold may be, for example 5000 to 10000 pixels in an embodiment. In one embodiment, the overall dirty pixel count threshold is expressed as a percentage of a total number of pixels, and is about ⅛ to about ¼ (or about ⅙ to about ⅓) of the total number of pixels of the intraoral scanner. One size threshold may be a contiguous dirty region threshold. Processing logic may determine one or more dirty regions in the intraoral scan(s) and/or 2D images, where a dirty region is a region of all adjacent dirty pixels that together form a contiguous dirty region. If a size of any contiguous dirty region exceeds the contiguous dirty region threshold, then this may indicate that the scanner is dirty. In some embodiments, different contiguous dirty region thresholds are associated with different regions of the intraoral scans and/or 2D images. For example, if a large dirty region is in the center of the scans (i.e., in the center of the field of view of the scanner), then this may impair scanning more than if the large dirty region is at a periphery of the scans. Thus, a first dirty region size threshold may be applied to dirty regions in a first region of the intraoral scans and/or 2D images (e.g., near a center of the scans/images), and a second dirty region size threshold may be applied to dirty regions in a second region of the intraoral scans and/or 2D images (e.g., ear a periphery of the scans/images). In one embodiment, the first dirty region size threshold is smaller (fewer dirty pixels) than the second dirty region size threshold.

If the number of points that represent a dirty region in the intraoral scan(s) and/or 2D images does not satisfy any of the size thresholds, the optical surface is determined to not be obscured by dirt/debris. If the number of points that represent a dirty region in the intraoral scan(s) and/or 2D images satisfies one or more of the size thresholds, processing logic may determine whether the same dirty points or same dirty regions have been identified for at least a threshold number of intraoral scans and/or images. As intraoral scans are generated and the intraoral scanner is moved within a patient's mouth, the surfaces detected at each scan should be different. However, dirty optical surfaces will generally show the same dirty surfaces for each of the scans. Accordingly, by comparing dirty pixels and/or dirty regions across multiple intraoral scans and/or images, the accuracy of dirty region determination can be increased. In one embodiment, processing logic determines whether the same dirty region or regions are detected in a majority of images or scans within a moving window. For example, processing logic may determine if at least 7 of 10 most recent scans or images include the same dirty regions. Processing logic may also determine a median or average of dirty regions between multiple scans, and determine dirty regions based on the average or median. If the same dirty points and/or regions are identified for a threshold number of intraoral scans and/or images, or one of the other conditions for dirty regions based on a combination of images are satisfied, processing logic determines that an optical surface of the intraoral scanner is obscured by dirt, grime or debris. In some embodiments, processing logic can determine specifically which optical surface is dirty based on the measured heights/depths. For example, a window of a protective sleeve may be at a known first height, a window of the scanner may be at a known second height, a folding mirror may be at a known third height, and a lens may be at a known fourth height. The measured heights of the dirty regions may be compared to the known heights of each of the optical surfaces, and the optical surface with the height that matches or is close to the measured height may be determined to be the dirty optical surface.

If the same dirty points and/or regions are not identified for at least the threshold number of scans, or one or more other conditions for dirty regions based on a combination of images are not satisfied, processing logic determines that the optical surface is not obscured by dirt or debris (e.g., is not dirty).

In some implementations of model application workflow 217, a moving tissue classifier of scan assessor 264 automatically detects moving tissue in intraoral scans. In one embodiment, the moving tissue classifier (also referred to as an excess material classifier) identifies moving tissue in intraoral scans. Moving tissue may be identified using a trained machine learning model or without the use of a machine learning mode. For example, moving tissue may be identified using the techniques set forth in U.S. patent application Ser. No. 16/865,162, filed May 1, 2020 and entitled "Excess Material Removal Using Machine Learning," which is incorporated by reference herein. Moving tissue may also be identified using the techniques set forth in U.S. patent application Ser. No. 16/837,960, filed Apr. 1, 2020 and entitled "Method and Apparatus for Excessive Materials Removal from Intraoral Scans," which is incorporated by reference herein.

Scan assessor 264 may determine sizes of moving tissue and/or a percentage of an intraoral scan that is obscured by moving tissue. If detected moving tissue has a size that exceeds a size threshold or a percentage of total scan that exceeds a percentage threshold, then scan assessor 264 may determine that the intraoral scan is a low quality scan. A moving tissue scan quality metric value may be used as a moving tissue score. Alternatively, a moving tissue score may be computed based on the moving tissue scan quality metric value (e.g., as an inverse of the moving tissue scan quality metric value). For example, an increased amount of detected moving tissue may result in a lower moving tissue score. A value indicative of a detected amount of moving tissue (e.g., tongue, lips, etc.) and/or a detected percentage of an intraoral scan depicting moving tissue may be included in feedback data 274 output by scan assessor 264. If feedback data 274 indicates moving tissue exceeding a threshold, then scan assessor 264 may output an indication of an amount or percentage of an intraoral scan that is obscured. This indication may appear once a threshold amount or percentage of moving tissue is detected, and may be updated as the amount or percentage of moving tissue changes. In some embodiments, different moving tissue thresholds are used.

In some implementations of model application workflow 217, dental object classifier (e.g., which may be a blood/saliva detector) of scan assessor 264 automatically detects blood and/or saliva in intraoral scans and/or 2D images. Blood and/or saliva may be identified using a trained machine learning model or without the use of a machine learning model. For example, a machine learning model may have been trained to identify blood and/or saliva based on a training dataset of intraoral scans/surfaces and/or 2D images with and without blood and/or saliva on teeth. The machine learning model may output an indication of an amount of blood and/or saliva detected in an input intraoral scan and/or image. In one embodiment, the machine learning model outputs pixel-level or patch-level classifications of "blood/saliva" and "no blood/saliva." For example, the machine learning model may output a map with a number of points or pixels that matches a number of points or pixels of one or more input images and/or scans that were input. Each point or pixel in the map may be classified as blood/saliva or no blood/saliva. Processing logic may determine a percentage of the intraoral scan and/or image that has a blood/saliva classification, and assign a blood/saliva metric value based on this percentage. If the blood/saliva metric value exceeds a threshold, this may indicate that the intraoral scan is of low quality and additional scans of a region of a dental site represented in the intraoral scan should be rescanned. In one embodiment, a region of a 3D surface generated from a portion of an intraoral that was identified as having blood and/or saliva may be marked as such on the 3D surface. This may inform a user that the region of the 3D surface is showing blood and/or saliva and not the underlying surface of the dental site. In one embodiment, the marking for the blood and/or saliva may include a visualization such as a color, transparency, fill pattern, etc. that differs from a visualization of a remainder of the 3D surface. For example, the blood/saliva may be shown in red to indicate blood.

A blood/saliva scan quality metric value may be used as a blood/saliva scan quality score. Alternatively, a blood/saliva score may be computed based on the blood/saliva scan quality metric value (e.g., as an inverse of the blood/saliva scan quality metric value). For example, an increased amount of detected blood/saliva may result in a lower blood/saliva score.

Scan assessor 264 may determine an amount of blood and/or saliva on scanned dental objects. If an amount of detected blood and/or saliva exceeds a threshold, then scan assessor 264 may determine that the intraoral scan is a low quality scan. A value indicative of a detected amount blood and/or saliva may be included in feedback data 274 output by scan assessor 264. If feedback data 274 indicates blood and/or saliva exceeding a threshold, then scan assessor 264 may output an indication of an amount blood and/or saliva that is detected. This indication may appear once a threshold amount blood and/or saliva is detected, and may be updated as the amount of blood and/or saliva changes.

In some implementations of model application workflow 217, a scan speed determiner of scan assessor 264 automatically determines a scan speed associated with intraoral scans. Moving the scanner too quickly may result in blurry intraoral scans and/or a low amount of overlap between scans. Moving the scanner too slowly increases the time that it takes to complete intraoral scanning. Accordingly, it can be beneficial to scan within a scan speed range between an upper scan speed threshold and a lower scan speed threshold. Scan assessor 254 may use motion data 262, 2D intraoral images 263 and/or intraoral scans 248, including the timing of when such motion data 262, 2D intraoral images 263 and/or intraoral scans 248 were generated, to determine a scan speed associated with one or more intraoral scans 248. A value indicative of a detected scan speed may be included in feedback data 274 output by scan assessor 264. If feedback data 274 indicates a scan speed approaching or exceeding an upper scan speed threshold or approaching or below a lower scan speed threshold, then scan assessor 264 may output an indication of the scan speed.

A scan speed scan quality metric value may be used as a scan speed score. Alternatively, a scan speed score may be computed based on the scan speed scan quality metric value (e.g., as an inverse of the scan speed scan quality metric value). For example, an increased scan speed may result in a lower scan speed score.

In some implementations of model application workflow 217, a scan distance determiner of scan assessor 264 automatically determines a scanner distance associated with one or more intraoral scans. Scan quality may be highest when a scanner probe is within a range of distances from an object being scanned. For example, the probe of the scanner too far from a surface being scanned may reduce a density of data points for the scanned surface and/or may reduce a scan quality. The scan distance determiner may determine one or more distances between a scanning face of the probe of the scanner and a dental object being scanned. The scan distance determiner may determine, for example, an average distance, a maximum distance, a minimum distance, one or more distance percentiles, and so on based on an intraoral scan. Distances may be determined using structured light, confocal imaging, stereo imaging, and/or other techniques for 3D imaging. Processing logic may compute statistics on determined distances from an intraoral scan, such as a minimum distance, a maximum distance, an average distance, a median distance, one or more distance percentiles (e.g., a 90% percentile, a 75% percentile, a 50% percentile, and so on). One of more such distance statistics may be used to determine a scan distance value. A value indicative of a detected scan distance may be included in feedback data 274 output by scan assessor 264. If feedback data 274 indicates a scan distance approaching or exceeding an scan distance threshold (which may be one or more scan distance threshold applied to one or more scan distance statistics), then scan assessor 264 may output an indication of the scan distance value.

Figure 3:
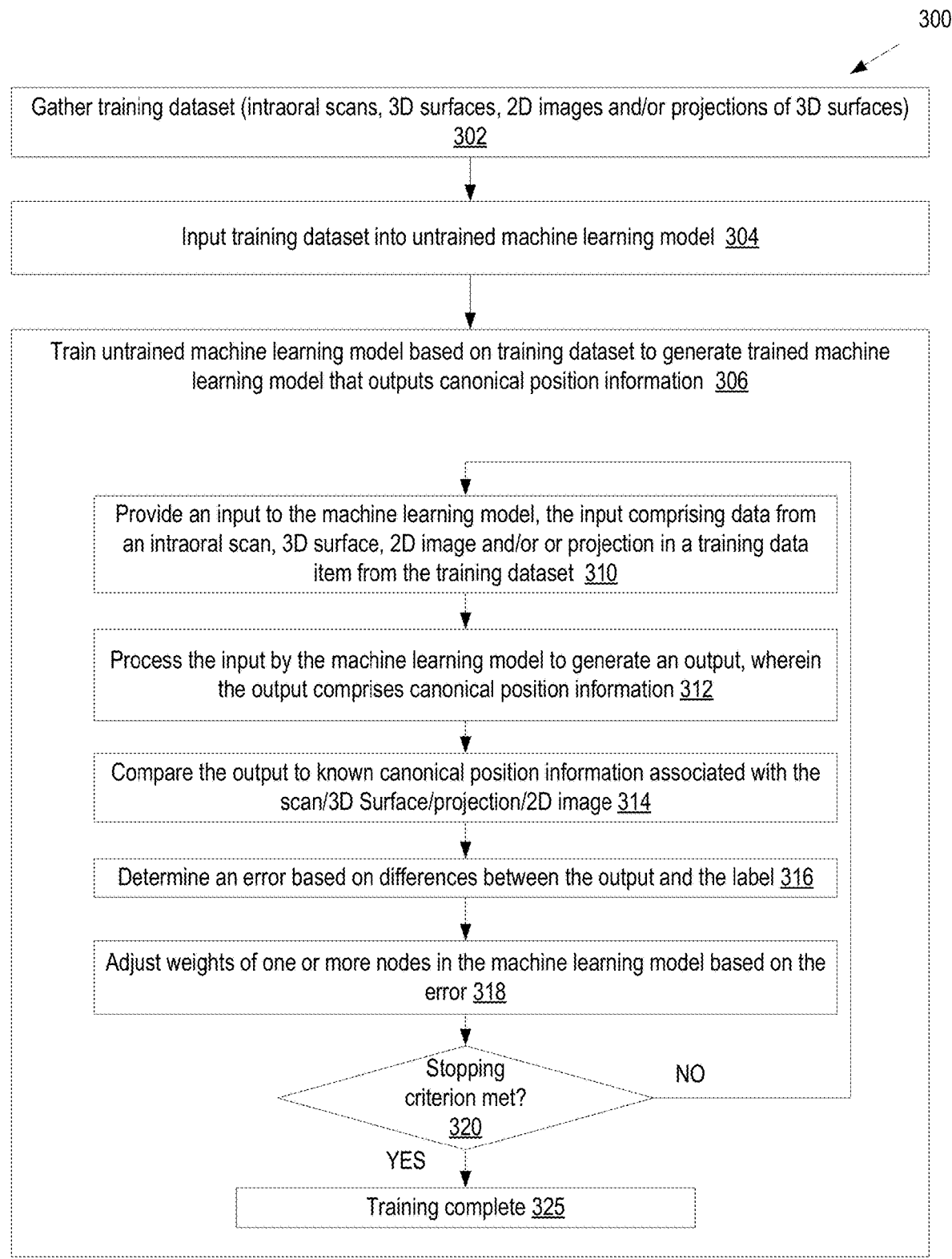
FIG. 3 is a flow chart illustrating an embodiment for a method of training a machine learning model to determine canonical position information for intraoral scans and/or 3D surfaces of dental sites.

FIG. 3 is a flow chart illustrating an embodiment for a method 300 of training a machine learning model to determine canonical position information for 3D surfaces and/or intraoral scans, where the canonical position information may include position and/or orientation of the 3D surfaces and/or intraoral scan surfaces in a reference coordinate system and/or on a reference jaw. At block 302 of method 300, processing logic gathers a training dataset, which may include intraoral scans (e.g., height maps) of dental sites, 3D surfaces of dental sites, 2D images of dental sites, projections of 3D surfaces of dental sites and/or movement information (associated with movement of a scanner between generation of scans and/or images). Each data item (e.g., intraoral scan, image, 3D surfaces, etc.) of the training dataset may include one or more labels. The data items in the training dataset may include image-level labels that indicate a position and/or orientation for the entire surface or for a portion of the surface (e.g., a center of the surface, a lower left most point on the surface, etc. The data items in the training dataset may also include other labels, such as pixel-level coordinates of each point or pixel on the surface. The data items may also include other labels, such as labels of one or more scan quality metric values, and so on.

At block 304, data items from the training dataset are input into the untrained machine learning model. At block 306, the machine learning model is trained based on the training dataset to generate a trained machine learning model that outputs canonical position information (e.g., position and orientation in a global reference frame, coordinates in a reference frame, etc.). The machine learning model may additionally or alternatively be trained to perform registration of scans and/or 3D surfaces, and/or to determine transformations to perform on a surface to position it in a reference frame.

In one embodiment, at block 310 an input of a training data item is input into the machine learning model. The input may include data from an intraoral scan (e.g., a height map), a 3D surface, a 2D image, a projection of a 3D surface, and/or movement data. At block 312, the machine learning model processes the input to generate an output. The output may include a canonical coordinates, transformations, etc. for the 3D surface and/or intraoral scan, for example.

At block 314, processing logic compares the output canonical coordinates, transformations, etc. to canonical coordinates, transformations, etc. used to label the input. At block 316, processing logic determines an error based on differences between the output coordinates/transformations and the label of the coordinates/transformations associated with the input. At block 318, processing logic adjusts weights of one or more nodes in the machine learning model based on the error.

At block 320, processing logic determines if a stopping criterion is met. If a stopping criterion has not been met, the method returns to block 310, and another training data item is input into the machine learning model. If a stopping criterion is met, the method proceeds to block 325, and training of the machine learning model is complete.

Figure 4:
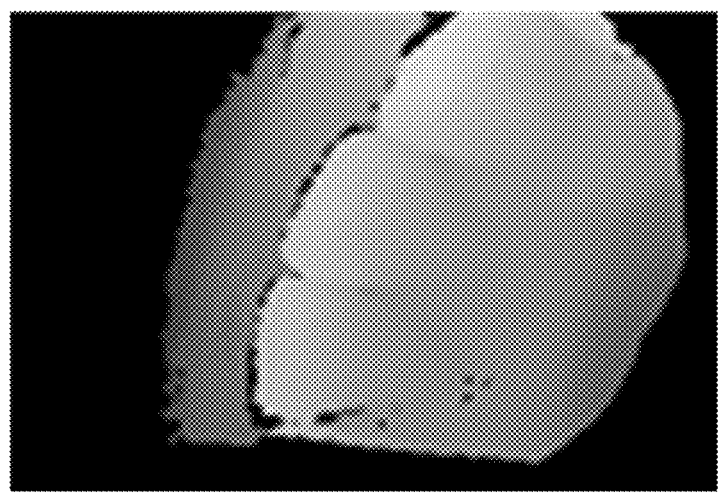
FIG. 4 illustrates example individual intraoral scans of regions of a dental arch used to train a machine learning model to determine canonical position information for intraoral scans.
Figure 4:
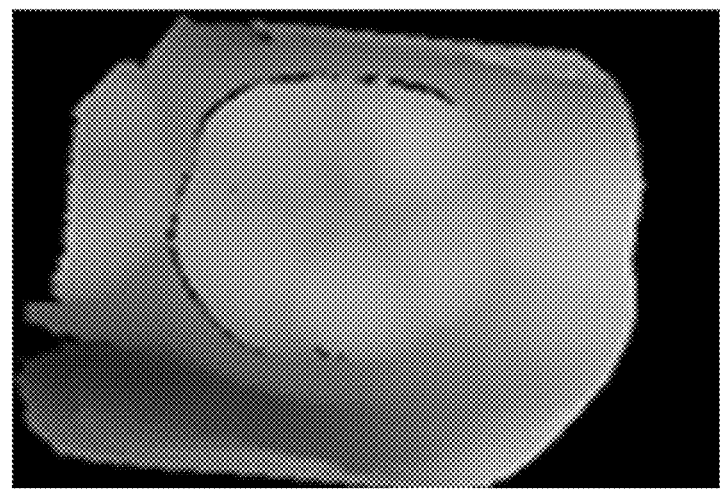
Figure 4:
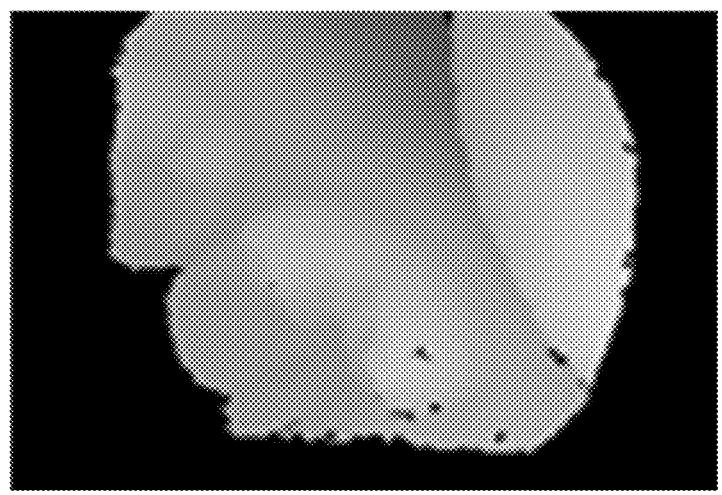

FIG. 4 illustrates example intraoral scans 402, 404, 406 that may be used to train a machine learning model to determine canonical position information and/or transformations and/or may be input into a trained ML model in order for the trained ML model to determine canonical position information and/or transformations. A solution that uses individual height maps (or other intraoral scans) to determine canonical position information and/or to register intraoral scans to other intraoral scans and/or 3D surfaces as those height maps and/or scans are generated can provide a real time or near-real time determination of relative positions and orientations of the received intraoral scans and previously received intraoral scans and/or previously generated 3D surfaces. The intraoral scans 402, 404, 406 may be discrete or raw intraoral scans or may be blended intraoral scans. In one embodiment, the intraoral scans 402, 404, 406 are blended intraoral scans. Use of blended intraoral scans to determine canonical position information and/or transformations can reduce computational resource usage as compared to use of raw intraoral scans. Individual intraoral scans are small due to a field of view (FOV) of the scanner, and are noisy, which makes it challenging to accurately classify canonical position information from intraoral scans.

Figure 5:
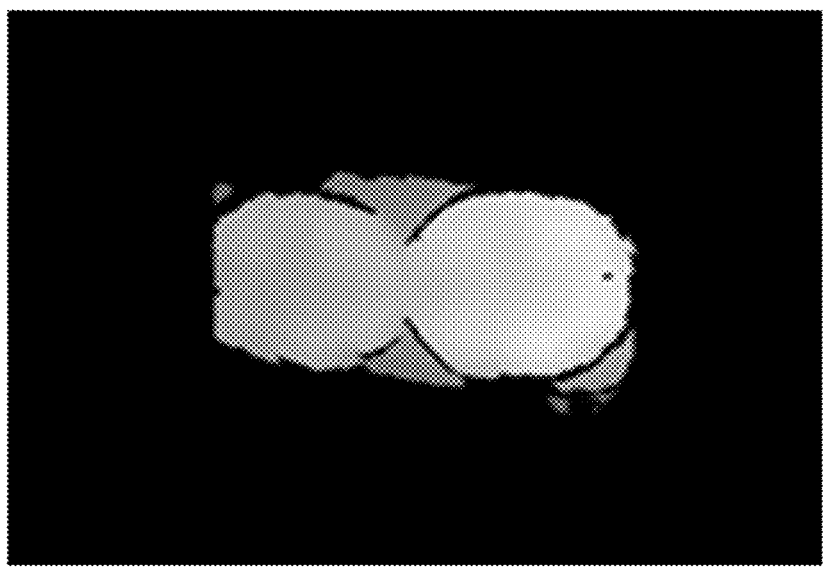
FIG. 5 illustrates example views of 3D surfaces of dental sites used to train a machine learning model to determine canonical position information for 3D surfaces.
Figure 5:
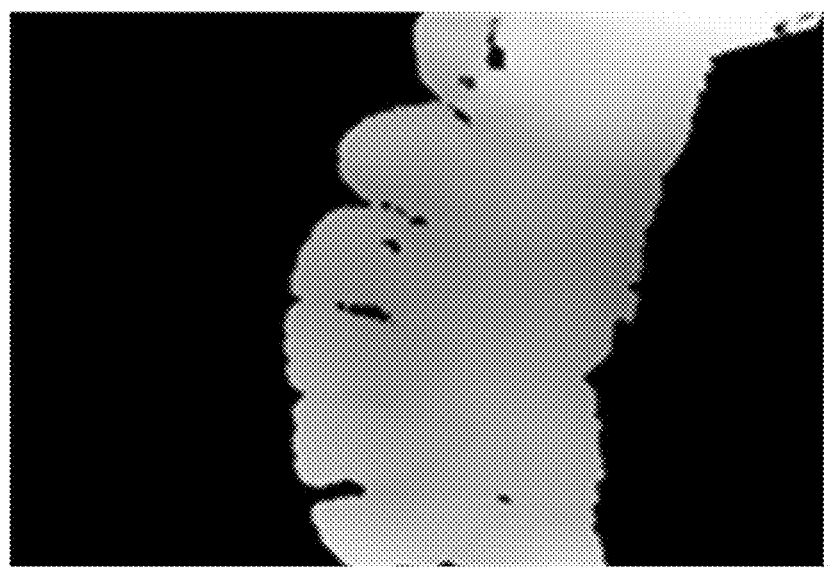
Figure 5:
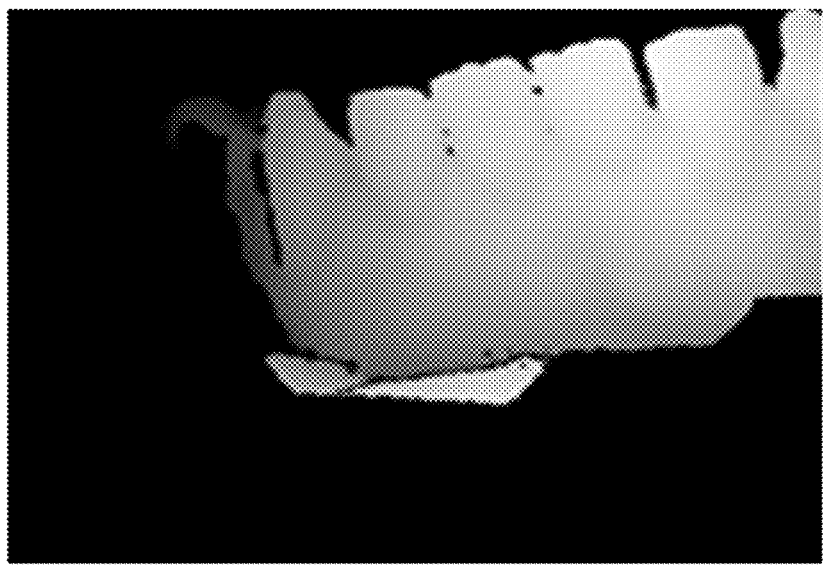

FIG. 5 illustrates example projections of 3D surfaces 500, 505, 510 (referred to as multiple jaw views since they combine data from multiple intraoral scans and project that data onto multiple planes to generate a set of views (e.g., height maps)) that may be used to train a machine learning model to determine canonical position information and/or transformations and/or may be input into a trained ML model in order for the trained ML model to determine canonical position information and/or transformations. In embodiments, 3D surfaces may be projected onto multiple planes to generate projections with height information (e.g., height maps) that contain information associated with multiple intraoral scans. Alternatively, 3D surfaces may be input into a trained ML model. Processing logic can use a set of projections of a jaw from different directions that are available during a scanning from a partially stitched 3D surface. For example, the multiple projections may be input into different input layers or channels of a trained neural network. Such projections give more information than individual height maps or intraoral scans (approaching occlusal view richness) and, at the same time, are available in or near-real time from near the very beginning of scanning. This approach gives high accuracy along with a real time nature.

FIGS. 6-8, 10 and 12-13 illustrate methods related to intraoral scanning and generation 3D surfaces of dental sites. The methods may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the methods are performed by a computing device executing an intraoral scan application 115, such as shown in FIG. 1.

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

Figure 6:
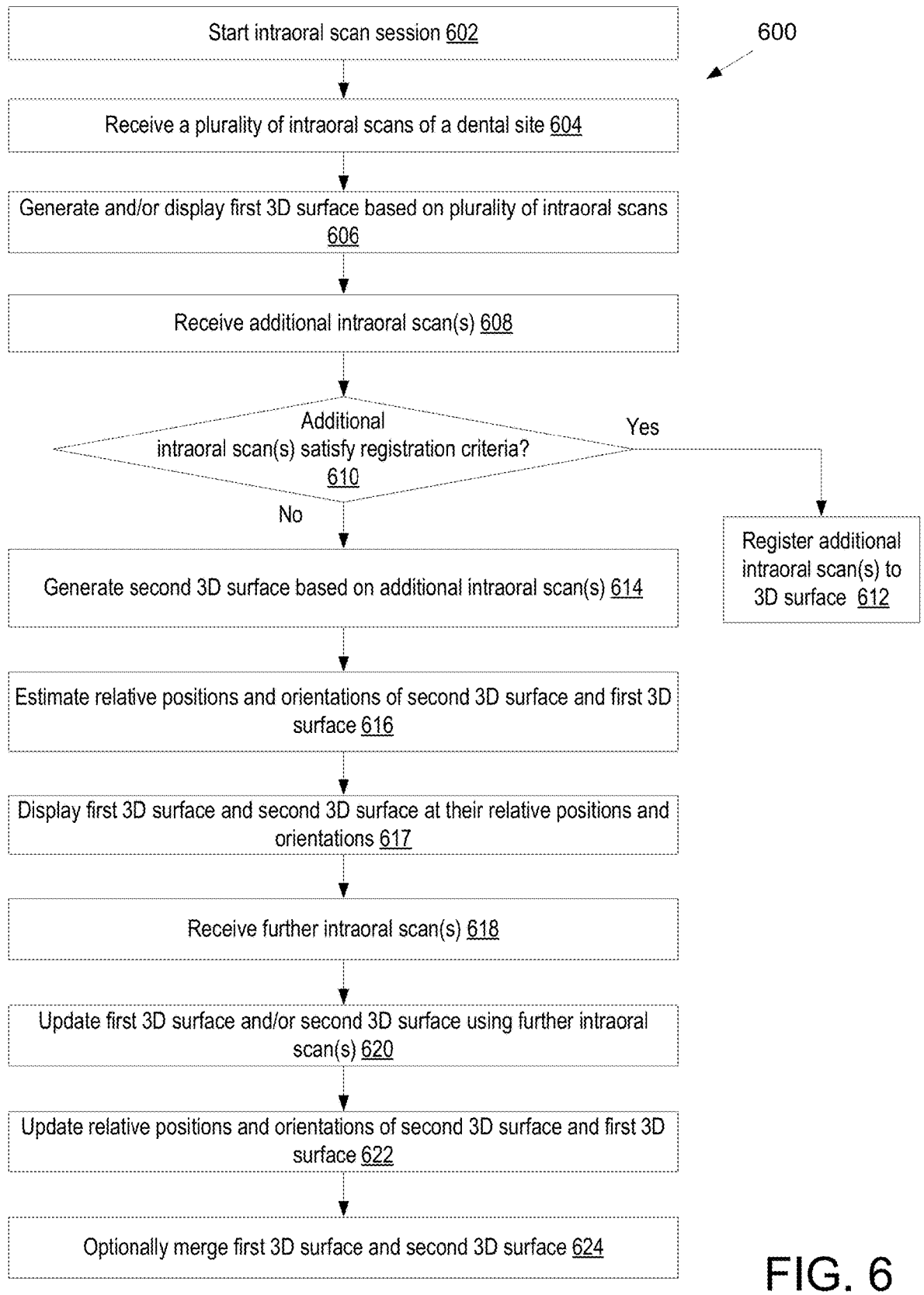
FIG. 6 illustrates a flow diagram for a method of generating multiple 3D surfaces of a dental arch and determining relative positions and/or orientations of the multiple 3D surfaces, in accordance with embodiments of the present disclosure.

FIG. 6 illustrates a flow diagram for a method 600 of generating multiple 3D surfaces of a dental arch and determining relative positions and/or orientations of the multiple 3D surfaces, in accordance with embodiments of the present disclosure. At block 602 of method 600, an intraoral scan session may be started. This may occur when a doctor inserts an intraoral scanner into a patient's mouth and begins generating intraoral scans. The intraoral scan session may proceed until enough intraoral scans have been captured to generate a 3D model of a dental site of the patient (e.g., of the patient's upper and/or lower dental arch). At block 604, processing logic receives a plurality of intraoral scans of a dental site (e.g., dental arch, tooth, group of teeth, etc.). Processing logic may additionally receive one or more 2D images of the dental site (e.g., color 2D images generated under white light, near-infrared (NIRI) 2D images, etc.).

At block 606, processing logic may register the intraoral scans together using one or more registration algorithm that relies upon overlapping features of the intraoral scans, and stitches the registered intraoral scans together to generate a 3D surface representing a portion of the dental site that has been scanned thus far. As further intraoral scans are received, they may be registered to the 3D surface and stitched to the 3D surface to update the 3D surface. This 3D surface may be output to a display and updated in real time or near-real time as intraoral scans are received and stitched together.

In some embodiments, if only a few intraoral scans have been generated, then there may be insufficient data for accurate registration and stitching using the intraoral scans. In such instances, the received 2D images, which may be associated with the intraoral scans, may be used to stitch together the intraoral scans. The 2D images may have a higher data density than the intraoral scans, but lack depth information. However, for intraoral scans generated close together in time, 2D data may be sufficient for at least a preliminary registration between scans. Each of the intraoral scans may be associated with a 2D image generated close in time to those intraoral scans. The 2D images may be registered and stitched together, and transformations between the 2D images may be determined based on such registration. Such transformations may then be applied to the associated intraoral scans. In some embodiments, the 2D images are generated at different times than the intraoral scans. Accordingly, timing information for the 2D images and the intraoral scans may be used to determine adjustments to make to the transformations determined for registering the 2D images together in order to determine proper transformations to apply to the intraoral scans for registration.

At block 608, processing logic receives one or more additional intraoral scans of the dental site. Processing logic may also receive one or more additional 2D images. At block 610, processing logic determines whether the additional intraoral scans satisfy registration criteria that are using overlapping features between the intraoral scan(s) and the 3D surface. In one embodiment, intraoral scans of the scan session may not register to existing intraoral scans or the first 3D surface when they do not sufficiency overlap each other. Intraoral scans do not sufficiently overlap each other when there is insufficient overlapping data between the two intraoral scans to be able to determine that a portion of the first intraoral scan is of the same object (e.g., region of a dental site) as a portion of the second intraoral scan or 3D surface. When intraoral scans do not sufficiently overlap each other, registration based on overlapping or shared features may be less accurate or may not be possible.

Intraoral scans may be registered when a sufficient area and/or number of points within each intraoral scan may be mapped to an adjacent intraoral scan or the first 3D surface. If the received additional intraoral scans satisfy the registration criteria, the method proceeds to block 612 and those additional intraoral scans are registered to and stitched to the previously generated 3D surface, updating the 3D surface. However, if the received additional intraoral scans fail to satisfy the registration criteria, the method proceeds to block 614.

At block 614, processing logic generates a second 3D surface based on the additional intraoral scans. Processing logic may perform registration between the additional intraoral scans based on overlapping features between the additional intraoral scans, and stitch the additional intraoral scans together to generate the second 3D surface. In traditional systems, if the additional intraoral scans failed to register to the first 3D surface, those additional intraoral scans would be discarded, and a user of the intraoral scanner would be notified to move the scanner back to a position that overlaps with the region of the dental site that has already been scanned so as to start generating additional intraoral scans with sufficient overlapping features with the 3D surface. In some systems, a recovery mode is initiated when registration fails, and a user must complete recovery before scanning can resume.

At block 616, processing logic may estimate relative positions and orientations of the second 3D surface and the first 3D surface. In one embodiment, processing logic inputs data from the plurality of intraoral scans, the additional intraoral scan(s), the first 3D surface and/or the second 3D surface into a trained machine learning model. The trained machine learning model may then output relative position and orientation information for the first 3D surface and the second 3D surface. In one embodiment, the trained machine learning model outputs first canonical position information for the first 3D surface and second canonical position information for the second 3D surface. In one embodiment, processing logic estimates relative positions and orientations using movement data (also referred to as motion data), which may be generated by an IMU or determined based on intraoral scans and/or 2D images.

In some embodiments, the received additional 2D images may be used to register the one or more additional intraoral scans to the first 3D surface. Each of the additional intraoral scans may be associated with an additional 2D image generated close in time to those additional intraoral scans. The additional 2D image(s) may be registered to one or more 2D images associated with the plurality of intraoral scans used to generate the first 3D surface, and transformations between the 2D images may be determined based on such registration. Such transformations may then be applied to the associated additional intraoral scans to enable rough registration of the additional intraoral scans to the first 3D surface. In some embodiments, the 2D images are generated at different times than the intraoral scans. Accordingly, timing information for the 2D images and the intraoral scans may be used to determine adjustments to make to the transformations determined for registering the 2D images together in order to determine proper transformations to apply to the intraoral scans for registration to the first 3D surface.

At block 617, processing logic displays the first 3D surface and the second 3D surface. If rough estimates of relative position and/or orientation of the 3D surfaces have been determined, then the 3D surfaces may be displayed at their relative positions and orientations. If the relative positions and/or orientations of the 3D surfaces are unknown, then the 3D surfaces may be shown in different regions of a display, but their positioning may not be based on any estimated relative positions and/or orientations. Accordingly, different unconnected 3D surfaces may be positioned at different regions of a display. In some embodiments, the relative positions and/or orientations of the 3D surfaces are unknown, and positioning of the 3D surfaces on the screen may not be based on any estimates of relative positions and orientations of the 3D surfaces. For example, a current or active 3D surface (3D surface to which a most recent intraoral scan was registered successfully using overlapping data) may be shown in a center of a display, while other unconnected 3D surfaces may be shown at a bottom of the display, on a side of the display, and so on.

In an example, a user may have scanned the left-side molars on the lower jaw, resulting in the first 3D surface and the right-side molars on the lower jaw, resulting in the second 3D surface. However, the user may not have scanned the middle teeth on the lower jaw. In spite of the fact that there is no overlapping information for the first and second 3D surfaces, processing logic may determine that the first 3D surface is for the left side of the lower dental arch and that the second 3D surface is for the right side of the lower dental arch, and may display the first and second 3D surfaces appropriately as they would appear on a human jaw.

At block 618, processing logic may receive one or more further intraoral scans. At block 620, processing logic may update the first 3D surface and/or the second 3D surface using the further intraoral scans. For example, processing logic may register and stitch the further intraoral scans to the first 3D surface based on overlapping features between one or more of the further intraoral scans and the first 3D surface. Similarly, processing logic may register and stitch the further intraoral scans to the second 3D surface based on overlapping features between one or more of the further intraoral scans and the second 3D surface.

At block 622, processing logic may update the relative positions and orientations of the second 3D surface and first 3D surface. Data for the updated first and/or second 3D scans may be input into the trained machine learning model, which may output updated estimates of the relative position and orientation of the first and second 3D surfaces. As additional information from the further intraoral scans is added to the first and/or second 3D surfaces, the estimated relative positions and orientations of these respective 3D surfaces may be improved in accuracy.

At some point enough intraoral scans of the intervening space between the first 3D surface and the second 3D surface may be received to enable the first 3D surface to register and stitch to the second 3D surface based on overlapping features between these two 3D surfaces. Once such intraoral scans are received, processing logic may merge the first and second 3D surfaces into a single 3D surface. In one embodiment, when multiple 3D surfaces are merged together an indication of such merging is displayed. For example, a current or active 3D surface may be shown with a different visualization (e.g., a different color, shade, transparency, etc.) than other 3D surfaces. When an active 3D surface is merged with another 3D surface, the visualization of the other 3D surface may be updated to match the visualization of the active 3D surface to show that they are now a single 3D surface. Additionally, or alternatively, processing logic may snap unconnected 3D surfaces together, for which relative positions and/or orientations may not have previously been estimated.

Note that method 600 is discussed with reference to two 3D surfaces. However, three, four or even more 3D surfaces may be generated using method 600. As sufficient information to merge 3D surfaces is received, the multiple 3D surfaces may be merged and the total number of 3D surfaces may be reduced until there is a single 3D surface for a dental site (e.g., a dental arch). Additionally, any discussion herein directed to two 3D surfaces also applies to more than two 3D surfaces. For example, a trained machine learning model may be used to estimate the relative positions and orientations of three, four, five, etc. 3D surfaces.

Figure 7A:
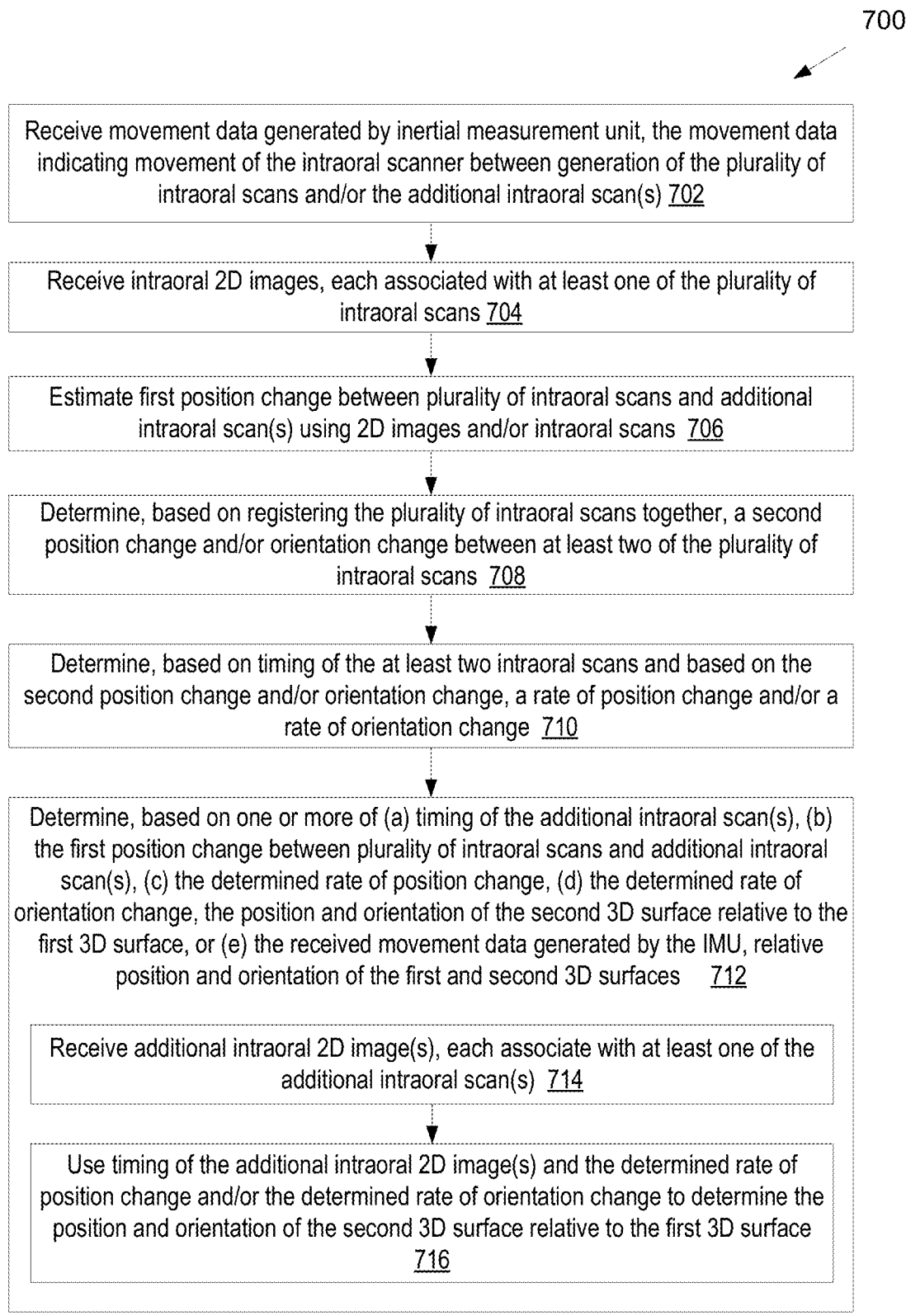
FIG. 7A illustrates a flow diagram for a method of determining relative positions and/or orientations of multiple 3D surfaces of a dental arch, in accordance with embodiments of the present disclosure.

FIG. 7A illustrates a flow diagram for a method 700 of determining relative positions and/or orientations of multiple 3D surfaces of a dental arch, in accordance with embodiments of the present disclosure. Method 700 may be performed, for example, to estimate relative position and/or orientation of 3D surfaces and/or intraoral scans at block 616 of method 600.

At block 702 of method 700, processing logic may receive movement data generated by an inertial measurement unit, the movement data indicating movement of the intraoral scanner between generation of one or more of a plurality of intraoral scans used to generate a first 3D surface and/or indicating movement of the intraoral scanner between generation of the one or more intraoral scans and one or more additional intraoral scans used to generate a second 3D surface.

At block 704, processing logic may receive a plurality of intraoral 2D images. Each of the plurality of intraoral 2D images may be associated with one or more of the intraoral scans. A scanner may alternate between generation of intraoral scans and 2D images. For example, a scanner may generate 3-8 intraoral scans, then an intraoral image, then 3-8 intraoral scans, then an intraoral image, and so on. An intraoral image may be associated with one or more of the intraoral scans generated before and/or after the intraoral image was generated. Each of the intraoral scans and/or intraoral images may be associated with a time stamp indicating a time at which the intraoral scan or image was generated.

At block 706, processing logic may estimate a first position change and/or orientation change between one or more of a plurality of intraoral scans used to generate a first 3D surface and one or more additional intraoral scans used to generate a second 3D surface based on comparison of the intraoral scans and/or 2D images. At block 708, processing logic may determine, based on registering the plurality of intraoral scans used to generate the first 3D surface together, a second position change and/or orientation change between at least two of the plurality of intraoral scans. At block 710, processing logic may determine, based on timing of the at least two intraoral scans and based on the second position change and/or orientation change, a rate of position change and/or a rate of orientation change of the scanner.

At block 712, processing logic may determine, based on one or more of (a) timing of the additional intraoral scans, (b) the first position change between the plurality of intraoral scans and the additional intraoral scans, (c) the determined rate of position change or (d) the determined rate of orientation change, the position and orientation of the second 3D surface relative to the first 3D surface. Additionally, or alternatively, the received movement data generated by the IMU may be used along with the timing information to estimate relative position and orientation of the first and second 3D surfaces. This may include at block 714 receiving additional intraoral 2D images, each associated with at least one of the additional intraoral scans, and at block 716 using timing of the additional intraoral 2D images and the determined rate of position change and/or the determined rate of orientation change to determine the position and orientation of the second 3D surface relative to the first 3D surface. The movement data for the one or more intraoral scans may be used to compute, for example, an average rate of change in position of the intraoral scanner along one, two or three axes and/or rate of change of rotation of the intraoral scanner about one, two or three axes. The averages may be moving averages computed from a threshold number of most recent intraoral scans, for example. This average rate of change of rotation and/or position may be used along with timing information for one or more of a plurality of intraoral scans used to generate a first 3D surface and one or more additional intraoral scans used to generate a second 3D surface to determine a change in position and/or orientation between the first 3D surface generated from the plurality of intraoral scans and the second 3D surface generated from the one or more additional intraoral scans.

Figure 7B:
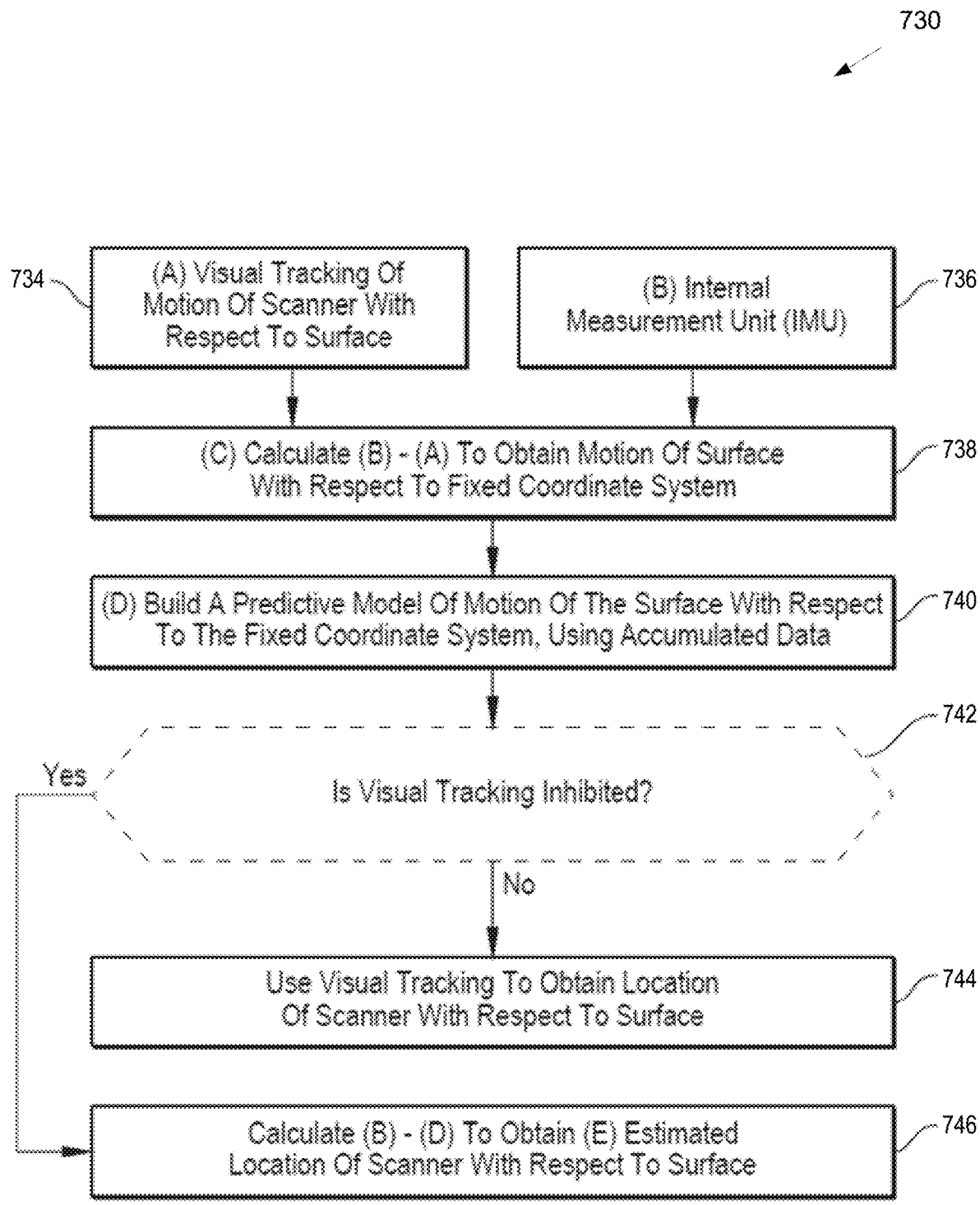
FIGS. 7B-C are flow charts outlining respective methods for tracking motion of an intraoral scanner, in accordance with some embodiments of the present disclosure.
Figure 7C:
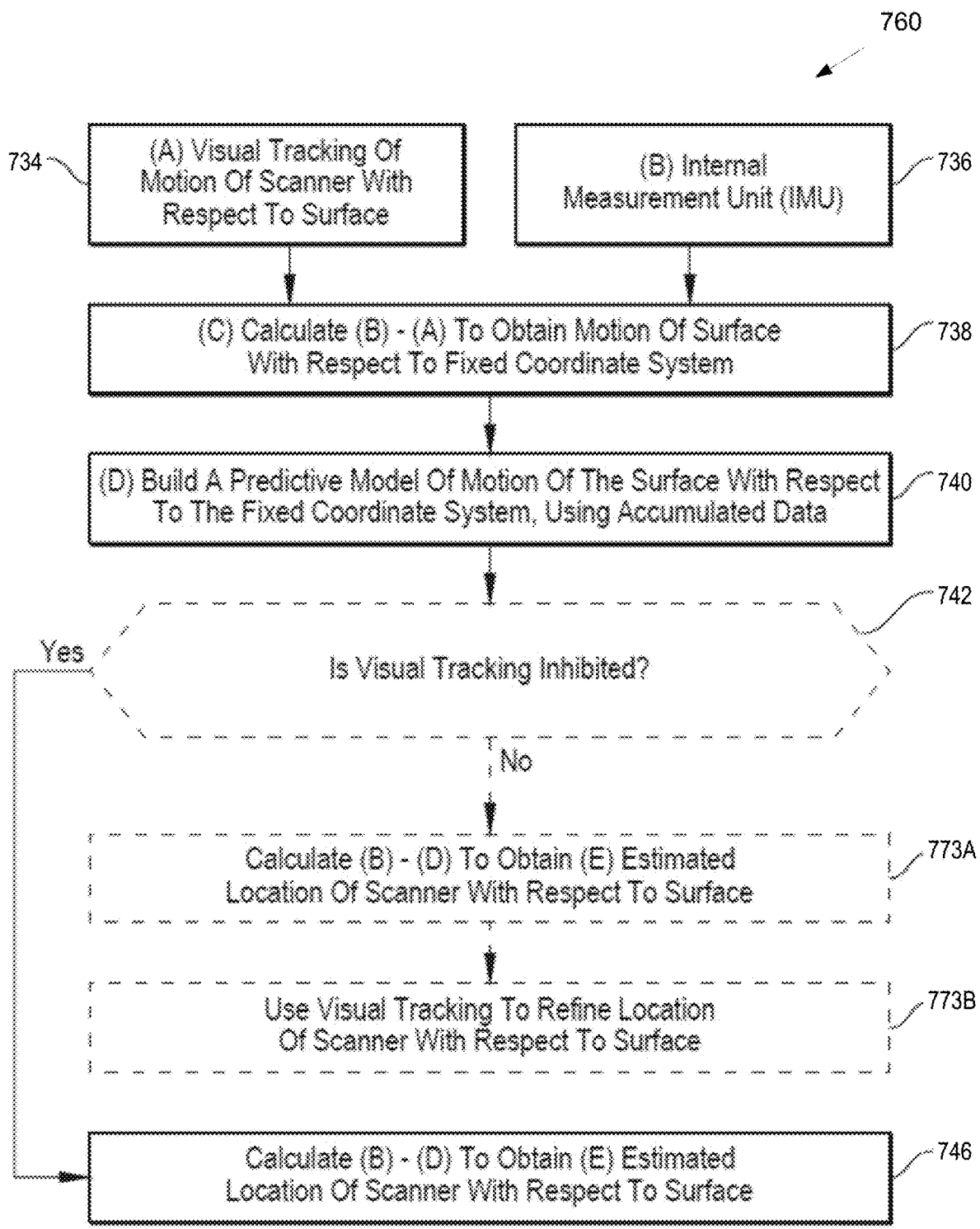

Reference is now made to FIGS. 7B-C, which are flow charts 730, 760 outlining respective methods for tracking motion of the intraoral scanner, i.e., scanner 150, in accordance with some embodiments of the present disclosure. For the purpose of intraoral scanning, an estimation of the location of the scanner with respect to an intraoral object (e.g., dental site) being scanned, i.e., the three-dimensional intraoral surface, is beneficial at all times during a scan. Generally, the intraoral scanner may use at least one camera that is coupled to the intraoral scanner to measure motion of the intraoral scanner with respect to an object being scanned via visual tracking (block 734). The visual tracking of the motion of the intraoral scanner with respect to the object being scanned is obtained by stitching of the respective surfaces or point clouds obtained from adjacent image frames or by a simultaneous localization and mapping (SLAM) algorithm, which in turn provides information on how the intraoral scanner has moved between one frame and the next. However, there may be times during a scan where sufficient visual tracking of the motion of the intraoral scanner with respect to the object is not available, e.g., in a hard to capture region of the intraoral scene, or if moving tissue blocks the camera, such as, for example, the patients tongue, the patient's cheek, or the practitioner's fingers. An inertial measurement unit (IMU) coupled to the intraoral scanner may measure motion of the intraoral scanner with respect to a fixed coordinate system. However, using an IMU alone is generally not sufficient, in and of itself, in order to determine a location of the intraoral scanner with respect to object being scanned, because the object is part of a subject's head, which itself may move.

Thus, embodiments combine (a) visual tracking of the scanner's motion with (b) inertial measurement of the scanner's motion to (i) accommodate for times when sufficient visual tracking is unavailable, and optionally (ii) when visual tracking is available, help provide an initial guess for movement of the intraoral scanner with respect to an intraoral object from one frame to the next so as to leave only refinement of the location of intraoral scanner to be obtained from visual tracking, thus reducing stitching time. In block 734, at least one camera coupled to the intraoral scanner may be used to measure (A) motion of the intraoral scanner with respect to an intraoral surface being scanned. In block 736, at least one IMU coupled to the intraoral scanner may be used to measure (B) motion of the intraoral scanner with respect to a fixed coordinate system (i.e., the Earth's frame of reference). In block 738, processing logic may calculate motion of the intraoral surface with respect to the fixed coordinate system by subtracting (A) motion of the intraoral scanner with respect to the intraoral surface from (B) motion of the intraoral scanner with respect to the fixed coordinate system. Alternatively, the motion of the intraoral surface with respect to the fixed coordinate system may be otherwise calculated based on (A) the motion of the intraoral scanner with respect to the intraoral surface and (B) motion of the intraoral scanner with respect to the fixed coordinate system. The motion of the intraoral surface may be calculated by calculating a difference between the motion of the intraoral scanner with respect to the fixed coordinate system and the motion of the intraoral surface with respect to the fixed coordinate system. Typically, motion of the intraoral surface includes motion of the subject's upper and/or lower jaw.

While scanning, processing logic may accumulate data of motion of the intraoral surface with respect to the fixed coordinate system collected in block 738. In block 740, based on accumulated data of motion of the intraoral surface with respect to the fixed coordinate system, processing logic may build a predictive model of (D) motion of the intraoral surface with respect to the fixed coordinate system. The predictive model may be used to calculate (E) an estimated location of the intraoral scanner with respect to the intraoral surface. In one embodiment, the predictive model is based on two assumptions. The first assumption is that the motion frequency of the subject's head, e.g., upper and/or lower jaw, is substantially slower than (a) the frame-rate capture of the camera that is performing the visual tracking, and (b) the sampling frequency of the IMU. The second assumption is that the motion frequency of the subject's head, e.g., upper and/or lower jaw, is also substantially slower than the motion frequency of the intraoral scanner with respect to the subject's head, e.g., upper and/or lower jaw. Thus, between any two captured frames it can be assumed that the motion of the subject's head is minimal and relatively smooth.

Reference is now made specifically to FIG. 7B. For some applications, as indicated at block 742, as long as visual tracking of (A) motion of the intraoral scanner with respect to the intraoral surface is not inhibited, then the visual tracking may be used to obtain the location of the intraoral scanner with respect to the intraoral surface (block 734). However, if processing logic determines that visual tracking is inhibited, i.e., sufficient visual tracking is unavailable, processing logic may calculate (E) an estimated location of the intraoral scanner with respect to the intraoral surface by subtracting (D) the prediction of the motion of the intraoral surface with respect to the coordinate system, derived based on the predictive model, from (B) motion of the intraoral scanner with respect to the coordinate system as measured by the IMU. Alternatively, processing logic may otherwise calculate an estimated location of the intraoral scanner with respect to the intraoral surface based on (A) the prediction of the motion of the intraoral surface with respect to the fixed coordinate system, derived from the predictive motion model, and (B) motion of the intraoral scanner with respect to the fixed coordinate system, as measured by the IMU.

Reference is now made specifically to FIG. 7C. FIG. 7C is similar to FIG. 7B, except for blocks 773A and 773B, which take the place of block 744 in FIG. 7B. For some applications, even when visual tracking is not inhibited, the estimated location of the intraoral scanner with respect to the intraoral surface as calculated by subtracting (D) from (B) (as described above) may be used to provide an initial guess of the movement of intraoral scanner with respect to object from one frame to the next (block 773A). The visual tracking may then be used to refine the location via registration and/or stitching (block 773B). This may significantly reduce the amount of registration and/or stitching time even when the intraoral scanner is relying on visual tracking.

The determined motion and/or location of the intraoral scanner relative to the object being scanned may be used to determine the relative position and orientation between two intraoral scans that lack sufficient overlapping features for direct registration and stitching, to determine relative position and orientation between an intraoral scan and a 3D surface that lack sufficient overlapping features for direct registration and stitching, and/or to determine relative position and orientation between two 3D surfaces that lack sufficient overlapping features for direct registration and stitching in embodiments.

Methods 700, 730 and 760 enable processing logic to determine a trajectory of the scanner and apply that trajectory to intraoral scans (e.g., to extrapolate current motion of the scanner relative to a dental site during scanning, and to leverage the current motion to determine relative positions and orientations between intraoral scans and/or 3D surfaces) in embodiments. This information enables the intraoral scans and/or 3D surfaces to be registered together even in the absence of overlapping data between the intraoral scans and/or 3D surfaces. For example, if the scanner is determined to be moving at an average speed of 50 mm per second and rotating at an average speed of 10 mm per second, then an intraoral scan captured 0.1 seconds after a last intraoral scan used to generated a 3D surface was captured, then a transformation may be applied to the known position and orientation of the last intraoral scan based on the determined speed. For example, the current intraoral scan may be determined to have a position that is 5 mm offset and 1 mm rotated from the last intraoral scan.

Figure 8A:
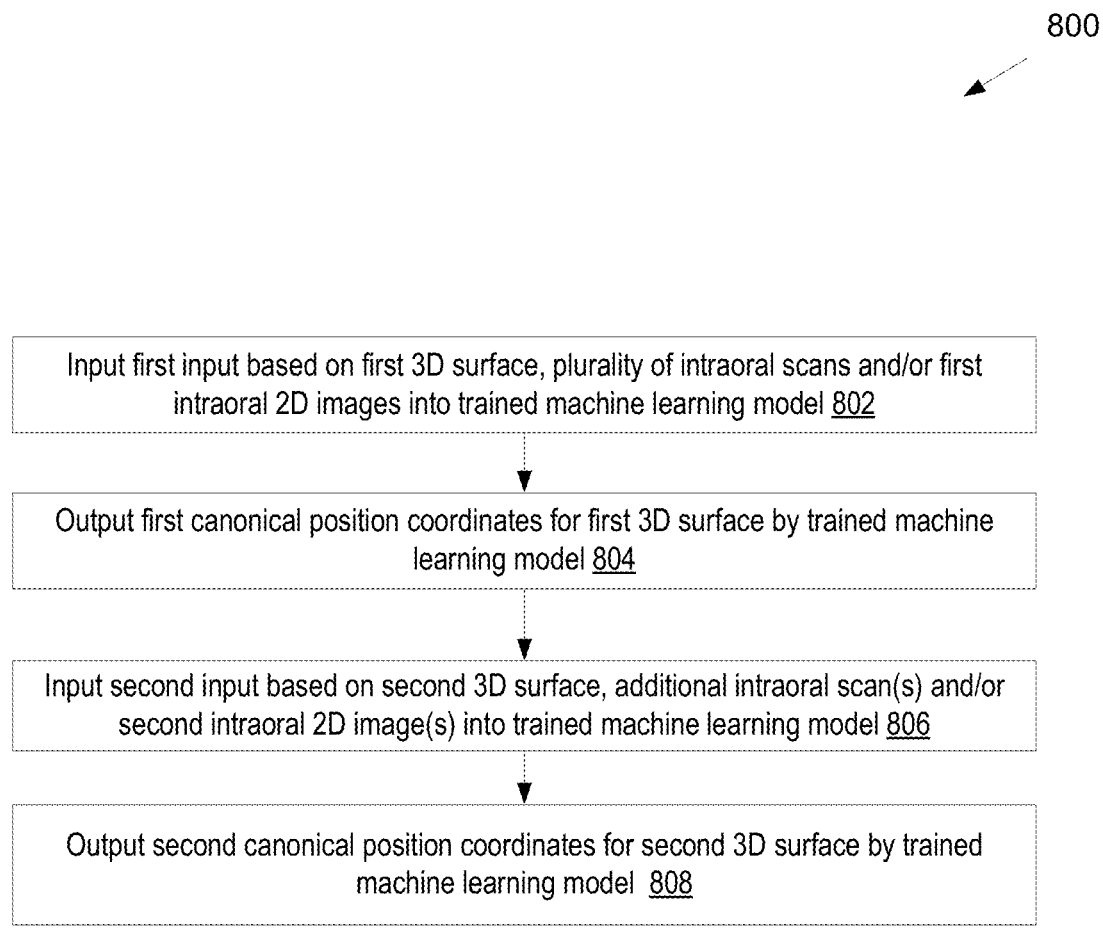
FIG. 8A illustrates a flow diagram for a method of determining relative positions and/or orientations of multiple 3D surfaces of a dental arch using a trained machine learning model, in accordance with embodiments of the present disclosure.

FIG. 8A illustrates a flow diagram for a method 800 of determining relative positions and/or orientations of multiple 3D surfaces of a dental arch using a trained machine learning model, in accordance with embodiments of the present disclosure. Method 800 may be performed, for example, to estimate relative position and/or orientation of 3D surfaces and/or intraoral scans at block 616 of method 600. In embodiments, method 700 and 800 may be performed together to increase an accuracy of an estimate for relative positions and orientations of multiple 3D surfaces.

At block 802 of method 800, processing logic inputs a first input based on a first 3D surface, a plurality of intraoral scans and/or first intraoral 2D images into a trained machine learning model. Other information such as motion data may also be input into the trained machine learning model. The trained machine learning model may have been trained to identify certain intraoral features and to determine canonical position coordinates based on such features. For example, the machine learning model may detect a cheek at a particular location, a tongue at a particular location, one or more particular tooth shapes and/or relative tooth positions, a curve of a portion of the patient's jaw, and so on. This information may together be used by the machine learning model to estimate a jaw being scanned and a position on the jaw that corresponds to current intraoral scans and/or a 3D surface. At block 804, the trained machine learning model may output first canonical position coordinates for the first 3D surface.

At block 806, processing logic inputs a second input based on a second 3D surface, one or more additional intraoral scans and/or second intraoral 2D images into the trained machine learning model. Other information such as motion data may also be input into the trained machine learning model. At block 808, the trained machine learning model may output second canonical position coordinates for the second 3D surface.

In embodiments, the first input and the second input may be input into the trained machine learning model together. This may increase an accuracy of the output canonical position coordinates for the first and second 3D surfaces. In some embodiments, the machine learning model outputs relative position and orientation information for the first and second 3D surfaces, where the relative position and orientation information is not necessarily canonical position coordinates.

Embodiments have been discussed with reference to automatically generating new 3D surfaces of dental arches from intraoral scans during intraoral scanning when those intraoral scans fail to register to existing 3D surfaces. In some examples set forth herein, the new 3D surfaces and previously generated 3D surfaces are of a same dental arch. However, it should be understood that the new 3D surfaces and previously generated 3D surfaces may also be for different dental arches. For example, a user may scan a portion of a lower dental arch of a patient and then scan a portion of an upper dental arch of the patient without following any scanning protocol or informing the intraoral scan application that the user is no longer scanning the same dental arch. Even without any such input indicating that a different dental arch is being scanned, processing logic may automatically determine that a different dental arch is being scanned, and may additionally determine relative positions and/or orientations of the 3D surfaces of each of the dental arches. Processing logic may then display the relative positions and/or orientations of the 3D surfaces for the different dental arches.

Figure 8B:
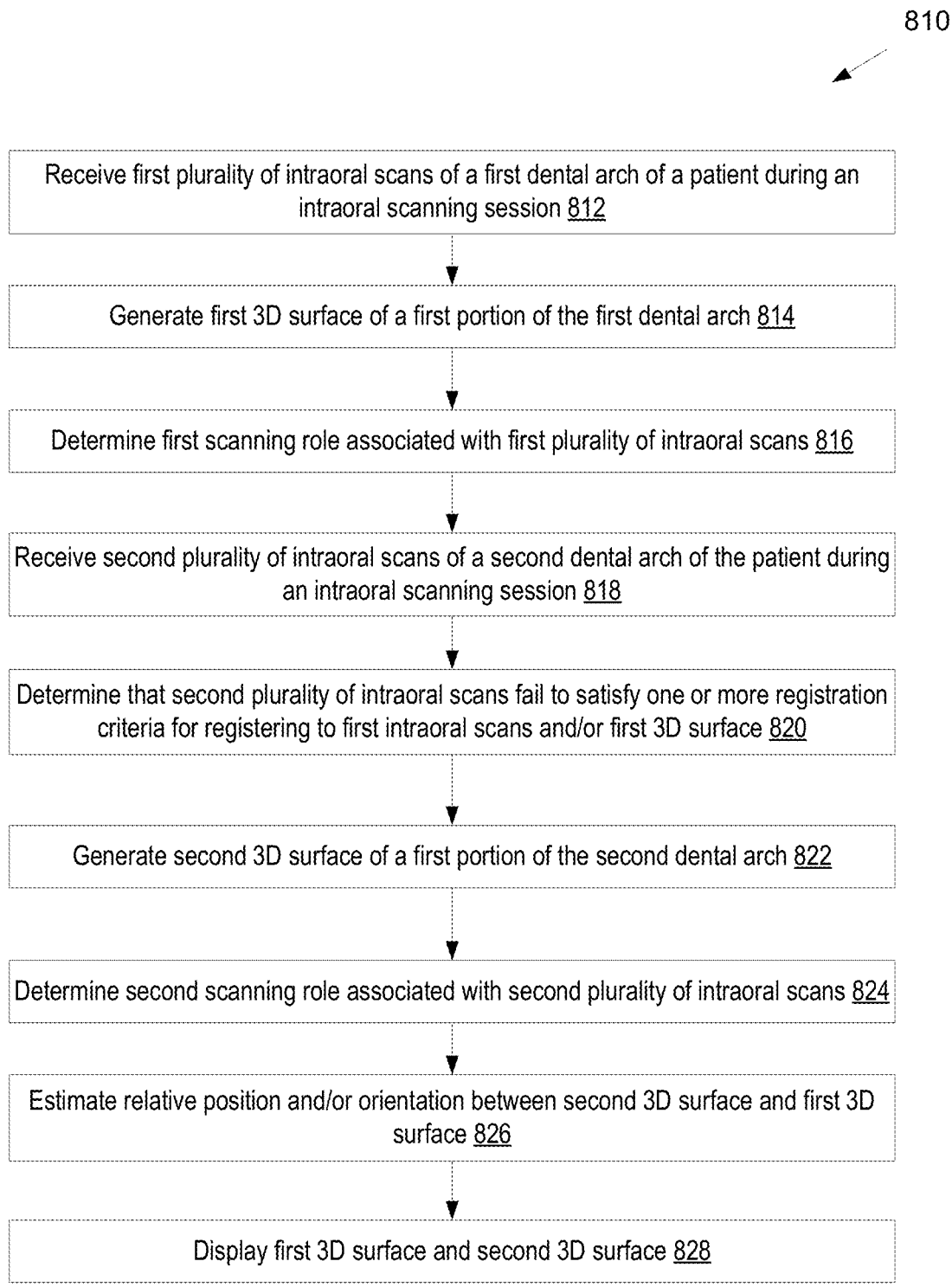
FIG. 8B illustrates a flow diagram for a method of automatically determining relative positions and/or orientations of 3D surfaces of an upper dental arch and a lower dental arch, in accordance with embodiments of the present disclosure.

FIG. 8B illustrates a flow diagram for a method 810 of automatically determining relative positions and/or orientations of 3D surfaces of an upper dental arch and a lower dental arch, in accordance with embodiments of the present disclosure. At block 812 of method 810, processing logic receives a first plurality of intraoral scans of a first dental arch of a patient during an intraoral scan session. At block 814, processing logic generates a first 3D surface of a first portion of the first dental arch using the first plurality of intraoral scans.

At block 816, processing logic determines a first scanning role associated with the first plurality of intraoral scans and/or with the first 3D surface. The first scanning role may be determined using a trained machine learning model that has been trained to identify scanning roles. For example, a machine learning model may have been trained to classify intraoral scans and/or 3D surfaces as an upper dental arch role or a lower dental arch role. Additionally, the machine learning model may have been trained to classify intraoral scans and/or 3D surfaces as an upper dental arch role, a lower dental arch role, or a bite role. The upper dental arch role indicates that scans represent an upper dental arch, the lower dental arch role indicates that scans represent a lower dental arch, and a bite role indicates that scans represent a bite showing relative positions and orientations of the upper dental arch and the lower dental arch. In one embodiment, the trained machine learning model corresponds to the trained machine learning model described in U.S. application Ser. No. 17/230,825, filed Apr. 14, 2021, which is incorporated by reference herein. One or more of the intraoral scans, the first 3D surface, and/or one or more projections of the first 3D surface onto one or more planes may be input into a trained machine learning model to determine a scanning role associated with the scans. Processing logic may detect that the first 3D surface is of the first dental arch responsive to the ML model outputting an indication that one or more scans depict the first dental arch.

In one embodiment, multiple different ML models are trained to perform scanning role classification. Each of the ML models may be trained to perform scanning role classification for a different type of input data. For example, a first ML model may be trained to perform scanning role classification for intraoral scans, a second ML model may be trained to perform scanning role classification for relatively small 3D surfaces generated from multiple intraoral scans or projections of such 3D surfaces onto planes, and a third ML model may be trained to perform scanning role classification from relatively large 3D surfaces generated from a large number of scans or projections of such 3D surfaces onto one or more planes (e.g., a projection of a 3D surface of an entire dental arch onto an occlusal plane, which may be a horizontal plane). The first ML model may determine a scanning role for intraoral scans almost immediately after the scans are generated, but without high accuracy. As further intraoral scans are generated, the second ML model may determine a scanning role for the multiple scans (e.g., for a 3D surfaces generated by stitching together the multiple scans) with higher accuracy. As still further scans are generated, the third ML model may determine a scanning role for the 3D surface with still higher accuracy. In one embodiment, a single ML model is trained to perform the operations of the above discussed first, second and third ML models.

At block 818, processing logic receives a second plurality of intraoral scans of a second dental arch of the patient during the intraoral scan session. At block 820, processing logic determines that the second plurality of intraoral scans fail to satisfy one or more registration criteria for registering to the first plurality of intraoral scans or to the first 3D surface. The registration criteria may be criteria for performing registration between scans and/or 3D surfaces based on overlapping features between those scans and/or surfaces.

At block 822, processing logic generates a second 3D surface of a first portion of the second dental arch. The first dental arch may be a first one of an upper dental arch or a lower dental arch, and the second dental arch may be a second one of the first dental arch or the second dental arch.

At block 824, processing logic determines a second scanning role associated with the second plurality of intraoral scans and/or with the second 3D surface. The second scanning role may be determined using the trained machine learning model that has been trained to identify scanning roles. One or more of the second plurality of intraoral scans, the second 3D surface, and/or one or more projections of the second 3D surface onto one or more planes may be input into a trained machine learning model to determine a scanning role associated with the second plurality of intraoral scans. Processing logic may detect that the second 3D surface is of the second dental arch responsive to the ML model outputting an indication that one or more scans depict the second dental arch.

At block 826, processing logic estimates a relative position and/or orientation between the second 3D surface of the second dental arch and the first 3D surface of the first dental arch. This may be performed, for example, by inputting the first plurality of intraoral scans, the second plurality of intraoral scans, the first 3D surface and/or the second 3D surface into a trained machine learning model that outputs canonical position information for each of the first 3D surface and the second 3D surface (or the first and second plurality of intraoral scans). In some embodiments, a single trained machine learning model outputs canonical position information for a 3D surface as well as a classification of a scanning role for that 3D surface. Accordingly, estimates of position and/or orientation of the first 3D surface may be determined at block 816, and estimates of a position and/or orientation of the second 3D surface may be determined at block 824. At block 826 the relative position and/or orientation may then be determined based on the previously determined canonical position information for the first and second 3D surfaces.

At block 828, processing logic may display the first 3D surface and the second 3D surface to a display. In one embodiment, an active 3D surface (a 3D surface associated with a most recently received intraoral scan) is shown at or near a center of the display, and the other 3D surface is shown at a bottom or side of the display. In one embodiment, the first and second 3D surface are displayed at the determined relative positions and orientations. Thus, a portion of a lower dental arch and a portion of the upper dental arch of the patient may be displayed at roughly correct positions. For example, if a doctor scans the right molars of the lower dental arch and the left molars of the upper dental arch, then a first 3D surface of the lower right molars may be shown on the lower right region of the display and a second 3D surface of the upper left molars may be shown on the upper left region of the display.

Intraoral scanning may continue, and additional intraoral scans may be received. As these additional intraoral scans are received, registration may be attempted between them and the first and second 3D surfaces. If registration is successful based on overlapping features, then the appropriate 3D surface may be updated. If registration is unsuccessful, then a third 3D surface may be generated using the additional intraoral scans. Processing logic may estimate position and/or orientation of the third 3D surface relative to the first and second 3D surfaces, where the third 3D surface may be a surface on the upper or lower dental arch. The third 3D surface may then be displayed as well. This process may continue, and any number of different 3D surfaces may be generated. The 3D surfaces may eventually be merged into fewer 3D surfaces (e.g., one for the upper dental arch and one for the lower dental arch) as additional intraoral scans are received.

Figure 9:
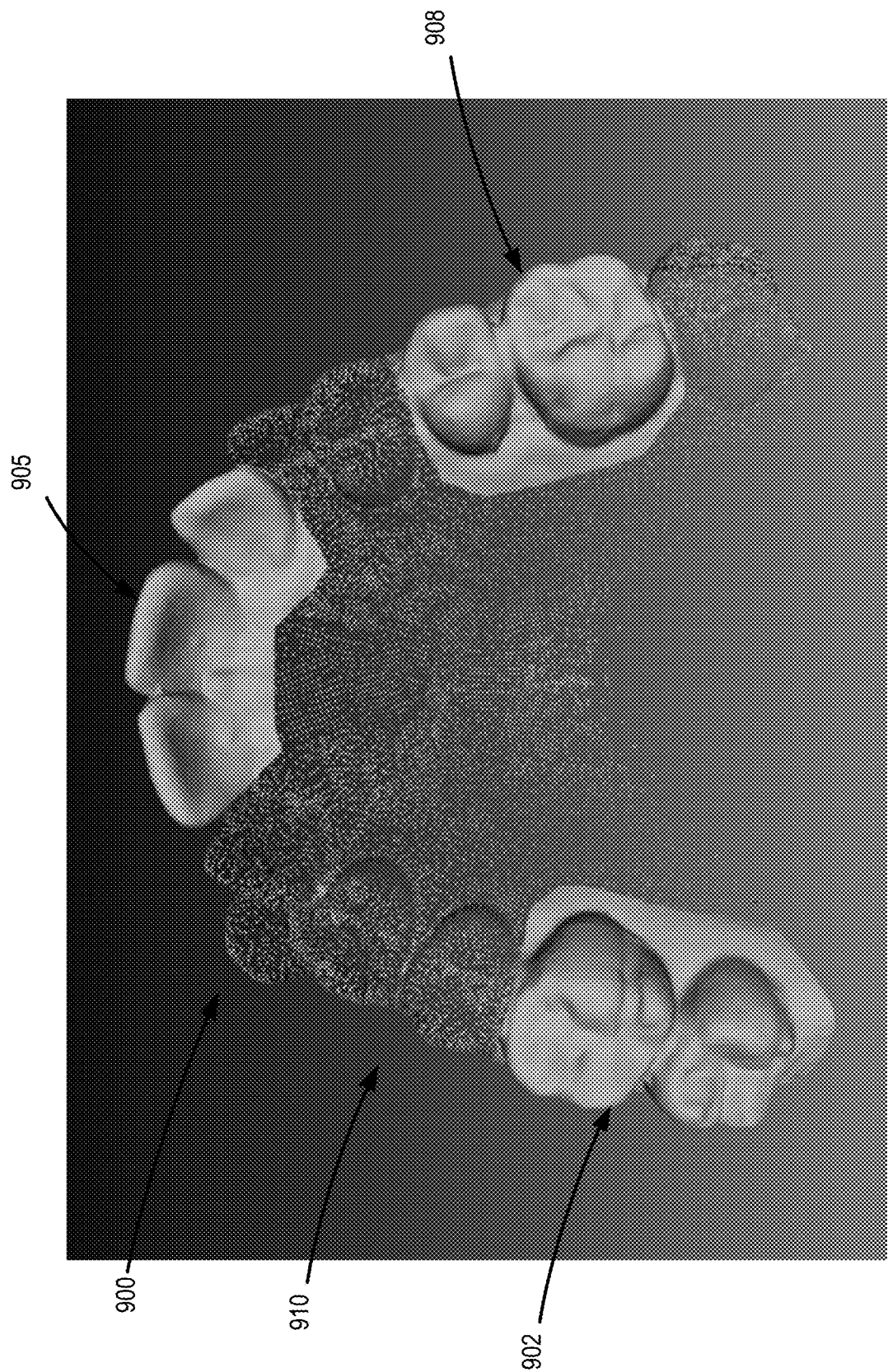
FIG. 9 illustrates relative positions and orientations of multiple 3D surfaces of a dental arch, in accordance with embodiments of the present disclosure.

FIG. 9 illustrates a view of a GUI for an intraoral scan application 900 that shows relative positions and orientations of multiple 3D surfaces 902, 906, 908 of a dental arch, in accordance with embodiments of the present disclosure. Also shown are estimated approximate shapes and positioning of further 3D surfaces 910 of a dental arch. As shown, the 3D surfaces 902, 906, 908 do not overlap. In other embodiments, one or more of the 3D surfaces may overlap, but there may be insufficient information to register the 3D surfaces together based on (or based solely on) the overlapping data.

Figure 10:
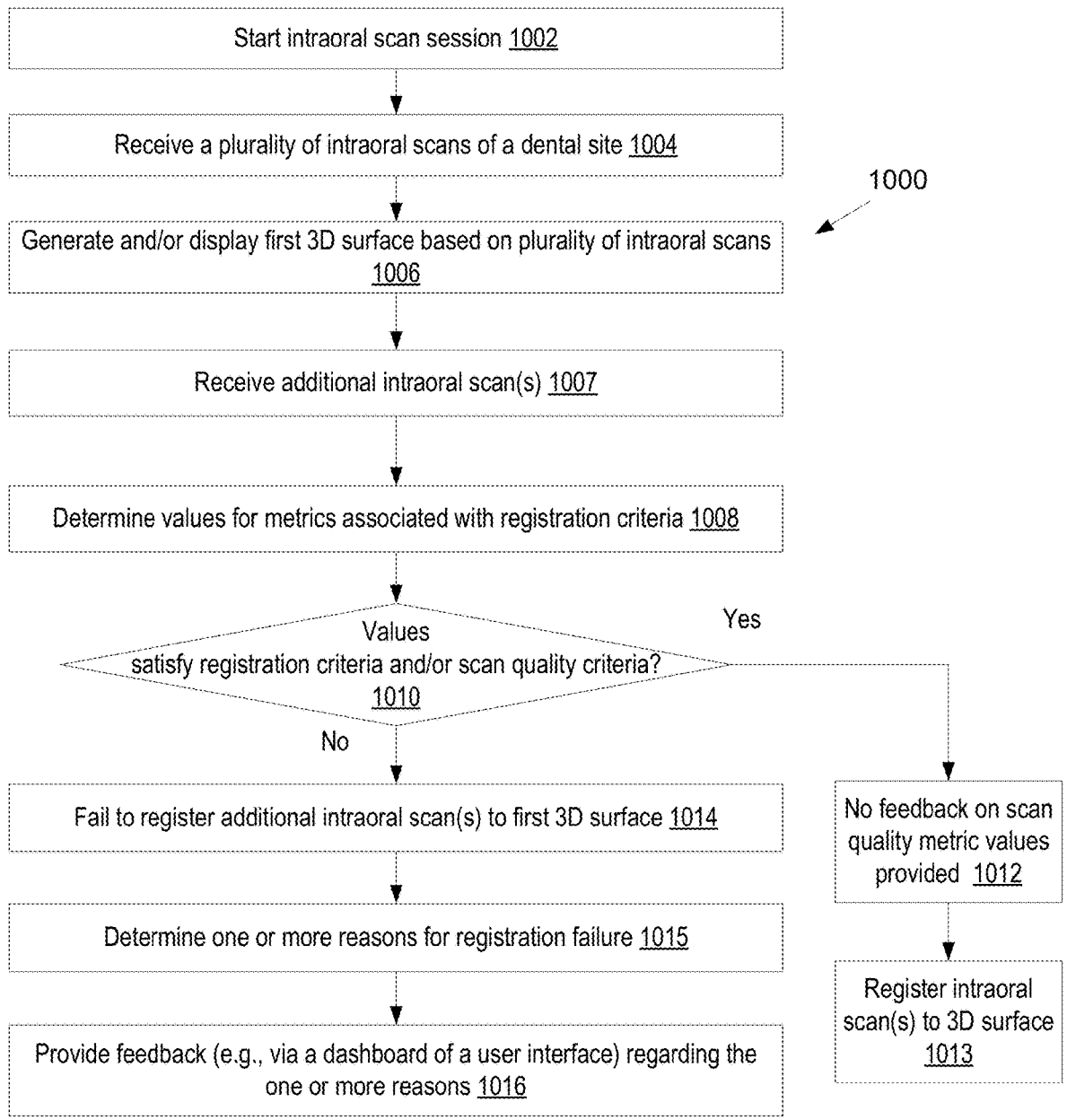
FIG. 10 illustrates a flow diagram for a method of assessing intraoral scans and providing feedback of the intraoral scans during an intraoral scanning procedure, in accordance with embodiments of the present disclosure.

FIG. 10 illustrates a flow diagram for a method 1000 of assessing intraoral scans and providing feedback of the intraoral scans during an intraoral scanning procedure, in accordance with embodiments of the present disclosure. At block 1002 of method 1000, an intraoral scan session may be started. This may occur when a doctor inserts an intraoral scanner into a patient's mouth and begins generating intraoral scans. The intraoral scan session may proceed until enough intraoral scans have been captured to generate a 3D model of a dental site of the patient (e.g., of the patient's upper and/or lower dental arch). At block 1004, processing logic receives a plurality of intraoral scans of a dental site (e.g., dental arch, tooth, group of teeth, etc.). At block 1006, processing logic registers the intraoral scans together using one or more registration algorithm that relies upon overlapping features of the intraoral scans, and stitches the registered intraoral scans together to generate a 3D surface representing a portion of the dental site that has been scanned thus far. As further intraoral scans are received, they may be registered to the 3D surface and stitched to the 3D surface to update the 3D surface. This 3D surface may be output to a display and updated in real time or near-real time as intraoral scans are received and stitched together.

At block 1007, processing logic may receive one or more additional intraoral scans.

At block 1008, processing logic determines, for one or more of the plurality of intraoral scans and/or of the additional intraoral scans, values for one or more scan quality metrics associated with registration criteria and/or with scan quality. Scan quality metric values may include a data density value, a scan distance value, a scan speed value, a scanner cleanliness value, a moving tissue value, an angle value, a blood/saliva value, and soon.

At block 1010, processing logic may determine whether the scan quality metric values associated with the additional intraoral scans satisfy one or more registration criteria. The registration criteria may be registration criteria for registering intraoral scans and/or 3D surfaces based on overlapping features. Alternatively, or additionally, processing logic may determine whether one or more of the scan quality metric values for any of the intraoral scans satisfy one or more other criteria, such as scan quality criteria. Scan quality scores may also be determined from the scan quality metric values, and may be compared to scan quality criteria. If the scan quality metric values or scores satisfy scan quality metric criteria (and/or registration criteria), the method may proceed to block 1012.

In one embodiment, multiple scan quality metric values are used to generate one or more scan quality score. For example, a scan quality score may be determined using a combination of two or more scan quality metric values. In one embodiment, if the scan quality score is above a scan quality threshold, the method proceeds block 1012.

At block 1012, processing logic may not provide any feedback on scan quality metric values. If the scan quality metric values of the additional intraoral scans satisfied registration criteria, they may registered to the plurality of intraoral scans and/or to the first 3D surface at block 1013.

If at block 1010 the scan quality metric values (and/or scan quality score(s)) fail to satisfy scan quality metric criteria (or fail to satisfy registration criteria), the method may proceed to block 1014. For example, the scan quality score may be compared to a scan quality threshold. In one embodiment, if the scan quality score is below the scan quality threshold, then processing logic may proceed to block 1014.

At block 1014, processing logic may fail to register the additional intraoral scan(s) to the first 3D surface based on overlapping features. At block 1015, processing logic may determine one or more reasons for the registration failure (e.g., one or more reasons that the scan quality score was below the scan quality threshold) based on the scan quality metric values and the scan registration criteria. For example, processing logic may determine which, if any, of the scan quality metric values fell outside of an acceptable range of values. In an example, processing logic may determine that a window of the scanner is too dirty, that there is too much moving tissue being detected, that there is too much blood/saliva, that the scanner is moving too fast, that the scanner is too far from a scanned surface, and so on. At block 1016, processing logic provides feedback regarding the one or more reasons that the registration failed. The feedback may include the scan quality metric values and/or score(s) computed based on the scan quality metric values. This may enable a user to adjust their scanning technique (e.g., to move the scanner closer to a dental arch, to slow down movement of the scanner, to wipe blood/saliva from a patient's teeth, to replace a protective sleeve of the scanner and/or wipe a window/mirror of the scanner, and so on.

Figure 11:
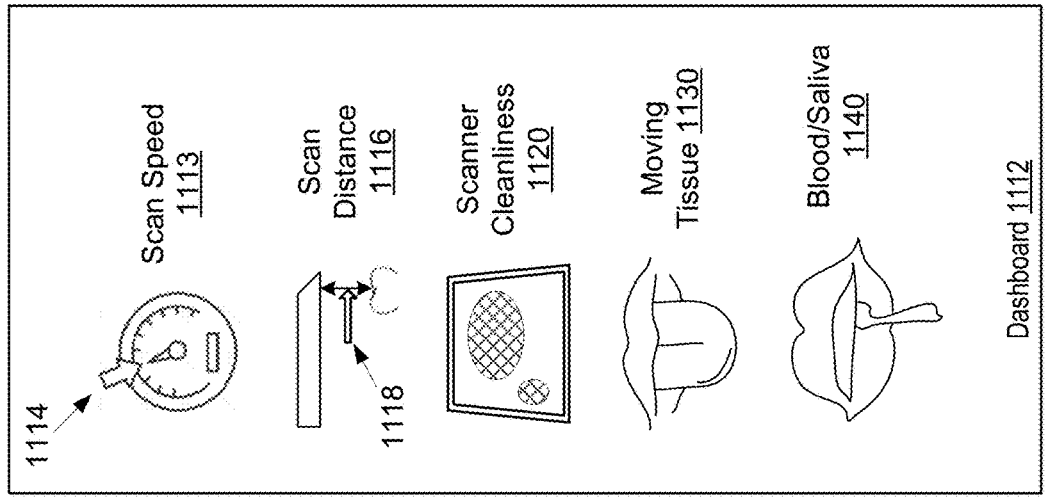
FIG. 11 illustrates a user interface of an intraoral scan application showing a 3D surface and a dashboard indicating various scan quality and/or registration metrics, in accordance with embodiments of the present disclosure.
Figure 11:
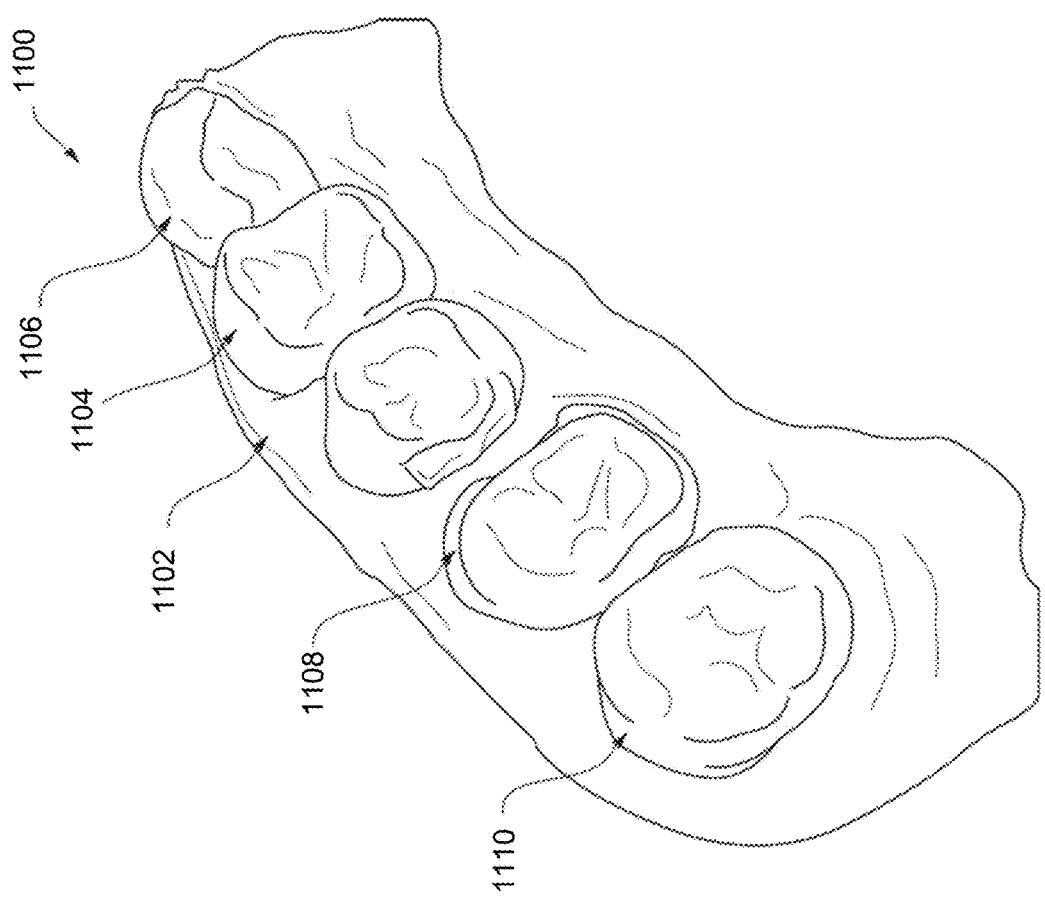

FIG. 11 illustrates a user interface of an intraoral scan application showing a 3D surface 1100 and a dashboard 1112 indicating various scan quality and/or registration metrics, in accordance with embodiments of the present disclosure. As shown, the 3D surface 1100 includes a scanned gingiva 1102 and scanned teeth 1104, 1106, 1108, 1110. The dashboard 1112 shows icons and/or values or scores for one or more scan quality metrics, including a scan speed metric 1113, a scan distance metric 1116, a scanner cleanliness metric 1120, a moving tissue metric 1130 and a blood/saliva metric 1140. Icons and/or values for individual scan quality metrics may or may not be shown depending on the associate values of those scan quality metrics and/or scores computed based on those values. For example, when a value for a particular scan quality metric begins to approach a threshold, then the icon associated with that scan quality metric may be displayed, optionally with a detected value. As the value for the particular scan quality metric gets closer to the threshold, reaches the threshold and/or passes the threshold, a representation of the icon and/or value for that scan quality metric may change. This may include a change in size of the icon for the scan quality metric, a change in color, a change in blinking speed, a change in whether or not the icon is blinking, a change in brightness, and so on. As the value reaches a threshold distance from the threshold of the scan quality metric, the icon and/or value may no longer be displayed in the dashboard. Alternatively, scan quality metric values and/or icons may always be shown in the dashboard. This may be user selectable. In some embodiments, threshold values for one or more of the scan quality metrics, such as a scan speed threshold 1114 and a scan distance threshold 1116 may be shown in the dashboard 1112. This may provide a visual indicator of how close or far scans are from the respective thresholds.

In additional to assessing scan quality metrics for intraoral scans during intraoral scanning, an intraoral scan application in embodiments may assess scan quality metrics for various regions of a 3D surface and/or 3D model generated from multiple intraoral scans.

Figure 12:
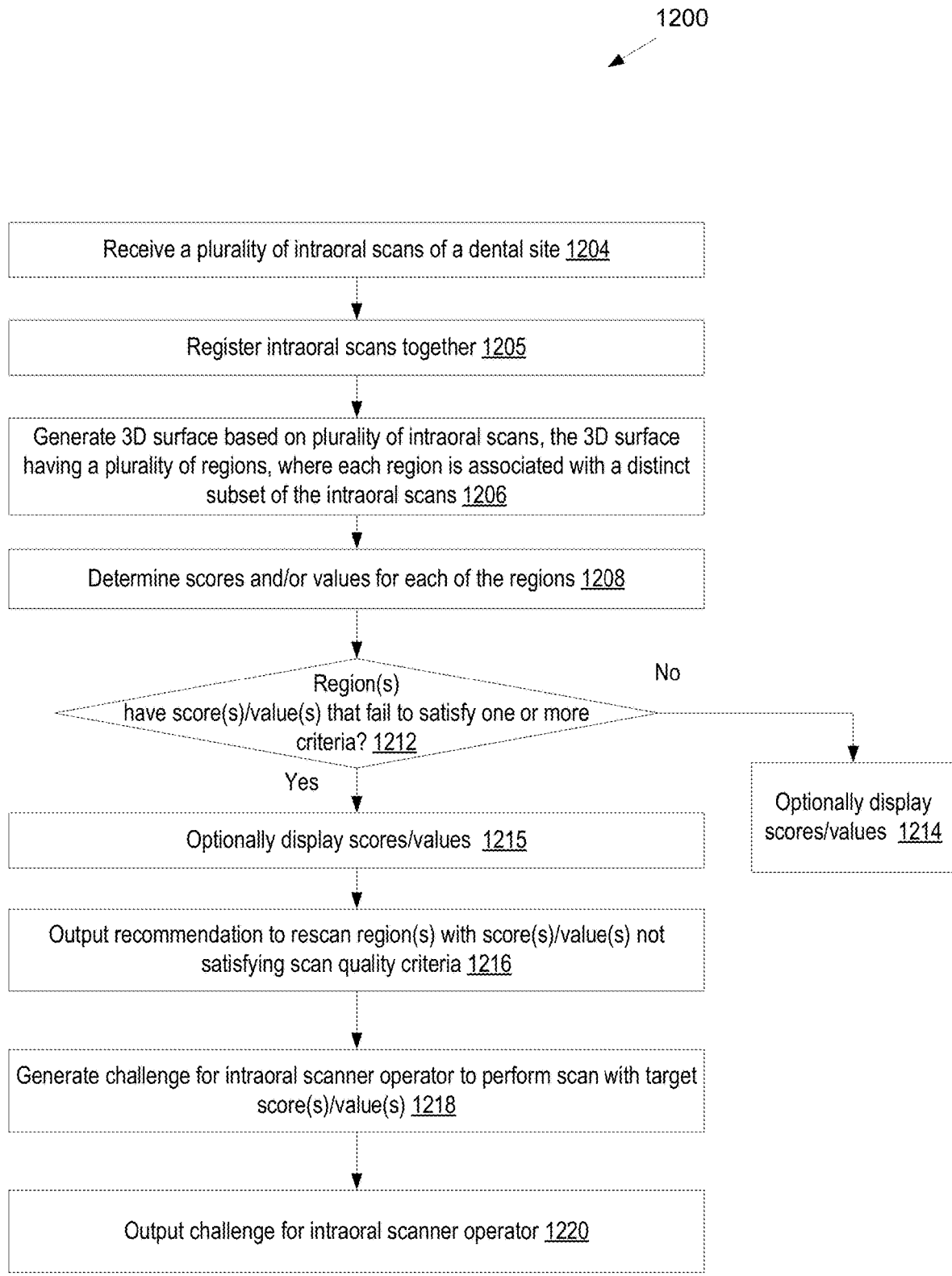
FIG. 12 illustrates a flow diagram for a method of assessing a 3D surface and providing feedback identifying regions of the 3D surface to rescan, in accordance with embodiments of the present disclosure.

FIG. 12 illustrates a flow diagram for a method 1200 of assessing a 3D surface or 3D model and providing feedback identifying regions of the 3D surface or 3D model to rescan, in accordance with embodiments of the present disclosure. At block 1204 of method 1200, processing logic receives a plurality of intraoral scans of a dental site. At block 1205, processing logic registers the intraoral scans together using any one or more of the techniques described herein. At block 1206, processing logic generates a 3D surface based on the plurality of intraoral scans. The 3D surface may have a plurality of regions, where each region may be associated with a distinct subset of the intraoral scans. In one embodiment, the 3D surface is a 3D model of a dental site.

At block 1208, processing logic determines scan quality metric values and/or scores for each of the regions of the 3D surface/3D model. The values and/or scores may be determined based on the 3D surface regions themselves and/or on information about intraoral scans used to generate the regions of the 3D surface. The values and/or scores may include, for example, a scan speed score and/or value, a scan distance score and/or value, a moving tissue score and/or value, a scanner cleanliness score and/or value, a blood/saliva score and/or value, a data density score and/or value, and so on. In one embodiment, scores are determined based on aggregated scan quality metric values of multiple intraoral scans used to generate regions of the 3D surface/3D model. For example, a particular region of the 3D surface may have been generated using 40 intraoral scans. Processing logic may determine a percentage of the 40 intraoral scans that had scan quality metric values that failed to satisfy one or more criteria. If the determined percentage of intraoral scans associated with a region of the 3D surface having scan quality metric values that failed to satisfy one or more scan quality criteria exceeds a threshold, then the region of the 3D surface may be flagged or identified for attention by the doctor. In one embodiment, processing logic makes separate determinations for each scan quality metric for a region. If a determined percentage of intraoral scans associated with a region of the 3D surface having a value for a scan quality metric that failed to satisfy one or more scan quality criteria exceeds a threshold, then the region of the 3D surface may be flagged or identified as failing a particular scan quality criteria associated with that scan quality metric. For example, if a threshold percentage of intraoral scans associated with a region had a scan speed that exceeded a scan speed threshold, then the region of the 3D surface may be flagged with an excessive scan speed indicator. Similarly, if a threshold percentage of intraoral scans associated with a region had a scan distance that exceeded a scan distance threshold, then the region of the 3D surface may be flagged with an excessive scan distance indicator.

At block 1212, processing logic determines whether any regions have scores and/or values that fail to satisfy one or more criteria (e.g., that exceed a threshold for values meant to be below the threshold), that are below a threshold (for values meant to exceed the threshold), and so on). For regions that satisfy all scan quality criteria, the method proceeds to block 1214 and scores and/or values for those regions may be displayed. For regions that fail to satisfy one or more criteria, the method continues to block 1215.

At block 1215, processing logic may display one or more of the scores nan/or values. In some embodiments, only those scores and/or values failing to satisfy scan quality criteria are displayed. At block 1216, processing logic may display or otherwise output a recommendation to rescan those regions with scores and/or values that fail to satisfy one or more of the scan quality criteria. A user may then proceed to rescan those regions of a dental arch associated with the regions of the 3D surface/3D model with the non-conforming or out-of-specification scores and/or values.

In some embodiments, processing logic may provide gamification of intraoral scanning. For example, processing logic may determine scan quality metric values or scores associated with one or more 3D surfaces and/or 3D models generated based on scans performed by a user. Processing logic may determine which scan quality metrics of intraoral scans generated by a user tend not to meet scan quality criteria. Processing logic may then provide incentives for the user to generate scans with improved scan quality metrics.

In one embodiment, at block 1218 processing logic may generate a challenge for an operator of the intraoral scanner. The challenge may be a challenge to perform an intraoral scan and generate a 3D surface/3D model with scores and/or scan quality metric values that are within a target range. The challenge may be specific to the operator, and may be generated based on past scanning performance of that operator. For example, if the operator tends to generate scans with scan speeds that are too high, then the challenge may be a challenge to complete intraoral scanning of a patient with no intraoral scans that exceed a scan speed threshold. At block 1220, the challenge may be output to the intraoral scanner operator. The operator may be awarded points for completing challenges, and may receive prizes based on awarded points. In embodiments, scores and/or scan quality metric values may be generated for multiple operators (e.g., who might share a dental office) based on the intraoral scans that they perform, and awards may be given to those operators with highest scores (and/or optimal values). Such scores may be based on an amount of percentage of intraoral scans during an intraoral scanning session that satisfy scan quality criteria. In embodiments, different scores may be provided for different scan quality metrics. Other prizes may also be awarded based on degree of improvement. For example, an operator with a biggest improvement may be awarded a prize even if they don't have the highest score. In embodiments, a framework may be implemented in which operators start at level 1 and go up in level as their scanning improves. Operators may compete with other operators at the same or similar levels in embodiments.

Figure 13:
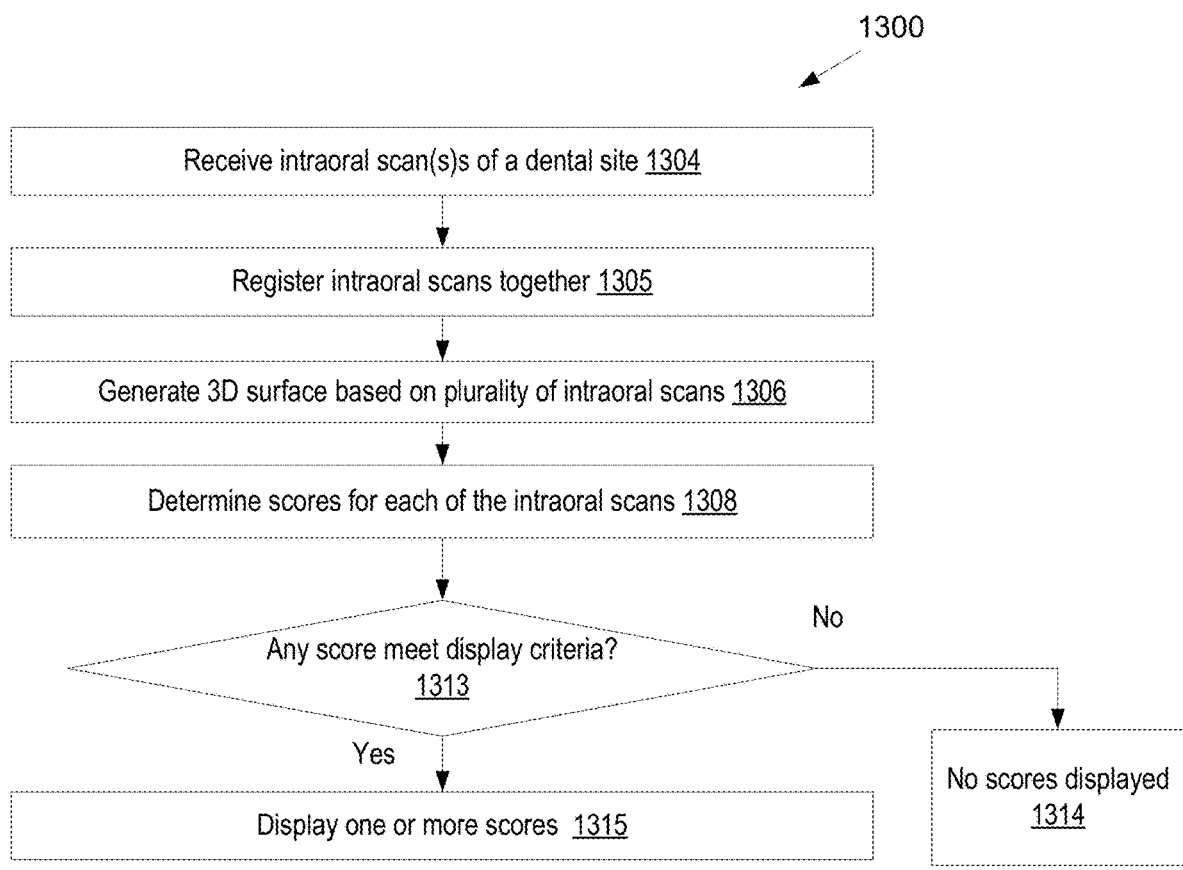
FIG. 13 illustrates a flow diagram for a method of assessing a 3D surface and providing feedback identifying regions of the 3D surface to rescan, in accordance with embodiments of the present disclosure.

FIG. 13 illustrates a flow diagram for a method 1300 of assessing intraoral scans and providing feedback identifying a result of such assessment, in accordance with embodiments of the present disclosure. At block 1304 of method 1300, processing logic receives one or more intraoral scans of a dental site. At block 1305, processing logic may register the intraoral scans to other intraoral scans and/or to one or more 3D surfaces. At block 1306, processing logic may generate or update a 3D surface based on the intraoral scan(s).

At block 1308, processing logic determines scores and/or scan quality metric values for each of the intraoral scans. The scores and/or values may include, for example, a scan speed score and/or value, a scan distance score and/or value, a moving tissue score and/or value, a scanner cleanliness score and/or value, a blood/saliva score and/or value, a data density score and/or value, and so on.

At block 1313, processing logic determines whether intraoral scans have scores and/or value that fail to satisfy one or more display criteria. The display criteria may include first scan quality criteria (e.g., one or more thresholds). Scores and/or value that fail to satisfy the first scan quality criteria may result in intraoral scans having those scores being rejected. The display criteria may also include second scan quality criteria. The second scan quality criteria may have different thresholds than the first scan quality criteria, but may not be indicative of rejected intraoral scans. Scans with scores that fail to satisfy the second scan quality criteria may be close to failing, for example. In an example, a first scanner dirtiness threshold may be 50% dirty, and a second lesser dirtiness threshold may be 30% dirty. A scanner cleanliness score may have a value of 35% (indicating that 35% of an optical surface is dirty), and thus may satisfy a first scanner cleanliness criterion associated with the first scanner dirtiness threshold but may fail to satisfy a second scanner cleanliness criterion associated with the second scanner dirtiness threshold. For intraoral scans that meet the display criteria, the method proceeds to block 1315 and one or more of the scores and/or value are displayed.

Figure 14:
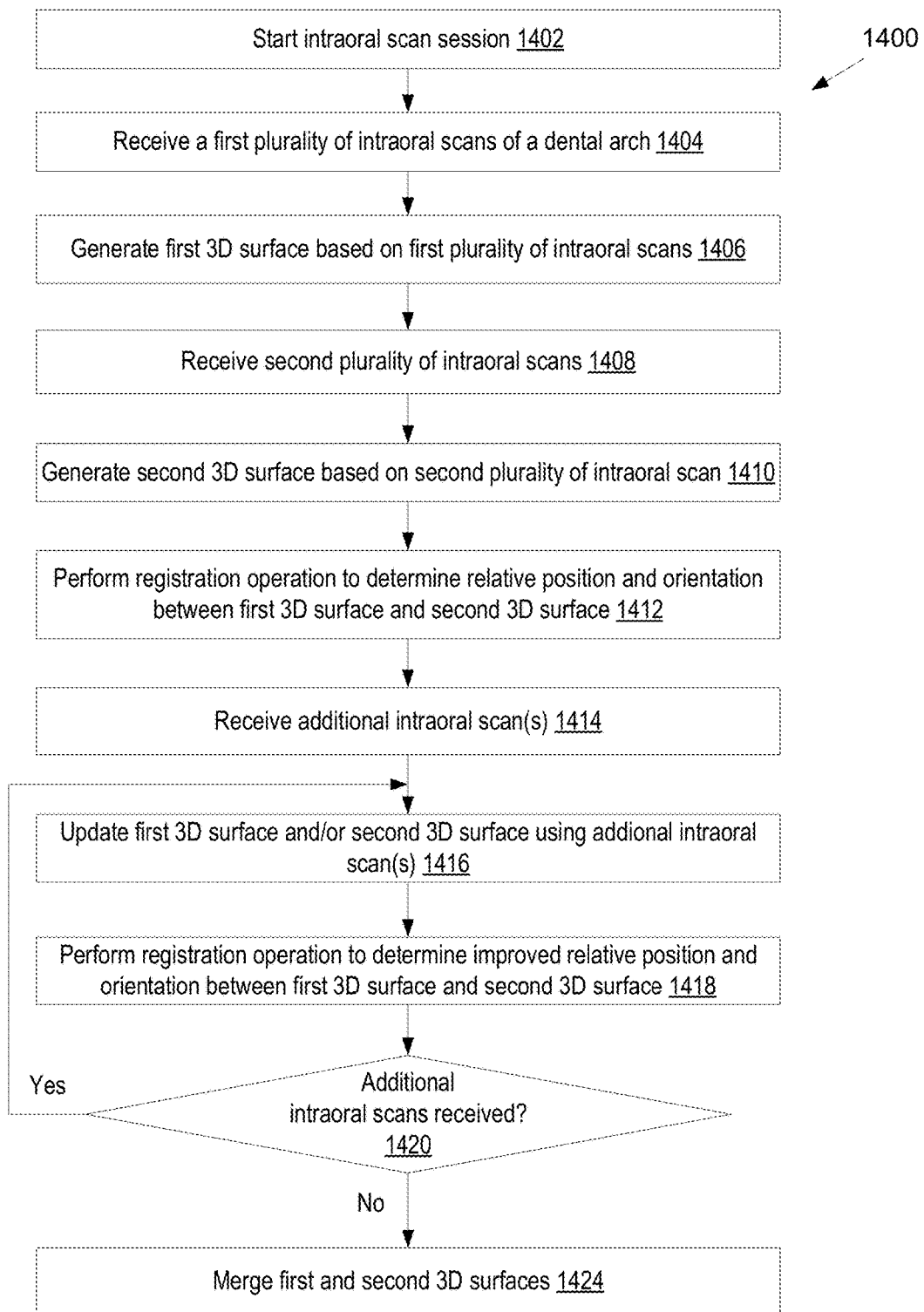
FIG. 14 illustrates a flow diagram for a method of continuously improving an accuracy of relative positions and/or orientations of multiple 3D surfaces of a dental arch during intraoral scanning, in accordance with embodiments of the present disclosure.

FIG. 14 illustrates a flow diagram for a method 1400 of continuously improving an accuracy of relative positions and/or orientations of multiple 3D surfaces of a dental arch during intraoral scanning, in accordance with embodiments of the present disclosure. At block 1402 of method 1400, an intraoral scan session may be started. This may occur when a doctor inserts an intraoral scanner into a patient's mouth and begins generating intraoral scans. The intraoral scan session may proceed until enough intraoral scans have been captured to generate a 3D model of a dental site of the patient (e.g., of the patient's upper and/or lower dental arch). At block 1404, processing logic receives a first plurality of intraoral scans of a dental site (e.g., dental arch, tooth, group of teeth, etc.). At block 1406, processing logic registers the first plurality of intraoral scans together using one or more registration algorithm that relies upon overlapping features of the first plurality of intraoral scans, and stitches the registered intraoral scans together to generate a first 3D surface representing a first portion of the dental site that has been scanned thus far.

At block 1408, processing logic receives a second plurality of intraoral scans of the dental site (e.g., dental arch, tooth, group of teeth, etc.). Processing logic may determine that the second plurality of intraoral scan do not register to the first 3D surface by a registration algorithm that relies upon overlapping features between the second plurality of intraoral scans and the first 3D surface.

At block 1410, processing logic registers the second plurality of intraoral scans together using one or more registration algorithm that relies upon overlapping features of the first plurality of intraoral scans, and stitches the registered second plurality of intraoral scans together to generate a second 3D surface representing a second portion of the dental site.

At block 1412, processing logic performs a registration operation to determine a relative position and orientation between the first 3D surface and the second 3D surface. One or more registration techniques may be performed to determine the relative position and orientation between the first and second 3D surfaces.

In one embodiment, a registration technique relies upon registering the first 3D surface and the second 3D surface to a previously generated 3D model of the patient's dental arch. For example, processing logic may determine that a previously generated 3D model of the patient's dental arch is existent, and may then register the first and second 3D surfaces to that previously generated 3D model. Alternatively, processing logic may determine that previously generated intraoral scans from a prior patient visit or earlier in a current patient visit are existent, and may generate a 3D model from such previously generated intraoral scans. Processing logic may then register the first and second 3D surfaces to that 3D model.

In one embodiment, a registration technique uses motion data that indicates a motion of an intraoral scanner between the generation of one or more intraoral scans used to generate the first 3D surface and the generation of one or more intraoral scans used to generate the second 3D surface to determine the relative position and orientation of the first and second 3D surfaces. The motion data may be generated by an IMU of the scanner and/or may be determined based on analyzing multiple scans and/or 2D images and determining an amount of movement of the scanner along one or more axes and/or rotation of the intraoral scanner about one or more axes based on the analysis.

In one embodiment, a registration technique uses a trained machine learning model to determine relative position and orientation of the first and second 3D surfaces. The first plurality of intraoral scans, the second plurality of intraoral scans, the first 3D surface, the second 3D surface, projections of the first 3D surface onto one or more planes and/or projections of the second 3D surface onto one or more planes may be input into the trained machine learning model, which may output the relative position and orientation of the first and second 3D surfaces (e.g., as canonical position information). Motion data may also be input into the trained machine learning model along with the other input data.

In one embodiment, multiple registration techniques are used, and position and orientation of the first and second 3D surfaces are estimated based on outputs of the multiple registration techniques. For example, the results of the multiple registration techniques may be averaged with a weighted or unweighted average.

In one embodiment, a registration technique uses registration between 2D images to estimate registration between associated intraoral scans, as discussed above.

At block 1414, processing logic may receive one or more additional intraoral scans. At block 1416, processing logic registers the one or more additional intraoral scans to the first 3D surface and/or the second 3D surface based on overlapping features between the one or more additional intraoral scans and the first and/or second 3D surface.

At block 1418, processing logic repeats the registration process performed at block 1412. The registration process is repeated using the updated 3D surfaces, which include additional information. This results in a higher accuracy estimate of the relative position and orientation of the first and second 3D surfaces.

At block 1420, processing logic determines if additional intraoral scans are received. If so, the method returns to block 1416, and the operations of blocks 1416, 1418 and 1420 are repeated. Otherwise, the method proceeds to block 1424, at which the first and second 3D surfaces may be merged into a single 3D surface based on overlapping features between these surfaces. A 3D model may then be generated based on the intraoral scans used to generate the single 3D surface.

Note that method 1400 is discussed with reference to two 3D surfaces. However, three, four or even more 3D surfaces may be generated using method 1400. As sufficient information to merge 3D surfaces is received, the multiple 3D surfaces may be merged and the total number of 3D surfaces may be reduced until there is a single 3D surface for a dental site (e.g., a dental arch). Additionally, any discussion herein directed to two 3D surfaces also applies to more than two 3D surfaces. For example, a trained machine learning model may be used to estimate the relative positions and orientations of three, four, five, etc. 3D surfaces.

Figure 15:
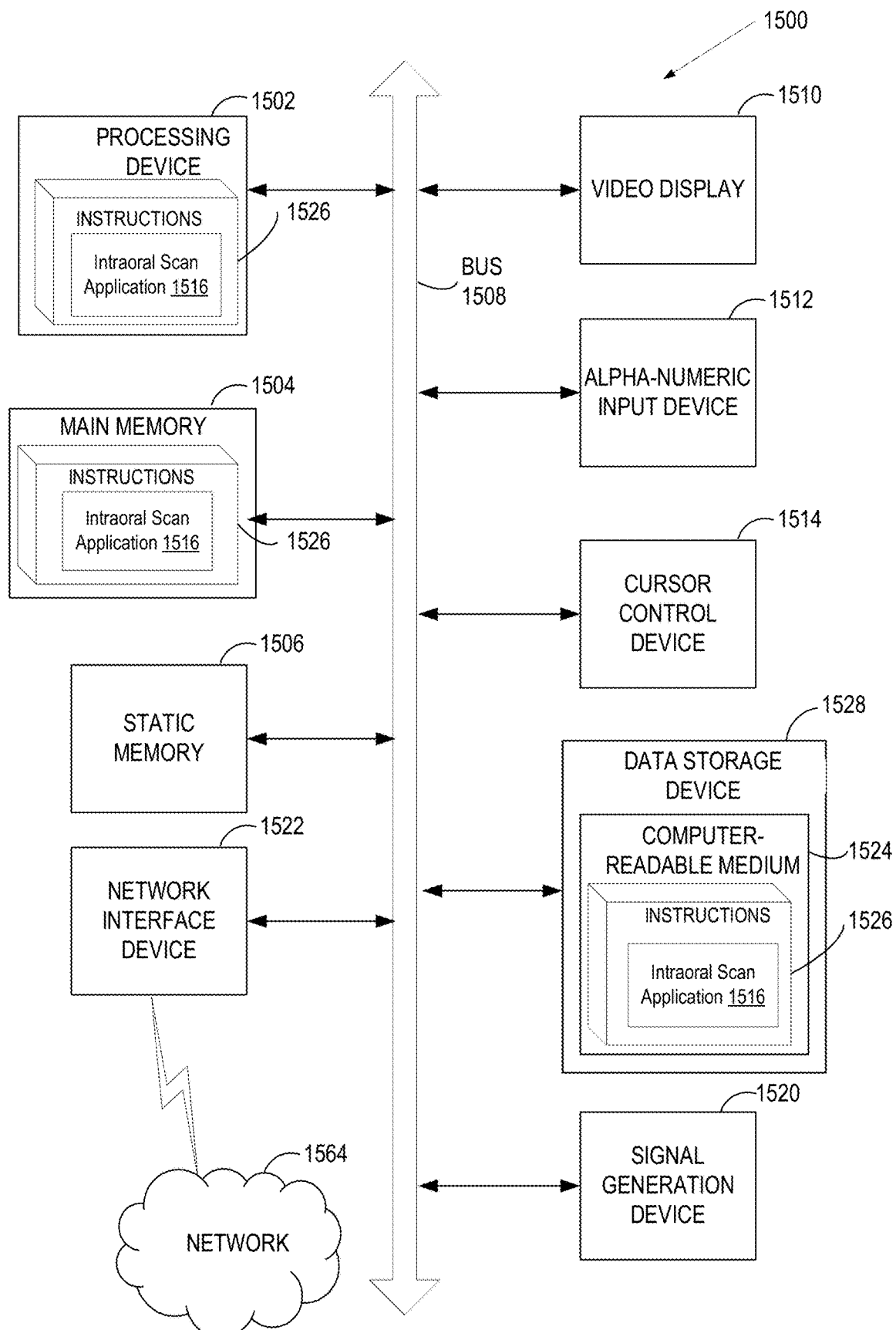
FIG. 15 illustrates a block diagram of an example computing device, in accordance with embodiments of the present disclosure.

FIG. 15 illustrates a diagrammatic representation of a machine in the example form of a computing device 1500 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 1500 includes a processing device 1502, a main memory 1504 (e.g., read-only memory (ROM), flash memory, dynamic random access memory (DRAM) such as synchronous DRAM (SDRAM), etc.), a static memory 1506 (e.g., flash memory, static random access memory (SRAM), etc.), and a secondary memory (e.g., a data storage device 1528), which communicate with each other via a bus 1508.

Processing device 1502 represents one or more general-purpose processors such as a microprocessor, central processing unit, or the like. More particularly, the processing device 1502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1502 may also be one or more special-purpose processing devices such as an application specific integrated circuit (ASIC), a field programmable gate array (FPGA), a digital signal processor (DSP), network processor, or the like. Processing device 1502 is configured to execute the processing logic (instructions 1526) for performing operations and steps discussed herein.

The computing device 1500 may further include a network interface device 1522 for communicating with a network 1564. The computing device 1500 also may include a video display unit 1510 (e.g., a liquid crystal display (LCD) or a cathode ray tube (CRT)), an alphanumeric input device 1512 (e.g., a keyboard), a cursor control device 1514 (e.g., a mouse), and a signal generation device 1520 (e.g., a speaker).

The data storage device 1528 may include a machine-readable storage medium (or more specifically a non-transitory computer-readable storage medium) 1524 on which is stored one or more sets of instructions 1526 embodying any one or more of the methodologies or functions described herein. A non-transitory storage medium refers to a storage medium other than a carrier wave. The instructions 1526 may also reside, completely or at least partially, within the main memory 1504 and/or within the processing device 1502 during execution thereof by the computer device 1500, the main memory 1504 and the processing device 1502 also constituting computer-readable storage media.

The computer-readable storage medium 1524 may also be used to store an intraoral scan application 1516, which may correspond to the similarly named component of FIG. 1. The computer readable storage medium 1524 may also store a software library containing methods for an intraoral scan application 1550. While the computer-readable storage medium 1524 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. An intraoral scanning system, comprising:
   an intraoral scanner, configured to generate a plurality of intraoral scans during an intraoral scanning session; and
   a computing device, wherein the computing device is to:
   receive the plurality of intraoral scans during the intraoral scanning session;
   register the plurality of intraoral scans together based on overlapping features of the plurality of intraoral scans;
   generate a first three-dimensional (3D) surface based on the plurality of intraoral scans;
   receive one or more additional intraoral scans;
   determine that the one or more additional intraoral scans fail to satisfy one or more registration criteria for registering to at least one of the plurality of intraoral scans or the first 3D surface;
   generate a second 3D surface based on the one or more additional intraoral scans without interrupting the intraoral scanning session;
   estimate, after failing to satisfy the one or more registration criteria, a position and orientation of the second 3D surface relative to the first 3D surface without successful registration of the second 3D surface or the first 3D surface to historical scan data and based at least in part on use of a trained machine learning model; and
   output the first 3D surface and the second 3D surface to a display, wherein the second 3D surface is output with the estimated position and orientation relative to the first 3D surface.

2. The intraoral scanning system of claim 1, wherein the computing device is further to:
   receive a plurality of additional intraoral scans;
   register the plurality of additional intraoral scans to the one or more additional intraoral scans;
   update the second 3D surface based on the plurality of additional intraoral scans; and
   determine an update to the position and orientation of the second 3D surface relative to the first 3D surface, wherein the update increases an accuracy of the relative position and orientation of the second 3D surface and the first 3D surface.

3. The intraoral scanning system of claim 1, wherein the computing device is further to:

receive movement data from an intraoral scanner that generated the plurality of intraoral scans and the one or more additional intraoral scans, wherein the movement data indicates an amount of movement of the intraoral scanner between generation of a first intraoral scan of the plurality of intraoral scans and a second intraoral scan of the one or more additional intraoral scans; and determine at least one of a position or orientation of the second 3D surface relative to the first 3D surface based at least in part on the movement data.

4. The intraoral scanning system of claim 3, wherein the movement data is generated by an inertial measurement unit of the intraoral scanner, wherein the orientation of the second 3D surface relative to the first 3D surface is determined based on the movement data, and wherein the computing device is further to:

receive a plurality of two-dimensional (2D) images during the intraoral scanning session, wherein each of the plurality of 2D images is associated with one of the plurality of intraoral scans or one of the one or more additional intraoral scans;

estimate a position change between at least a first scan of the plurality of intraoral scans and the one or more additional intraoral scans using two or more of the plurality of 2D images; and determine a position of the second 3D surface relative to the first 3D surface based on the estimated position change.

5. The intraoral scanning system of claim 1, wherein the computing device is further to:

receive a plurality of two-dimensional (2D) images during the intraoral scanning session, wherein each of the plurality of 2D images is associated with one of the plurality of intraoral scans;

determine, based on a result of the registering, a position change or an orientation change between at least two 2D images of the plurality of 2D images;

determine, based on timing for the at least two 2D images and based on at least one of the position change or the orientation change, at least one of a rate of position change or a rate of orientation change;

receive one or more additional 2D images, wherein each of the one or more additional 2D images is associated with one of the one or more additional intraoral scans; and determine, based at least in part on a timing of the one or more additional 2D images and at least one of the rate of position change or the rate of orientation change, a position and orientation of the second 3D surface relative to the first 3D surface.

6. The intraoral scanning system of claim 1, wherein the computing device is further to:

input a first input based on the first 3D surface into the trained machine learning model, wherein the trained machine learning model outputs first canonical position coordinates for a first position and orientation of the first 3D surface relative to a canonical position of a jaw; and input a second input based on the second 3D surface into the trained machine learning model, wherein the trained machine learning model outputs second canonical position coordinates for a second position and orientation of the second 3D surface relative to the canonical position of the jaw.

7. The intraoral scanning system of claim 1, wherein the computing device is further to:

receive a plurality of two-dimensional (2D) images during the intraoral scanning session, wherein each of the plurality of 2D images is associated with one of the plurality of intraoral scans;

receive one or more additional 2D images, wherein each of the one or more additional 2D images is associated with one of the one or more additional intraoral scans;

input a first input based on at least a subset of the plurality of 2D images into the trained machine learning model, wherein the trained machine learning model outputs first canonical position coordinates for a first position and orientation of the first 3D surface relative to a canonical position of a jaw; and input a second input based on at least a subset of the one or more additional 2D images into the trained machine learning model, wherein the trained machine learning model outputs second canonical position coordinates for a second position and orientation of the second 3D surface relative to the canonical position of the jaw.

8. The intraoral scanning system of claim 1, wherein the computing device is further to:

input an input based on the first 3D surface and the second 3D surface into the trained machine learning model, wherein the trained machine learning model outputs the relative position and orientation of the second 3D surface and the first 3D surface.

9. The intraoral scanning system of claim 1, wherein the computing device is further to:

receive a further intraoral scan;

determine that the further intraoral scan satisfies the one or more registration criteria for registering to at least one of the one or more additional intraoral scans or the second 3D surface;

determine that the further intraoral scan satisfies the one or more registration criteria for registering to at least one of the plurality of intraoral scans or the first 3D surface; and register the first 3D surface with the second 3D surface using the further intraoral scan.

10. The intraoral scanning system of claim 9, wherein the computing device is further to:

merge the first 3D surface and the second 3D surface into a combined 3D surface.

11. The intraoral scanning system of claim 1, wherein the computing device is further to:

determine one or more reasons that the one or more additional intraoral scans failed to satisfy the one or more registration criteria for registering to at least one of the plurality of intraoral scans or the first 3D surface; and provide feedback regarding the one or more reasons.

12. The intraoral scanning system of claim 11, wherein the one or more reasons are selected from the group consisting of: the intraoral scanner was moved too quickly, the intraoral scanner is too far from a dental site being scanned, the intraoral scanner is too close to the dental site being scanned, there is insufficient overlap between the one or more additional intraoral scans and at least one of the plurality of intraoral scans or the first 3D surface, a window of the intraoral scanner is dirty, the dental site is obstructed by moving tissue, the dental site is obstructed by blood or saliva, and the dental site lacks sufficient surface features.

13. The intraoral scanning system of claim 1, wherein the computing device is further to:

determine one or more reasons why the one or more additional intraoral scans fail to satisfy the one or more registration criteria or are close to failing the one or more registration criteria; and output, via a dashboard of a graphical user interface, a notice indicating the one or more reasons why the one or more additional intraoral scans fail to satisfy the one or more registration criteria or are close to failing the one or more registration criteria.

14. The intraoral scanning system of claim 13, wherein the computing device is further to:

periodically determine values for a plurality of metrics associated with the one or more registration criteria; and output the values for the plurality of metrics via the dashboard of the graphical user interface.

15. The intraoral scanning system of claim 1, wherein the computing device is further to:

determine a speed of movement of the intraoral scanner that generated the plurality of intraoral scans;

determine whether the speed of movement exceeds a speed threshold; and output a warning responsive to determining that the speed of movement exceeds the speed threshold.

16. The intraoral scanning system of claim 1, wherein the computing device is further to:

determine a speed of movement of the intraoral scanner that generated the plurality of intraoral scans; and output an indication of the speed of movement of the intraoral scanner.

17. The intraoral scanning system of claim 1, wherein the computing device is further to:

determine a speed of movement of the intraoral scanner that generated the plurality of intraoral scans;

determine whether the speed of movement exceeds a speed threshold;

output a first indication of the speed of movement using a first visualization responsive to determining that the speed of movement is below the speed threshold; and output a second indication of the speed of movement using a second visualization responsive to determining that the speed of movement exceeds the speed threshold.

18. The intraoral scanning system of claim 1, wherein the computing device is further to:

determine a distance between one or more points in the one or more additional intraoral scans and a head of the intraoral scanner that generated the one or more additional intraoral scans;

determine that the distance is nearer than a distance threshold; and output a notice to move the head of the intraoral scanner further from a dental site being scanned.

19. The intraoral scanning system of claim 1, wherein the second 3D surface is disconnected from the first 3D surface.

20. The intraoral scanning system of claim 1, wherein the computing device is further to:

determine, based on a result of the registering, a position change or an orientation change between at least two intraoral scans of the plurality of intraoral scans;

determine, based on timing for the at least two intraoral scans and based on at least one of the position change or the orientation change, at least one of a rate of position change or a rate of orientation change; and determine, based on a timing of the one or more additional intraoral scans and at least one of the rate of position change or the rate of orientation change, a position and orientation of the second 3D surface relative to the first 3D surface.

21. The intraoral scanning system of claim 1, wherein the computing device is further to:

display the first 3D surface in a first region of the display and the second 3D surface in a second region of the display.

22. An intraoral scanning system comprising:

an intraoral scanner, configured to generate a plurality of intraoral scans during an intraoral scanning session; and a computing device, wherein the computing device is to:
receive the plurality of intraoral scans during the intraoral scanning session;

register the plurality of intraoral scans together based on overlapping features of the plurality of intraoral scans;

generate a first three-dimensional (3D) surface based on the plurality of intraoral scans;

receive one or more additional intraoral scans;

determine that the one or more additional intraoral scans fail to satisfy one or more registration criteria for registering to at least one of the plurality of intraoral scans or the first 3D surface;

determine that the one or more additional intraoral scans failed to satisfy the one or more registration criteria because of a dirty window of the intraoral scanner that generated the plurality of intraoral scans;

output a notice that the intraoral scanner has the dirty window; and generate a second 3D surface based on the one or more additional intraoral scans without interrupting the intraoral scanning session.

23. The intraoral scanning system of claim 22, wherein the computing device is further to:

determine an amount of the dirty window that is dirty; and output an indication of the amount of the dirty window that is dirty.

24. An intraoral scanning system comprising:

an intraoral scanner, configured to generate a plurality of intraoral scans during an intraoral scanning session; and a computing device, wherein the computing device is to:

receive the plurality of intraoral scans during the intraoral scanning session;

register the plurality of intraoral scans together based on overlapping features of the plurality of intraoral scans;

generate a first three-dimensional (3D) surface based on the plurality of intraoral scans;

receive one or more additional intraoral scans;

determine that the one or more additional intraoral scans fail to satisfy one or more registration criteria for registering to at least one of the plurality of intraoral scans or the first 3D surface;

determine that the one or more additional intraoral scans failed to satisfy the one or more registration criteria because of an amount of detected moving tissue exceeding a threshold amount of moving tissue;

output a notice that an excessive amount of moving tissue was detected; and generate a second 3D surface based on the one or more additional intraoral scans without interrupting the intraoral scanning session.

25. The intraoral scanning system of claim 24, wherein the computing device is further to:

input an input based on at least one of the one or more additional intraoral scans or one or more two-dimensional (2D) images associated with the one or more additional intraoral scans into a trained machine learning model, wherein the trained machine learning model outputs an indication of moving tissue that was detected.

26. The intraoral scanning system of claim 24, wherein the computing device is further to:
determine a percentage of the one or more additional intraoral scans that depicts the detected moving tissue; and
output an indication of the percentage of the one or more additional intraoral scans that depicts the detected moving tissue.

27. An intraoral scanning system comprising:
an intraoral scanner, configured to generate a plurality of intraoral scans during an intraoral scanning session; and
a computing device, wherein the computing device is to:
receive the plurality of intraoral scans during the intraoral scanning session;
register the plurality of intraoral scans together based on overlapping features of the plurality of intraoral scans;
generate a first three-dimensional (3D) surface based on the plurality of intraoral scans;
receive one or more additional intraoral scans;
determine that the one or more additional intraoral scans fail to satisfy one or more registration criteria for registering to at least one of the plurality of intraoral scans or the first 3D surface;
generate a second 3D surface based on the one or more additional intraoral scans without interrupting the intraoral scanning session;
determine a distance between one or more points in the one or more additional intraoral scans and a head of the intraoral scanner that generated the one or more additional intraoral scans;
determine that the distance is further than a distance threshold; and
output a notice to move the head of the intraoral scanner closer to a dental site being scanned.

* * * * *